United States Patent
Plucienniczak et al.

(10) Patent No.: US 7,892,787 B2
(45) Date of Patent: Feb. 22, 2011

(54) METHOD FOR PRODUCTION OF RECOMBINANT GROWTH HORMONE IN FORM OF HYBRID PROTEIN

(75) Inventors: Andrzej Plucienniczak, Warsaw (PL); Maria Ludwika Smorawinska, Warsaw (PL); Renata Wolinowska, Warsaw (PL); Diana Mikiewicz-Sygula, Warsaw (PL); Iwona Sokolowska, Warsaw (PL); Natalia Lukasiewicz, Warsaw (PL); Luiza Chojnacka, Warsaw (PL); Grazyna Plucienniczak, Warsaw (PL); Jolanta Kuthan-Styczen, Warsaw (PL); Krystyna Strzezek, Warsaw (PL); Alina Marciniak-Rusek, Warsaw (PL); Anna Kruszynska, Warsaw (PL); Anna Wojtowicz, Warsaw (PL); Anna Mazurkiewicz-Pisarek, Warsaw (PL); Ewa Wojcik, Warsaw (PL)

(73) Assignee: Instytut Biotechnologii I Antybiotykow, Warsaw (PL)

( * ) Notice: Subject to any disclaimer, the term of this patent is extended or adjusted under 35 U.S.C. 154(b) by 280 days.

(21) Appl. No.: 11/482,554

(22) Filed: Jul. 7, 2006

(65) Prior Publication Data
US 2008/0160570 A1    Jul. 3, 2008

Related U.S. Application Data

(63) Continuation-in-part of application No. PCT/PL2005/000003, filed on Jan. 10, 2005.

(30) Foreign Application Priority Data
Jan. 9, 2004  (PL) ..................... 364295

(51) Int. Cl.
C12P 21/06  (2006.01)
C12N 15/09  (2006.01)
C07K 14/475 (2006.01)

(52) U.S. Cl. .............. 435/69.1; 43/320.1; 43/325; 43/471; 536/23.2; 530/412

(58) Field of Classification Search ............. None
See application file for complete search history.

(56) References Cited

U.S. PATENT DOCUMENTS 5,437,986 A * 8/1995 Alroy et al. ............... 435/71.2

FOREIGN PATENT DOCUMENTS

WO   WO2004097011   * 11/2004

OTHER PUBLICATIONS

Baker et al, Oct. 1994, (The Journal of Biological chemistry, vol. 269, No. 41, pp. 25381-25386).*
Wells, 1990, Biochemistry 29:8509-8517.*

* cited by examiner

*Primary Examiner*—Bridget E Bunner
*Assistant Examiner*—Fozia M Hamud
(74) *Attorney, Agent, or Firm*—Paul G. Lunn, Esq.

(57) ABSTRACT

A method of producing somatotropin encompassing the microbiological expression of a recombinant protein containing somatotropin and hybrid polypeptide containing the amino-acid sequence of ubiquitin and the amino-acid sequence of somatotropin.

20 Claims, 34 Drawing Sheets

Figure 1

UBIS1
5' ggg gAA TTC ATA TgC AAA TTT TTg TTA AAA CTT TAA CTg gTA (SEQ ID NO:1)
UBIS2
5' AAA CCA TTA CCT TAg AAg TTg AAT CTT CAg ATA CCA TTg ATA (SEQ ID NO:2)
UBI3P
5' ATg TTA AAT CTA AAA TTC AAg ATA AAg AAg gTA TTC CTC CAg (SEQ ID NO:3)
UBI4P
5' ATC AAC AACg TCT AAT ATT TgC Agg TAA ACA gTT AgA Ag ATg (SEQ ID NO:4)
UBI5P
5' gTC gTA CCC TgT CTg ATT ATA ACA TTC AgA AAg AAT CTA CCT (SEQ ID NO:5)
UBIS6
5' TAC ATC Tgg TCT TAC gTC TCC gCg gTg gTT AAg TCg ACg AgA (SEQ ID NO:6)
UBIS12
5' Agg TAA Tgg TTT TAC CAg TTA Aag (SEQ ID NO:7)
UBI23P
5' tta gAT TTA ACA TTA TCA ATg gTA TC (SEQ ID NO:8)
UBI34P
5' AgA CgT TgT TgA TCT ggA ggA ATA C (SEQ ID NO:9)
UBI45P
5' ACA ggg TAC gAC CAT CTT CTA ACT (SEQ ID NO:10)
UBI56
5' AgA CCA gAT gTA Agg TAg ATT CTT (SEQ ID NO:11)
UBIS PK1
5' TCT CgT CgA CTT AAC CAC CgC ggA gAC (SEQ ID NO:12)

SEQ ID NO: 29

```
         NdeI
        ~~~~~~~~~
     EcoRI
     ~~~~~       UBIS1
1    GGGGAATTCA TATGCAAATT TTTGTTAAAA CTTTAACTGG TAAAACCATT ACCTTAGAAG
                                                 GAAATTGACC ATTTTGGTAA TGAA
                                                    UBIS12 (SEQ ID NO:7)
                                                      UBI3P
61   TTGAATCTTC AGATACCATT GATAATGTTA AATCTAAAAT TCAAGATAAA GAAGGTATTC
                           CTATGGTAA CTATTACAAT TTAGATT                CATAAG
                              (SEQ ID NO:31) UBI23

121  CTCCAGATCA ACAACGTCTA ATATTTGCAG GTAAACAGTT AGAAGATGGT CGTACCCTGT
                 GAGGTCTAGT TGTTGCAGA                TCAA TCTTCTACCA GCATGGGACA
                 UBI34 (SEQ ID NO:32)                        UBI45 (SEQ ID NO:33)
                                                                         SacII
                                                                        ~~~~~~~
181  CTGATTATAA CATTCAGAAA GAATCTACCT TACATCTGGT CTTACGTCTC CGCGGTGGTT
                           TT CTTAGATGGA ATGTAGACCA GA
                              UBI56 (SEQ ID NO:35)
         SalI
        ~~~~~~
241  AAGTCGACGA GA
                                  (SEQ ID NO:14)
Met Gln Ile Phe Val Lys Thr Leu Thr Gly Lys Thr Ile Thr Leu Glu
Val Glu Ser Ser Asp Thr Ile Asp Asn Val Lys Ser Lys Ile Gln Asp
Lys Glu Gly Ile Pro Pro Asp Gln Gln Arg Leu Ile Phe Ala Gly Lys
Gln Leu Glu Asp Gly Arg Thr Leu Ser Asp Tyr Asn Ile Gln Lys Glu
Ser Thr Leu His Leu Val Leu Arg Leu Arg Gly Gly
```

(SEQ ID NO: 16)

PheProThrIleProLeuSerArgLeuPheAspAsnAlaMetLeuArgAlaHisArgLeu
HisGlnLeuAlaPheAspThrTyrGlnGluPheGluGluAlaTyrIleProLysGluGln
LysTyrSerPheLeuGlnAsnProGlnThrSerLeuCysPheSerGluSerIleProThr
ProSerAsnArgGluGluThrGlnGlnLysSerAsnLeuGluLeuLeuArgIleSerLeu
LeuLeuIleGlnSerTrpLeuGluProValGlnPheLeuArgSerValPheAlaAsnSer
LeuValTyrGlyAlaSerAspSerAsnValTyrAspLeuLeuLysAspLeuGluGluGly
IleGlnThrLeuMetGlyArgLeuGluAspGlySerProArgThrGlyGlnIlePheLys
GlnThrTyrSerLysPheAspThrAsnSerHisAsnAspAspAlaLeuLeuLysAsnTyr
GlyLeuLeuTyrCysPheArgLysAspMetAspLysValGluThrPheLeuArgIleVal
GlnCysArgSerValGluGlySerCysGlyPhe***

```
     ttcccaaccattcccttaagtaggcttttttgacaacgctatgctccgcgcccat
cgtctgcaccagctggcctttgacacctaccaggagtttgaagaagcttatatcccaaag
gaacagaagtattcattcctgcagaaccccccagacctccctctgtttctcagagtctatt
ccgacaccctccaacaggaggaaacacaacagaaatccaacctcgagctgctccgcatc
tccctgctgctcatccagtcgtggctggagcccgtgcagttcctcaggagtgtcttcgcc
aacagcctggtgtacggcgcctctgacagcaacgtctatgacctcctaaaggacctagag
gaagggatccaaacgctgatggggaggctggaagatggcagccccggactgggcagatc
ttcaagcagacctacagcaagttcgacacaaactcacacaacgatgacgcactactcaag
aactacgggctgctctactgcttcaggaaggacatggacaaggtcgagacattcctgcgc
atcgtgcagtgccgctctgtggagggcagctgtggcttctaa
```
(SEQ ID NO: 15)

Fig. 2

```
  1 aagcttcagggttgagatgtgtataagagacagactctagccagtttccaagtagaaact
 61 acagtttctaaactgcaacttttttctacttttgcaacttaatctattgactagtcctt
121 ataaatgttaaaacatatatatagaaataaataaaaagaggaggttcatatg
```
(SEQ ID NO: 17)

Fig. 3

```
aggtttataactgagttataaatacttaacttaattattaatggggttttaat
atgaaaaaaataaattagtaaataaagaaaattactcaatattagagactttgc
cggaagatccattatttgaaaataaatcgactttagaaattgatttaaatcaatt
cgatttatttaatagaattgcaaacgaaactgtagaagaacttataataaaagaa
gttaacgatcctaatgaccgaagcgataaaagcaatggtgttaatttaaatgcaa
aagtttatgtagaaaagaaaaaagacttcattaaaaaagatttgttattac
atttgtagataatcttgaggctttagcaaaattaaatttaaaacctaatgagttt
agaattatcgtcgagattgtaaaggttatggaatacggaaatctaattaacctt
cacaatctacaattgcgaaaatttaaatcttgcaaaatcaaatgtaagttatta
ttttaaaaaccttaaaaagaaaaatatattagtagaaaaagacggacacgtcttt
atgaatagtaatatttttctaaaggattagcccatcgtttggacgaagaaaaa
gaaaaatttgaaatccgcacaagtcgaagacgataatttaaaaactcatttta
aaacccaacgggaaattttcactgtttcccgttccgggctttataattttaaag
cctttggcttattctggggtgtgtagttattatttgctgtttctgtgaatattc
ggcatctgctgctgcaatagcagcattgaagagttgtttaaattctgccggttta
tgctcttgtattagatctaaaacatcactgttaatttatattttcatatctct
gagaaattgaagcattttcctttaactgccttttgtattctattatttccaactc
catatcttttattttctgttttatttgaatgatttgttcttgctcagccgtg
gctctggccactgctaacttttgctcctgttgtacccgttcctggactcttctgt
tgaagttctgacggagatcagacaactcagcctctgaatgctctaaacggctctt
aaacccgtttagacgagctataaggggctttcgttcgttcttgtaaggttttaga
gcctttcgtatgtaacgattaacctcagctcctgtgtagtgcttaggcactacct
ccggatctctaaataattttttcttttcttctgtttcaacaactctaatttttc
aatttattattttctatttctaattcggtttcattcttaatgttttaatatcg
ctgtaaaattctttaacttccttatattctgcattcgaaacctctttttttaatcc
cacggattaaacctaatggcttattgtatttaaaatatatatcctgcattgtttc
gtattttttcatatacgatttattgtttagtttatatattccgttttattttcg
attggtgttataaaggcgtgaatatgtggagtttgctcgtccaagtgtaaaactg
cattaattgcattttccccatattcactttgcaaatattccatttgaactttaat
ccaatcctccaattttttgttatttgcaaaaaattctggggaagctgttaaaact
aattcattacaaataacagaagtagaattacgagctttaacattggttgcttgaa
accttgcattaatatcagtccttaaatcaccagaaccgattaaaattcggttttg
ggatttaaggttaggatctgcattatgtgttttcctcaatcgcatattgtgagaa
ttttcccggcgattgaagtatttttgttttttccactcttaaaattgcataag
ccatattcgaaaacctcccgttaaaagcagtaaggttttttcttttggcccct
gccaggctcacaccgagatttctcggtatagtgagtataccttttctgcaatatt
gaaatctataaatacatctacaataaaaaagcaaagtcaacggctcaatccc
tcgcaagggaaaattaaaatttccccttactcacgatttccaataaaagaaaaa
gacagaacgctgagcaagtcaaaattttaattttggcttgtgaagggttgaccaa
gcgaagcgcggtagggaaatctgcgcagatgcttatgtattgcccggaacgggaa
acgtctgttgtagcggtagcgaaaacacatctcccggaacgggggttttcttttg
cgtagcctggcaagttctgctcgatctggaggtttgcaccgtttactctcttact
ttcttattgttttaaatcttacatacccctccagcccttgctattactgacttaa
atcaaaaaaagttatagattcctataacctaaaagttatagatttctataaccc
cagttatagattcctataaccccctaagttggtcattcgaccaacttcttataa
```

Fig. 5a (SEQ ID NO: 18)

```
ctaagttataaaaagttgtaatcatgtattgactagttgtatattttgtttataa
cctgtctcttatacacatctcaaccatcatcgatgaattgtgtctcaaaatctct
gatgttacattgcacaagataaaaatatatcatcatgaacaataaaactgtctgc
ttacataaacagtaatacaaggggtgttatgagccatattcaacgggaaacgtct
tgctcgaggccgcgattaaattccaacatggatgctgatttatatgggtataaat
gggctcgcgataatgtcgggcaatcaggtgcgacaatctatcgattgtatgggaa
gcccgatgcgccagagttgtttctgaaacatggcaaaggtagcgttgccaatgat
gttacagatgagatggtcagactaaactggctgacggaatttatgcctcttccga
ccatcaagcatttatccgtactcctgatgatgcatggttactcaccactgcgat
ccccggaaaaacagcattccaggtattagaagaatatcctgattcaggtgaaaat
attgttgatgcgctggcagtgttcctgcgccggttgcattcgattcctgtttgta
attgtccttttaacagcgatcgcgtatttcgtctcgctcaggcgcaatcacgaat
gaataacggtttggttgatgcgagtgattttgatgacgagcgtaatggctggcct
gttgaacaagtctggaaagaaatgcataaacttttgccattctcaccggattcag
tcgtcactcatggtgatttctcacttgataaccttattttgacgagggaaatt
aataggttgtattgatgttggacgagtcggaatcgcagaccgataccaggatctt
gccatcctatggaactgcctcggtgagttttctccttcattacagaaacggcttt
ttcaaaaatatggtattgataatcctgatatgaataaattgcagtttcatttgat
gctcgatgagttttctaatcagaattggttaattggttgtaacactggcagagc
attacgctgacttgacgggacggcggctttgttgaataaatcgaactttgctga
gttgaaggatcagatcacgcatcttcccgacaacgcagaccgttccgtggcaaag
caaaagttcaaaatcaccaactggtccacctacaacaaagctctcatcaaccgtg
gcggggatcgatcttagatccgttgtttctcgtctaataaatgaacgaaaaatac
ttcaaatgactgatggttatcaggtcactgctttgggggctagctatgttaggag
cgtctttgatagaaagacacttgaccgattgcggcttgagattatgaattttgaa
aaccgtagaaaatcaacatttaactatgataagattccgtatgcgcaccaagaag
gaagaattccatatgcagattttcgtcaaaactttgaccggtaaaaccataacat
tggaagttgaatcttccgataccatcgacaacgttaagtcgaaaattcaagacaa
ggaaggtatccctccagatcaacaaagattgatctttgccggtaagcagctagaa
gacggtagaacgctgtctgattacaacattcagaaggagtccaccttacatcttg
tcttaagactccgcggtggtttcccaaccattcccttatccaggcttttgacaa
cgctagtctccgcgcccatcgtctgcaccagctggcctttgacacctaccaggag
tttgaagaagcttatatcccaaaggaacagaagtattcattcctgcagaaccccc
agacctccctctgtttctcagagtctattccgacaccctccaacagggaggaaac
acaacagaaatccaacctcgagctgctccgcatctccctgctgctcatccagtcg
tggctggagcccgtgcagttcctcaggagtgtcttcgccaacagcctggtgtacg
gcgcctctgacagcaacgtctatgacctcctaaaggacctagaggaagggatcca
aacgctgatggggaggctggaagatggcagcccccggactgggcagatcttcaag
cagacctacagcaagttcgacacaaactcacacaacgatgacgcactactcaaga
actacgggctgctctactgcttcaggaaggacatggacaaggtcgagacattcct
gcgcatcgtgcagtgccgctctgtggagggcagctgtggcttctaaaaagtcgac
gcggccgcaagcttagcccgcttaatgagcgggcttttttttagcttcagggttg
agatgtgtataagagacag
```

(SEQ ID NO: 18)

Fig. 5b actctagccctgtctcttatacacatctcaaccatcatcgatgaattgtg
tctcaaaatctctgatgttacattgcacaagataaaaatatatcatcatg
aacaataaaactgtctgcttacataaacagtaatacaaggggtgttatga
gccatattcaacgggaaacgtcttgctcgaggccgcgattaaattccaac
atggatgctgatttatatgggtataaatgggctcgcgataatgtcgggca
atcaggtgcgacaatctatcgattgtatgggaagcccgatgcgccagagt
tgtttctgaaacatggcaaaggtagcgttgccaatgatgttacagatgag
atggtcagactaaactggctgacggaatttatgcctcttccgaccatcaa
gcattttatccgtactcctgatgatgcatggttactcaccactgcgatcc
ccggaaaaacagcattccaggtattagaagaatatcctgattcaggtgaa
aatattgttgatgcgctggcagtgttcctgcgccggttgcattcgattcc
tgtttgtaattgtccttttaacagcgatcgcgtatttcgtctcgctcagg
cgcaatcacgaatgaataacggtttggttgatgcgagtgattttgatgac
gagcgtaatggctggcctgttgaacaagtctggaaagaaatgcataaact
tttgccattctcaccggattcagtcgtcactcatggtgatttctcacttg
ataaccttattttttgacgaggggaaattaataggttgtattgatgttgga
cgagtcggaatcgcagaccgataccaggatcttgccatcctatggaactg
cctcggtgagttttctccttcattacagaaacggctttttcaaaaatatg
gtattgataatcctgatatgaataaattgcagtttcatttgatgctcgat
gagttttctaatcagaattggttaattggttgtaacactggcagagcat
tacgctgacttgacgggacggcggctttgttgaataaatcgaacttttgc
tgagttgaaggatcagatcacgcatcttcccgacaacgcagaccgttccg
tggcaaagcaaaagttcaaaatcaccaactggtccacctacaacaaagct
ctcatcaaccgtggcggggatcctctagagtcgacctgcaggcatgcaag
cttcagggttgagatgtgtataagagacagactctagccagtttccaagt
agaaactacagtttctaaactgcaacttttctacttttgcaacttaat
ctattgactagtcctttataaatgttaaacatatatatagaaataaata
aaaagaggaggtttctatggatattggaaatatattaaatgagagtttaa
gtattgattacgaaaattagatttgttttggaaaaatatgatttaaca
ccagaacaaaaagttgcagtttatgaatttcacgcaaaagcttataaaaa
aaataaaactttagttatttctgaaacaaagaaaataaatttaaatcta
tttccgaaggtgttgaatacgtgcatttattcccaaaaaatttaaaaatt
ttaattaaaaatatggtttaaatacaaacgaattattggttttaacgga
aataatggagtcaatgctttcacacggaaatttattaattaattttcgc
aaaaggcactttgcgaattaacaggaattaataaatctacaatgtgtaaa
acatttaaaaccctcaaacaaaagcagtgtttaattgagaaaacggaca
tatttatttaaattctgtgatatttatgaagggttacctcataaattgt
ttatgcaatttagagatcattttttaaattctatctcatataaattagat
gatgaagaagaatttgaaaagtcttcgacgataattttattaaagcata
cgaaaaaaatctcaaagagattaaaagaaaagcaacaaataaaagaaa
agaaaatatcaaagcattagataattttgaaaagaaatctcgaaagaa
tggaaggaaaagtttaaagacgaagaggaaaatttcgaatttggttttga (SEQ ID NO: 19)    Fig. 8a atcggaaatataaaaccgccctcgccgggcaggcgaatcccttattgaaa
tagaataaattctattccactaagggattttttttattcattgtttctcc
acatttgcaatattgacattaacttccacccggatataacagtagtataa
gttgttgtttcaacccgtcttttggtggaacaacaaggcattttaggg
atagagcaaagcgaaggccataaaattgccaccccaaccggggtcgtt
gttcgatttgagcgatagcgaaaattgaacataaggggggagggtttgg
gttttacggtatttcaaatttgagcaaagcgaatttttgaaatttccggt
tcttttaatttgcaatgaggaaaaatcaatatgggtaattcaaaagaaa
tataaaaaactaaatgataattttagagaggatattttagattatgcga
tcgcgcacaatctaaaatgtgctaacgcacttgctattttatacgaacg
ggttgccgtccggacgaactccaaaccggagttactgtaaactatgacag
taaaaaaatgaaattgaatttagaataattggatcaaaactaaatagaa
gaatgagaagaggcatagggggttagaaaaataaaagtaaaatcaataat
gaaatgccaggtttttaaaaacattgttgataaatttattgaaaaccc
aatgtcatatgatcacaaaatcaaaattgaaagtgccaaagcattttccg
ggtacataacaaaaatatcgaaaaagctatggcccaggaaaacctatcat
gcttctgcatattcttttagacatgcaaaagcaacggaattaaaaaattc
cgattatgataaaatcgaaatagctcagattatgggccatgcctcagtta
gatctcagcagagttacggaagaaagagcaaaaaaagcaaggtggattt
gatgacatcgcagatgtcgaaccaatgttaaacccgtggcggtgatag
attattgagatttaagatcgcaaataaaacaaagcagcggcaaaaattg
ccgatacttccacccccagcagtcctccaccggctcccgttcgtcgcttc
aaaatgtgaaccgtgagcagttcaggaggttcctcctggactgtgaagg
gttggcccgtccggtcaggacggttttacagcaaaatcctccatagcgaa
gcagaagcccggaacgggtaactggatggttttccccgtgggggattga
tctgttacttgaaaaccaatgatcttaaaagccatctcaaaagttgaaaa
tttcaccccttagtgttcttaaaattcttagatgttcttaggagttaaa
aaactactctctaaccattgatattactggattttaaaaaggcagttg
tcaaaaacttcaaccgtagttgtcaaattcgtcaactccagttgtcaaat
tcgtcaactgaggttgtcaaatccgaca (SEQ ID NO: 19)

Fig. 8b

```
actctagccctgtctcttatacacatctcaaccatcatcgatgaattgt
gtctcaaaatctctgatgttacattgcacaagataaaatatatcatca
tgaacaataaaactgtctgcttacataaacagtaatacaaggggtgtta
tgagccatattcaacgggaaacgtcttgctcgaggccgcgattaaattc
caacatggatgctgatttatatgggtataaatgggctcgcgataatgtc
gggcaatcaggtgcgacaatctatcgattgtatgggaagcccgatgcgc
cagagttgtttctgaaacatggcaaggtagcgttgccaatgatgttac
agatgagatggtcagactaaactggctgacggaatttatgcctcttccg
accatcaagcatttatccgtactcctgatgatgcatggttactcacca
ctgcgatccccggaaaaacagcattccaggtattagaagaatatcctga
ttcaggtgaaaatattgttgatgcgctggcagtgttcctgcgccggttg
cattcgattcctgtttgtaattgtccttttaacagcgatcgcgtatttc
gtctcgctcaggcgcaatcacgaatgaataacggtttggttgatgcgag
tgattttgatgacgagcgtaatggctggcctgttgaacaagtctggaaa
gaaatgcataaacttttgccattctcaccggattcagtcgtcactcatg
gtgatttctcacttgataaccttattttttgacgaggggaaattaatagg
ttgtattgatgttggacgagtcggaatcgcagaccgataccaggatctt
gccatcctatggaactgcctcggtgagttttctccttcattacagaaac
ggctttttcaaaaatatggtattgataatcctgatatgaataaattgca
gtttcatttgatgctcgatgagttttctaatcagaattggttaattgg
ttgtaacactggcagagcattacgctgacttgacgggacggcggctttg
ttgaataaatcgacttttgctgagttgaaggatcagatcacgcatctt
cccgacaacgcagaccgttccgtggcaaagcaaaagttcaaaatcacca
actggtccacctacaacaaagctctcatcaaccgtggcggggatccgga
ccgttggcgatgtgcggtttgctacattcacagatgttcttcgccactt
ccagcagcaggtcatcagggtgatttcaggatcgtagataaaggtcag
gttcggtgaaacctgcttcaactctgcatctgcacgtaagatcgcgcgg
gtaatgggcgaatcagacgggccgatattggcgtgcataaaggcgtctg
gcagggttctgtcgaggtaacgccagaaacgttttattcgaacatcgat
ctcgtcttgtgttagaattaattctaacatacggttgcaacaacgcatc
cagttgccccaggtagaccggcatcgatgtgaccgacggtacgtggtgg
taaagaatggtcagcagagagagtgcgtcatcaagatctttcgcgcctt
ccagctccagccattcggaaccgttcgccagaaacgggcgtaatcggg
taagacatagcgcggtttgtacggcgcatgaccttcaaacatatcgcag
attacaccttcatccagcgcgcggcgggcttcggcaggaagctgtggt
aaggcagattgttttctgcttccagtgccagaaatggcgcttctgctc
cgggctaagcactgggctggtgacaatttgctggcaacgttgttgcagt
gcattttcatgagaagtgggcatcttctttcctttatgccgaaggtg
atgcgccattgtaagaagtttcgtgatgttcactttgatcctgatgcgt
ttgccaccactgacgcattcatttgaaagtgaattatttgaaccagatc
gcattacagtgatgcaaacttgtaagtagatttccttaattgtgatgtg
tatcgaagtgtgttgcggagtagatgttagaatactaacaaactcgcaa
```

Fig. 10a  (SEQ ID NO: 20)

```
ggtgaattttattggcgacaagcctaggtttgtttaactttaaggagaa
atcatatgcaattttgttaaaactttaactggtaaaaccattaccttt
agaagttgaatcttcagataccattgataatgttaaatctaaaattcaa
gataaagaaggtattcctccagatcaacaacgtctaatatttgcaggta
aacagttagaagatggtcgtaccctgtctgattataacattcagaaaga
atctaccttacatctggtcttacgtctccgcggtggtttcccaaccatt
cccttaagtaggcttttgacaacgctatgctccgcgccatcgtctgc
accagctggcctttgacacctaccaggagtttgaagaagcttatatccc
aaaggaacagaagtattcattcctgcagaaccccagacctccctctgt
ttctcagagtctattccgacaccctcaacagggaggaaacacaacaga
aatccaacctcgagctgctccgcatctcctgctgctcatccagtcgtg
gctggagcccgtgcagttcctcaggagtgtcttcgccaacagcctggtg
tacggcgcctctgacagcaacgtctatgacctcctaaaggacctagagg
aagggatccaaacgctgatggggaggctggaagatggcagcccccggac
tgggcagatcttcaagcagacctacagcaagttcgacacaaactcacac
aacgatgacgcactactcaagaactacggctgctctactgcttcagga
aggacatggacaaggtcgagacattcctgcgcatcgtgcagtgccgctc
tgtggagggcagctgtggcttctaaaaagtcgacctgcaggcatgcaag
cttagcccgcttaatgagcgggcttttttttctcgacctgcaggcatgc
aagcttcaggggttgagatgtgtataagagacagactctagccagtttcc
aagtagaaactacagtttctaaactgcaactttttctacttttgcaac
ttaatctattgactagtcctttataaatgttaaacatatatatagaaa
taaataaaagaggaggtttctatggatattggaaatatattaaatgag
agtttaagtattgattacgaaaaattagatttgttttggaaaaatatg
atttaacaccagaacaaaaagttgcagtttatgaatttcacgcaaaagc
ttataaaaaaataaaactttagttatttctgaaacaaaagaaaataaa
tttaaatctatttccgaagtgttgaatacgtgcatttattcccaaaaaa
tttaaaattttaattaaaaatatggtttaaatacaaacgaattattg
gttttaacggaaataatggagtcaatgctttcacacggaaatttattaa
ttaattttcgcaaaaggcactttgcgaattaacaggaattaataaatc
tacaatgtgtaaaacatttaaaccctcaaacaaaagcagtgtttaatt
gagaaaacggacatatttatttaaattctgtgatatttatgaaagggt
tacctcataaattgtttatgcaatttagagatcatttttaaattctat
ctcatataaattagatgatgaagaagaatttgaaaaagtcttcgacgat
aatttattaaagcatacgaaaaaatctcaaagagattaaaaagaaaa
agcaacaaataaaagaaagaaaatatcaaaagcattagataattttga
aaaagaaatctcgaaagaatggaaggaaaagtttaagacgaagaggaa
aatttcgaatttggttttgaatcggaaatataaaaccgccctcgccggg
caggcgaatcccttattgaaatagaataaattctattccactaagggat
ttttttattcattgtttctccacatttgcaatattgacattaacttcc
acccggatataacagtagtataagttgttgtttcaacccgtcttttgg
gtggaacaacaaggcatttagggatagagcaaagcgaaggccataaaa
```

(SEQ ID NO: 20)  Fig. 10b ttgccaccccaaccggggggtcgttgttcgatttgagcgatagcgaaaa
attgaacataaggggggagggtttgggttttacggtatttcaaatttga
gcaaagcgaattttttgaaatttccggttcttttaatttgcaatgaggaa
aaatcaatatgggtaattcaaaaagaaatataaaaaaactaaatgataa
ttttagagaggatattttagattatgcgatcgcgcacaatctaaaatgt
gctaacgcacttgctattttatacgcaacgggttgccgtccggacgaac
tccaaaccggagttactgtaaactatgacagtaaaaaaatgaaattga
atttagaataattggatcaaaactaaatagaagaatgagaagaggcata
ggggttagaaaaataaaagtaaaaatcaataatgaaaatgccaggtttt
ttaaaaacattgttgataaatttattgaaacccaatgtcatgatcaca
aaatcaaaattgaaagtgccaaagcattttccgggtacataacaaaaat
atcgaaaaagctatggcccaggaaaacctatcatgcttctgcatattct
tttagacatgcaaaagcaacggaattaaaaattccgattatgataaaa
tcgaaatagctcagattatgggccatgcctcagttagatctcagcagag
ttacggaagaaagagcaaaaaagcaaggtggatttgatgacatcgca
gatgtcgaaccaatgttaaacccgtggcggtgatagattattgagat
ttaagatcgcaaataaaacaaagcagcggcaaaaattgccgatacttc
cacccccagcagtcctccaccggctcccgttcgtcgcttcaaaatgtga
accgtgagcagttcaggaggttccctcctggactgtgaagggttggccc
gtccggtcaggacggttttacagcaaaatcctccatagcgaagcagaag
cccggaacggtaactggatggttttccccgtgggggattgatctgtta
cttgaaaccaatgatcttaaaagccatctcaaaagttgaaaatttcac
cccttagtgttcttaaaattcttagatgttcttaggagttaaaaaact
actctctaaccattgatattggattttaaaaaaggcagttgtcaa
aaacttcaccgtagttgtcaaattcgtcaactccagttgtcaaattcg
tcaactgaggttgtcaaatccgaca (SEQ ID NO: 20)

Fig. 10c

(SEQ ID NO: 21)

```
tagagcgcacgaatgagggccgacaggaagcaaagctgaaaggaatcaaatttggccgcaggcgtaccgtg
gacaggaacgtcgtgctgacgcttcatcagaagggcactggtgcaacggaaattgctcatcagctcagtat
tgcccgctccacggtttataaaattcttgaagacgaaagggcctcgtgatacgcctatttttataggttaa
tgtcatgataataatggtttcttagacgtcaggtggcacttttcggggaaatgtgcgcggaaccccta ttt
gtttattttctaaatacattcaaatatgtatccgctcatgagacaataaccctgataaatgcttcaataa
tattgaaaaaggaagagtatgagtattcaacatttccgtgtcgcccttattccctttttgcggcattttg
ccttcctgttttgctcacccagaaacgctggtgaaagtaaaagatgctgaagatcagttgggtgcacgag
tgggttacatcgaactggatctcaacagcggtaagatccttgagagttttcgccccgaagaacgttttcca
atgatgagcacttttaaagttctgctatgtggcgcggtattatcccgtgttgacgccgggcaagagcaact
cggtcgccgcatacactattctcagaatgacttggttgagtactcaccagtcacagaaaagcatcttacgg
atggcatgacagtaagagaattatgcagtgctgccataaccatgagtgataacactgcggccaacttactt
ctgacaacgatcggaggaccgaaggagctaaccgcttttttgcacaacatggggatcatgtaactcgcct
tgatcgttgggaaccggagctgaatgaagccataccaaacgacgagcgtgacaccacgatgcctgcagcaa
tggcaacaacgttgcgcaaactattaactggcgaactacttactctagcttcccggcaacaattaataga
tggatggaggcggataaagttgcaggaccacttctgcgctcggcccttccggctggctggtttattgctga
taaatctggagccggtgagcgtgggtctcgcggtatcattgcagcactggggccagatggtaagccctccc
gtatcgtagttatctacacgacggggagtcaggcaactatggatgaacgaaatagacagatcgctgagata
ggtgcctcactgattaagcattggtaactgtcagaccaagtttactcatatatactttagattgatttaaa
acttcatttttaatttaaaaggatctaggtgaagatcctttttgataatctcatgaccaaaatcccttaac
gtgagttttcgttccactgagcgtcagaccccatcgccgttctcgatacgctgaaccgtgcgcacgctcat
cccggacagttcagcaagctgctcctgggaccaggcacgcgcaagacgcagcgacctgaatttgttggtat
cactcatttcctgtctccgaatggaagatggtcagcacacagtgttgaccgcgtaatcctgcgcgaccacg
atcttaacccgacagtaacgtgacagcggtctgacatgccgcattgaggtctttgaaaccgtaacttcaga
agcatgtacggtcagatttaacataagagttcattgtacgcaccgttaaaacgcgctcagcgcgcttctgg
cgcaaaaaccgtaaaatggatgtttcccccgggtaaaccggaaaaatgcgtcaggaacgctttcagcgc
gttgcatgactatgcatgaaactgaatggcgatcggtttgggcgcgtctgatgcccataaggcgtattttc
ggacgttttcagccctgataagaagaaatcagactgtagttacagacgagtcgtgagcgattcactacggg
agtcgtcggcgagtcatccagtattttcctcgcgactctctggcgactcgccttctctgaacaccagagc
gacagtgtgttgagtcatcgataaatcaccgacgactcgttgccgagtcatccagtagtcgccgacgagcc
gcttttgtataaatccgaataagaaaatatattttcaaaccataacaacatgatttaaaaagcaaatcag
aaaaagttagttttgcgtggggtgtgggcatcctgggaatgagaacagactcgcgttttctggaggaac
tgcggggattttgattaaacaatagtcaccgcagagcggaattttatgcaacgctggctgtgcggcacgg
ggatttttaatcccccggcccgttattcatctccacgggcgacggggatacataaacccgacagcagagga
cgggtgagcgcgaatcccagagatgatgaaaaagaggcagagaaacgcgcccaggtacgttttatcttat
tgctttggtgttgtccagggtgtcggggctgtgccctgaccaggtggcatttgtctgattgcgcgtgcgcg
gtccgacaaatgcacatcctgccccgtcctgtacgtgttttttcaccagaacaacttcacgaagtggcgg
atgaacgctaccaacgttgccgggaacgcttcggcgatgatggcataacgggctgatacaggcagctcccg
gagacggacacagcttgcctgtgagcggatgccgggagccgacaagcccgtcagggcgcgtcagcgggttt
tagcgggtgtcggggcgcagccatgacccagtcacgtagcgatagcggagtgtatactggcttaatatgtt
aaatcggagtggtaattcagggaagtgcttcatgtggcaaaggaaaaatgtggctatcgtgcgtaagtgca
acatgtaggtaaaggtgaaatgacgcctcctcgctcactcggtcgctacgctcctgccgtgagactgcggc
gggcgttaccggctcacaaataacgggatacgcaggcagtgctcaaatcaggaaggaccggaaaaaggatg
cggcgtagccgttttccataggctccgcccccctgacaagcatcacgaaatctgacgctcaaatcagtgg
cggcgaaacccgacaggactataaagatccaggcgtttccccctggtagctccctcgtgcgctctcctgt
tcctgcctttcggtttaccggtgtcattccgctgttatggccgcgtttgtctcattccacgcctgacactc
agttccgggtaggcagttcgctccaagctggactgtatgcacgaaccccccgttcagtccgactaccacgc
ccgttccggtaactatcaacttgagtccaacccggaaagacacgacaaatcgccagtggcggtagccattg
gtaactgagatgtgcgagagatttatctggagttcttgaagtgggggcctgagtgcggctacactggaagg
acagtttaggtgactcgtctcgcacaagacagttaccaggttaagcagttccccaactgacctaaccttcg
atcaaaccacctcccaggtggttttttcgttttcagagcaagagattacgcgcagaaaaaaggatctca
agaagatccttttttacaggagcgattatcgtcttcatccatgaaggcgtttgaagattaaaccggcctatt
tcatagatcgtaaaatcagggttttgggatggccgatgaaacccataaaaacccataaatacatacacct
actaacaatcatcttttgctgtaccagggtatgaaagtctcaggttccacccagaatacgccatcaac
aagtcctgtcacaccgccaaataacatgcaaaaattgcggatgaccgtaatccggggtgcagatcaatga
ctgagacaagtataaacttcatgcaaaaagtaattacaatcagtcccaaagtcagcggtgtcccggccctg
ataatcatgcccggattatctgaatttctcagcgggggctgtgagcgccacaacctgtatccaagagcggt
gcctacgagcagtcctgccgtcatcattgtaaggcttacgccagcaagttttgtctcagtgataacacctt
```

Fig. 12a

```
atgctccccatacaaggaaaagtatcgggagaaaaaacaaacgcccggttgtcatctcccggtcataaaga
gcagcaaaaccgcgtcgtagtaaaaaagccagcaggatcaagcttcagggttgagatgtgtataagagaca
gactctagccagtttccaagtagaaactacagtttctaaactgcaactttttctacttttgcaacttaat
ctattgactagtcctttataaatgttaaaacatatatatagaaataaataaaaagaggaggttcatatgca
aatttttgttaaaactttaactggtaaaaccattaccttagaagttgaatcttcagataccattgataatg
ttaaatctaaaattcaagataaagaaggtattcctccagatcaacaacgtctaatatttgcaggtaaacag
ttagaagatggtcgtaccctgtctgattataacattcagaaagaatctaccttacatctggtcttacgtct
ccgcggtggtttcccaaccattcccttaagtaggcttttgacaacgctatgctccgcgcccatcgtctgc
accagctggcctttgacacctaccaggagtttgaagaagcttatatcccaaaggaacagaagtattcattc
ctgcagaaccccagacctccctctgtttctcagagtctattccgacaccctccaacagggaggaaacaca
acagaaatccaacctcgagctgctccgcatctccctgctgctcatccagtcgtggctggagcccgtgcagt
tcctcaggagtgtcttcgccaacagcctggtgtacggcgcctctgacagcaacgtctatgacctcctaaag
gacctagaggaagggatccaaacgctgatggggaggctggaagatggcagccccggactgggcagatctt
caagcagacctacagcaagttcgacacaaactcacacaacgatgacgcactactcaagaactacgggctgc
tctactgcttcaggaaggacatggacaaggtcgagacattcctgcgcatcgtgcagtgccgctctgtggag
ggcagctgtggcttctaaaaagtcgactctagctacagcctcctttcggaggctgttttttatctcgagga
                                                                     tcc
```

(SEQ ID NO: 21)

Fig. 12b (SEQ ID NO: 22)

```
tagagcgcacgaatgagggccgacaggaagcaaagctgaaaggaatcaaatttggccgcaggcgtaccgtggaca
ggaacgtcgtgctgacgcttcatcagaagggcactggtgcaacggaaattgctcatcagctcagtattgcccgct
ccacggtttataaaattcttgaagacgaaagggcctcgtgatacgcctatttttataggttaatgtcatgataat
aatggtttcttagacgtcaggtggcacttttcggggaaatgtgcgcggaaccccctatttgtttatttttctaaat
acattcaaatatgtatccgctcatgagacaataaccctgataaatgcttcaataatattgaaaaggaagagtat
gagtattcaacatttccgtgtcgcccttattccctttttttgcggcatttttgccttcctgttttttgctcacccaga
aacgctggtgaaagtaaaagatgctgaagatcagttgggtgcacgagtgggttacatcgaactggatctcaacag
cggtaagatccttgagagttttcgccccgaagaacgttttccaatgatgagcacttttaaagttctgctatgtgg
cgcggtattatcccgtgttgacgccgggcaagagcaactcggtcgccgcatacactattctcagaatgacttggt
tgagtactcaccagtcacagaaaagcatcttacggatggcatgacagtaagagaattatgcagtgctgccataac
catgagtgataacactgcggccaacttacttctgacaacgatcggaggaccgaaggagctaaccgcttttttgca
caacatgggggatcatgtaactcgccttgatcgttgggaaccggagctgaatgaagccataccaaacgacgagcg
tgacaccacgatgcctgcagcaatggcaacaacgttgcgcaaactattaactggcgaactacttactctagcttc
ccggcaacaattaatagactggatggaggcggataaagttgcaggaccacttctgcgctcggcccttccggctgg
ctggtttattgctgataaatctggagccggtgagcgtgggtctcgcggtatcattgcagcactggggccagatgg
taagccctcccgtatcgtagttatctacacgacggggagtcaggcaactatggatgaacgaaatagacagatcgc
tgagataggtgcctcactgattaagcattggtaactgtcagaccaagtttactcatatatactttagattgattt
aaaacttcatttttaatttaaaaggatctaggtgaagatcctttttgataatctcatgaccaaaatcccttaacg
tgagttttcgttccactgagcgtcagaccccatcgccgttctcgatacgctgaaccgtgcgcacgctcatcccgg
acagttcagcaagctgctcctgggaccaggcacgcgcaagacgcagcgacctgaatttgttggtatcactcattt
cctgtctccgaatggaagatggtcagcacacagtgttgaccgcgtaatcctgcgcgaccacgatcttaacccgac
agtaacgtgacagcggtctgacatgccgcattgaggtctttgaaaccgtaacttcagaagcatgtacggtcagat
ttaacataagagttcattgtacgcaccgttaaaacgcgctcagcgcgcttctggcgcaaaaaccgtaaaaatgga
tgttttccccgggtaaaccggaaaaatgcgtcaggaacgctttcagcgcgttgcatgactatgcatgaaactga
atggcgatcggtttgggcgcgtctgatgcccataaggcgtattttcggacgttttcagccctgataagaagaaat
cagactgtagttacagacgagtcgtgagcgattcactacgggagtcgtcggcgagtcatccagtattttcctcg
cgactctctggcgactcgccttctctgaacaccagagcgacagtgtgttgagtcatcgataaatcaccgacgact
cgttgccgagtcatccagtagtcgccgacgagccgcttttgtataaatccgaataagaaaatatattttcaaac
cataacaacatgatttaaaaagcaaatcagaaaaaagttagtttttgcgtggggtgtgggcatcctgggaatgaga
acagactcgcgttttctggaggaactgcggggattttttgattaaacaatagtcaccgcagagcggaattttatg
caacgctggctgtgcggcacggggattttttaatcccccggcccgttattcatctccacgggcgacggggatacat
aaacccgacagcagaggacgggtgagcgcgaatcccagagatgatgaaaaaagaggcagagaaacgcgcccaggt
acgttttatcttattgctttggtgttgtccagggtgtcggggctgtgccctgaccaggtggcatttgtctgattg
cgcgtgcgcggtccgacaaatgcacatcctgccccgtcctgtacgtgttttttttcaccagaacaacttcacgaag
tggcggatgaacgctaccaacgttgccgggaacgcttcggcgatgatggcataacgggctgatacaggcagctcc
cggagacggacacagcttgcctgtgagcggatgccgggagccgacaagcccgtcagggcgcgtcagcgggtttta
gcgggtgtcggggcgcagccatgatccagtcacgtagcgatagcggagtgtatactggcttaatatgttaaatcg
gagtggtaattcagggaagtgcttcatgtggcaaaggaaaaatgtggctatcgtgcgtaagtgcaacatgtaggt
aaaggtgaaatgacgcctcctcgctcactcggtcgctacgctcctgccgtgagactgcggcgggcgttaccggct
cacaaataacgggatacgcaggcagtgctcaaatcaggaaggaccggaaaaaggatgcggcgtagccgttttcc
ataggctccgcccccctgacaagcatcacgaaatctgacgctcaaatcagtggcggcgaaacccgacaggactat
aaagatcccaggcgtttccccctggtagctccctcgtgcgctctcctgttcctgcctttcggtttaccggtgtca
ttccgctgttatggccgcgtttgtctcattccacgcctgacactcagttccgggtaggcagttcgctccaagctg
gactgtatgcacgaaccccccgttcagtccgactaccacgcccgttccggtaactatcaacttgagtccaacccg
gaaagacacgacaaatcgccagtggcggtagccattggtaactgagatgtgcgagagatttatctggagttcttg
aagtgggggcctgagtgcggctacactggaaggacagtttaggtgactcgtctcgcacaagacagttaccaggtt
aagcagttcccaactgacctaaccttcgatcaaaccacctccccaggtggttttttcgttttcagagcaagaga
ttacgcgcagaaaaaaggatctcaagaagatccttttacaggagcgattatcgtcttcatccatgaaggcgtt
tgaagattaaaccggcctatttcatagatcgtaaaatcagggttttgggatggccgatgaaacccataaaaacc
cataaatacatacacctactaacaatcatcttttgctgtaccagggtatgaaagtctcagggttccacccaga
atacgccatcaacaagtcctgtcacaccgccaaataacatgcaaaaaattgcggatgaccgtaatccggggtgca
gatcaatgactgagacaagtataaacttcatgcaaaagtaattacaatcagtcccaaagtcagcggtgtcccgg
ccctgataatcatgcccggattatctgaatttctcagcgggggctgtgagcgccacaacctgtatccaagagcgg
tgcctacgagcagtcctgccgtcatcattgtaaggcttacgccagcaagttttgtctcagtgataacaccttatg
ctccccatacaaggaaaagtatcgggagaaaaaacaaacgcccggttgtcatctcccggtcataagagcagcaa
aaccgcgtcgtagtaaaaaagccagcaggatcctcgagataaaaaacagcctccgaaggaggctgtagtctaga
gcggccgcatttaaatgtcgactttttagaagccacagctgccctccacagagcggcactgcacgatgcgcagga
```

Fig. 14a

```
atgtctcgaccttgtccatgtccttcctgaagcagtagagcagcccgtagttcttgagtagtgcgtcatcgttgt
gtgagtttgtgtcgaacttgctgtaggtctgcttgaagatctgcccagtccgggggctgccatcttccagcctcc
ccatcagcgtttggatcccttcctctaggtcctttaggaggtcatagacgttgctgtcagaggcgccgtacacca
ggctgttggcgaagacactcctgaggaactgcacgggctccagccacgactggatgagcagcagggagatgcgga
gcagctcgaggttggatttctgttgtgtttcctccctgttggagggtgtcggaatagactctgagaaacagaggg
aggtctgggggttctgcaggaatgaatacttctgttcctttgggatataagcttcttcaaactcctggtaggtgt
caaaggccagctggtgcagacgatgggcgcggagcatagcgttgtcaaaaagcctacttaagggaatggttggga
aaccaccgcggagacgtaagaccagatgtaaggtagattctttctgaatgttataatcagacagggtacgaccat
cttctaactgtttacctgcaaatattagacgttgttgatctggaggaataccttctttatcttgaattttagatt
taacattatcaatggtatctgaagattcaacttctaaggtaatggttttaccagttaaagttttaacaaaaattt
gcatatgaacctcctctttttatttatttctatatatatgttttaacatttataaaggactagtcaatagattaa
gttgcaaaaagtagaaaaagttgcagtttagaaactgtagtttctacttggaaactggctagagtctgtctctta
tacacatctcaaccctgaagcttagcccgctcattaagcgggctagcttgatcc
```

(SEQ ID NO: 22)

Fig. 14b

```
   1 gttaggcgcg aggtgctatg gtcaaagtgt ggtgtcaggc ggggaggagg cttatatgag
  61 atgtaatccg gccgatacat ataccaagat gatttaagta ttcctctttg tgaggttgga
 121 tgtctaattt ataaaggatc ttcttgagat ccttttttttc cgcgcgtaat ctcttgccct
 181 gtaaacgaaa aaaccaccct ggcaggtggt ttttcgaagg ttaggtaatc ctggcagatc
 241 ccctaaccgt ggtaacagtc ttgtgcgaga catgtcacca aatttgtcct ttcagtgtag
 301 cctcactaag gccgccactt caagaactct tgagacatct ctcgcacatc ctgtttgcca
 361 atggccgttg ccaatggcga ttagtcgtgt ctttcgggt tggactcaag ttgatagtta
 421 ccggataagg cgcagcggtc ggactgaacg gggggttcgt gcatacagtc catcctggag
 481 cgaactgcct tcccggaact gagtgtcagg cgtggaatga aaaccgcgg ccataacagc
 541 ggagtgacac cggtaaaccg aaaggcagga atgcggggga gcacgaggga gccaccaggg
 601 ggaaacgcct ggtatcttta agccgcatcg ggtttcgcca ccactgattt gagcgtcaga
 661 ttctgtgatg cttgtcaggg gggcggagcc tatggaaaaa cggctttggc gcggccttat
 721 gctttcttcg ttaagtatct tcctggcatc ccccaggaaa tttctgatcc atccgtaagc
 781 ccgtcccgct cgccgcagcc gaacgaccga gcggagcgag tcagtgagcg aggaagcgga
 841 atatattctg tatcacattt tctcctgacg cgttttcttt cactttctgc gcctgtctta
 901 tgtggcatta atgctatgtg ttactgccat gctacatctt aagccagtat acactccgct
 961 agtgctccgt gactggtccg gcgctgcgcc cggaacccgc ctgtaccggt tcagcagccg
1021 ttccggcctg actgcaattt tttttttttc atccctgccc gctaccctgt aaacctttct
1081 tctgcgttgc cgttaacctg tctcttatac acatctcaac catcatcgat gaattgtgtc
1141 tcaaaatctc tgatgttaca ttgcacaaga taaaaatata tcatcatgaa caataaaact
1201 gtctgcttac ataaacagta atacaagggg tgttatgagc catattcaac gggaaacgtc
1261 ttgctcgagg ccgcgattaa attccaacat ggatgctgat ttatatgggt ataaatggc
1321 tcgcgataat gtcgggcaat caggtgcgac aatctatcga ttgtatggga agcccgatgc
1381 gccagagttg tttctgaaac atggcaaagg tagcgttgcc aatgatgtta cagatgagat
1441 ggtcagacta aactggctga cggaatttat gcctcttccg accatcaagc attttatccg
1501 tactcctgat gatgcatggt tactcaccac tgcgatcccc ggaaaaacag cattccaggt
1561 attagaagaa tatcctgatt caggtgaaaa tattgttgat gcgctggcag tgttcctgcg
1621 ccggttgcat tcgattcctg tttgtaattg tccttttaac agcgatcgcg tatttcgtct
1681 cgctcaggcg caatcacgaa tgaataacgg tttggttgat gcgagtgatt ttgatgacga
1741 gcgtaatggc tggcctgttg aacaagtctg gaaagaaatg cataaacttt tgccattctc
1801 accggattca gtcgtcactc atggtgattt ctcacttgat aaccttattt ttgacgaggg
1861 gaaattaata ggttgtattg atgttggacg agtcggaatc gcagaccgat accaggatct
1921 tgccatccta tggaactgcc tcggtgagtt ttctccttca ttacagaaac ggctttttca
1981 aaaatatggt attgataatc ctgatatgaa taaattgcag tttcatttga tgctcgatga
2041 gtttttctaa tcagaattgg ttaattggtt gtaacactgg cagagcatta cgctgacttg
2101 acgggacggc ggctttgttg aataaatcga acttttgctg agttgaagga tcagatcacg
2161 catcttcccg acaacgcaga ccgttccgtg gcaaagcaaa agttcaaaat caccaactgg
2221 tccacctaca acaaagctct catcaaccgt ggcggggatc caaacgcaaa aaggccatcc
2281 gtcaggatgg ccttctgctt aatttgatgc ctggcagttt atggcgggcg tcctgcccgc
2341 caccctccgg gccgttgctt cgcaacgttc aaatccgctc cggcggatt tgtcctactc
2401 aggagagcgt tcaccgacaa caacagata aaacgaaagg cccagtcttt cgactgagcc
2461 tttcgtttta tttgtctaga gtcgactttt tagaagccac agctgccctc cacagagcgg
2521 cactgcacga tgcgcaggaa tgtctcgacc ttgtccatgt ccttcctgaa gcagtagagc
```

Fig. 16a (SEQ ID NO: 23)

```
2581 agcccgtagt tcttgagtag tgcgtcatcg ttgtgtgagt ttgtgtcgaa cttgctgtag
2641 gtctgcttga agatctgccc agtccggggg ctgccatctt ccagcctccc catcagcgtt
2701 tggatccctt cctctaggtc ctttaggagg tcatagacgt tgctgtcaga ggcgccgtac
2761 accaggctgt tggcgaagac actcctgagg aactgcacgg gctccagcca cgactggatg
2821 agcagcaggg agatgcggag cagctcgagg ttggatttct gttgtgtttc ctccctgttg
2881 gagggtgtcg gaatagactc tgagaaacag agggaggtct ggggttctg caggaatgaa
2941 tacttctgtt cctttgggat ataagcttct tcaaactcct ggtaggtgtc aaaggccagc
3001 tggtgcagac gatgggcgcg gagactagcg ttgtcaaaaa gcctacttaa gggaatggtt
3061 gggaaaccac cgcggagacg taagaccaga tgtaaggtag attctttctg aatgttataa
3121 tcagacaggg tacgaccatc ttctaactgt ttacctgcaa atattagacg ttgttgatct
3181 ggaggaatac cttctttatc ttgaatttta gatttaacat tatcaatggt atctgaagat
3241 tcaacttcta aggtaatggt tttaccagtt aaagttttaa caaaaatttg catatgaaac
3301 ctccttaaag ttaattttat ttatttctat atatatgttt taacatttat aaaggactag
3361 tcaatagatt aagttgcaaa aagtagaaaa agttgcagtt tagaaactgt agtttctact
3421 tggaaactgg ctagagtctg tctcttatac acatctcaac cctgaagctt ttagctttgg
3481 tgatgcaatt tgctgggatt ttggcggaga accacaggta aagaaaaagg ccacattagc
3541 ggccttttc ggagaagatg ctcagtgcgg aatttcggag acttctttaa cgtcggtttt
3601 attgatctgc tgtttgacac cattcgcgtc tgtatagcca agcaggcctg agtctgattc
3661 tttaggtttg ccgtcgctga caatagtgcg accgtcattg gtgtgtatgg catagcttgt
3721 gcgcgtgcag ccggtgaggg ctgaaagcgc aactgccgct gcgaacactg aaacaaaaat
3781 cttttcaaa gccagctcct tttatccata tcagttttgg tcactaacca tctaactata
3841 ggtcattttt tatgtgaaaa gaggcttgat ggtgggctgt atatcga
```

Fig. 16b  (SEQ ID NO: 23)

Dissolution of inclusion bodies in DRCI pH 12.0 (corr. to pH 7.0)
1,6 - 2,4 mg/ml
ca. 220 mg/1L of culture

DEAE Sepharose FF(sr.2,5cm, 85ml) ( 6-8 M urea, pH 7.0)
0,85 – 1,3 mg/ml
ca. 120 mg

SP Sepharose FF (sr.1,5cm, 30 ml) ( 6-8 M urea, pH 7.0)
0,7 – 1,3 mg/ml
ca. 115 mg

Renaturation of BR pH 7.0 ( through the dilution of 0,1 mg/ml protein)
0,09 – 0,15 mg/ml
ca. 115 mg

Precipitation with ammonium sulphate to 80% saturation
( resuspension in 20mM PBS pH 7,0+0,5M NaCl)
2,0 – 4,0 mg/ml
ca. 70 mg

Digestion
(UBP1ΔC2  1 µl – 30 µg protein
UBP1Δ C  1 µl – 7 µg protein
Yeast extract 1µl- 2µg protein )
1 h  -  37°C
1,2 – 2,3 mg/ml
ca. 55 mg

Phenylo Sepharose FF ( śr. 1,6 cm, 20 ml )

pH of the elution buffer 7,0 - 9,0
(fractions  -  corrected to  7,0  with conc. phosphoric acid )
0,8 – 2,0 mg/ml
ca. 20 mg

Q Sepharose FF ( śr. 1 cm,  10 ml )
Proteins with a maximum concentration of  4 mg/ml may be yielded
ca. 20 mg

Fig. 22

Fig. 23a (SEQ ID NO: 24)

UBP1ΔC2

```
Gly Gly Phe Ile Ala Gly Leu Val Asn Asp Gly Asn Thr Cys Phe Met
 1           5                  10                  15
Asn Ser Val Leu Gln Ser Leu Ala Ser Ser Arg Glu Leu Met Glu Phe
            20                  25                  30
Leu Asp Asn Asn Val Ile Arg Thr Tyr Glu Glu Ile Glu Gln Asn Glu
            35              40                  45
His Asn Glu Glu Gly Asn Gly Gln Glu Ser Ala Gln Asp Glu Ala Thr
        50              55              60
His Lys Lys Asn Thr Arg Lys Gly Gly Lys Val Tyr Gly Lys His Lys
 65              70                  75                      80
Lys Lys Leu Asn Arg Lys Ser Ser Ser Lys Glu Asp Glu Glu Lys Ser
                85                  90                  95
Gln Glu Pro Asp Ile Thr Phe Ser Val Ala Leu Arg Asp Leu Leu Ser
            100             105                 110
Ala Leu Asn Ala Lys Tyr Tyr Arg Asp Lys Pro Tyr Phe Lys Thr Asn
            115             120                 125
Ser Leu Leu Lys Ala Met Ser Lys Ser Pro Arg Lys Asn Ile Leu Leu
        130             135                 140
Gly Tyr Asp Gln Glu Asp Ala Gln Glu Phe Phe Gln Asn Ile Leu Ala
145             150                 155                     160
Glu Leu Glu Ser Asn Val Lys Ser Leu Asn Thr Glu Lys Leu Asp Thr
                165                 170                 175
Thr Pro Val Ala Lys Ser Glu Leu Pro Asp Asp Ala Leu Val Gly Gln
            180             185                 190
Leu Asn Leu Gly Glu Val Gly Thr Val Tyr Ile Pro Thr Glu Gln Ile
        195             200                 205
Asp Pro Asn Ser Ile Leu His Asp Lys Ser Ile Gln Asn Phe Thr Pro
        210             215                 220
Phe Lys Leu Met Thr Pro Leu Asp Gly Ile Thr Ala Glu Arg Ile Gly
225             230                 235                     240
Cys Leu Gln Cys Gly Glu Asn Gly Gly Ile Arg Tyr Ser Val Phe Ser
            245                 250                 255
Gly Leu Ser Leu Asn Leu Pro Asn Glu Asn Ile Gly Ser Thr Leu Lys
            260                 265                 270
Leu Ser Gln Leu Leu Ser Asp Trp Ser Lys Pro Glu Ile Ile Glu Gly
        275             280                 285
Val Glu Cys Asn Arg Cys Ala Leu Thr Ala Ala His Ser His Leu Phe
        290             295                 300
Gly Gln Leu Lys Glu Phe Glu Lys Lys Pro Glu Gly Ser Ile Pro Glu
305             310                 315                     320
Lys Pro Ile Asn Ala Val Lys Asp Arg Val His Gln Ile Glu Glu Val
                325                 330                 335
Leu Ala Lys Pro Val Ile Asp Asp Glu Asp Tyr Lys Lys Leu His Thr
            340                 345                 350
Ala Asn Met Val Arg Lys Cys Ser Lys Ser Lys Gln Ile Leu Ile Ser
            355                 360                 365
Arg Pro Pro Pro Leu Leu Ser Ile His Ile Asn Arg Ser Val Phe Asp
        370             375                 380
Pro Arg Thr Tyr Met Ile Arg Lys Asn Asn Ser Lys Val Leu Phe Lys
385                 390                 395                 400
Ser Arg Leu Asn Leu Ala Pro Trp Cys Cys Asp Ile Asn Glu Ile Asn
            405             410                 415
Leu Asp Ala Arg Leu Pro Met Ser Lys Lys Glu Lys Ala Ala Gln Gln
            420             425                 430
Asp Ser Ser Glu Asp Glu Asn Ile Gly Gly Glu Tyr Tyr Thr Lys Leu
            435             440                 445
```

```
His Glu Arg Phe Glu Gln Glu Phe Glu Asp Ser Glu Glu Glu Lys Glu
    450                 455                 460
Tyr Asp Asp Ala Glu Gly Asn Tyr Ala Ser His Tyr Asn His Thr Lys
465                 470                 475                 480
Asp Ile Ser Asn Tyr Asp Pro Leu Asn Gly Glu Val Asp Gly Val Thr
                485                 490                 495
Ser Asp Asp Glu Asp Glu Tyr Ile Glu Glu Thr Asp Ala Leu Gly Asn
            500                 505                 510
Thr Ile Lys Lys Arg Ile Ile Glu His Ser Asp Val Glu Asn Glu Asn
        515                 520                 525
Val Lys Asp Asn Glu Glu Leu Gln Glu Ile Asp Asn Val Ser Leu Asp
    530                 535                 540
Glu Pro Lys Ile Asn Val Glu Asp Gln Leu Glu Thr Ser Ser Asp Glu
545                 550                 555                 560
Glu Asp Val Ile Pro Ala Pro Pro Ile Asn Tyr Ala Arg Ser Phe Ser
                565                 570                 575
Thr Val Pro Ala Thr Pro Leu Thr Tyr Ser Leu Arg Ser Val Ile Val
            580                 585                 590
His Tyr Gly Thr His Asn Tyr Gly His Tyr Ile Ala Phe Arg Lys Tyr
        595                 600                 605
Arg Gly Cys Trp Trp Arg Ile Ser Asp Glu Thr Val Tyr Val Val Asp
    610                 615                 620
Glu Ala Glu Val Leu Ser Thr Pro Gly Val Phe Met Leu Phe Tyr Glu
625                 630                 635                 640
Tyr Asp Phe Asp Glu Glu Thr Gly Lys Met Lys Asp Asp Leu Glu Ala
                645                 650                 655
Ile Leu Ser Asn Asn Glu Glu Asp Asp Glu Lys Glu Gln Glu Gln Lys
            660                 665                 670
Gly Val Gln Glu Pro Lys Glu Ser Gln Glu Gln Gly Glu Gly Glu Glu
        675                 680                 685
Gln Glu Glu Gly Gln Glu Gln Met Lys Phe Glu Arg Thr Glu Asp His
    690                 695                 700
Arg Asp Ile Ser Gly Lys Asp Val Asn Gly Ser His His His His His
705                 710                 715                 720
His
```

Fig. 23 b  (SEQ ID NO: 24)

Fig. 24 (SEQ ID NO: 25)

UBP1ΔC

```
Gly Gly Asp His Leu Asn Tyr Ile Val Glu Ser Val Ser Glu Met Thr
1               5                   10                  15
Thr Asn Phe Arg Asn Asn Asn Ser Leu Ser Arg Trp Leu Pro Arg Ser
            20                  25                  30
Lys Phe Thr His Leu Asp Glu Glu Ile Leu Lys Arg Gly Gly Phe Ile
            35                  40                  45
Ala Gly Leu Val Asn Asp Gly Asn Thr Cys Phe Met Asn Ser Val Leu
50                      55                  60
Gln Ser Leu Ala Ser Ser Arg Glu Leu Met Glu Phe Leu Asp Asn Asn
65                  70                  75                  80
Val Ile Arg Thr Tyr Glu Glu Ile Glu Gln Asn Glu His Asn Glu Glu
                85                  90                  95
Gly Asn Gly Gln Glu Ser Ala Gln Asp Glu Ala Thr His Lys Lys Asn
                100                 105                 110
Thr Arg Lys Gly Gly Lys Val Tyr Gly Lys His Lys Lys Lys Leu Asn
            115                 120                 125
Arg Lys Ser Ser Ser Lys Glu Asp Glu Glu Lys Ser Gln Glu Pro Asp
    130                 135                 140
Ile Thr Phe Ser Val Ala Leu Arg Asp Leu Leu Ser Ala Leu Asn Ala
145                 150                 155                 160
Lys Tyr Tyr Arg Asp Lys Pro Tyr Phe Lys Thr Asn Ser Leu Leu Lys
                165                 170                 175
Ala Met Ser Lys Ser Pro Arg Lys Asn Ile Leu Leu Gly Tyr Asp Gln
            180                 185                 190
Glu Asp Ala Gln Glu Phe Phe Gln Asn Ile Leu Ala Glu Leu Glu Ser
        195                 200                 205
Asn Val Lys Ser Leu Asn Thr Glu Lys Leu Asp Thr Thr Pro Val Ala
    210                 215                 220
Lys Ser Glu Leu Pro Asp Asp Ala Leu Val Gly Gln Leu Asn Leu Gly
225                 230                 235                 240
Glu Val Gly Thr Val Tyr Ile Pro Thr Glu Gln Ile Asp Pro Asn Ser
                245                 250                 255
Ile Leu His Asp Lys Ser Ile Gln Asn Phe Thr Pro Phe Lys Leu Met
            260                 265                 270
Thr Pro Leu Asp Gly Ile Thr Ala Glu Arg Ile Gly Cys Leu Gln Cys
        275                 280                 285
Gly Glu Asn Gly Gly Ile Arg Tyr Ser Val Phe Ser Gly Leu Ser Leu
    290                 295                 300
Asn Leu Pro Asn Glu Asn Ile Gly Ser Thr Leu Lys Leu Ser Gln Leu
305                 310                 315                 320
Leu Ser Asp Trp Ser Lys Pro Glu Ile Ile Glu Gly Val Glu Cys Asn
                325                 330                 335
Arg Cys Ala Leu Thr Ala Ala His Ser His Leu Phe Gly Gln Leu Lys
            340                 345                 350
Glu Phe Glu Lys Lys Pro Glu Gly Ser Ile Pro Glu Lys Pro Ile Asn
        355                 360                 365
Ala Val Lys Asp Arg Val His Gln Ile Glu Glu Val Leu Ala Lys Pro
    370                 375                 380
Val Ile Asp Asp Glu Asp Tyr Lys Lys Leu His Thr Ala Asn Met Val
385                 390                 395                 400
Arg Lys Cys Ser Lys Ser Lys Gln Ile Leu Ile Ser Arg Pro Pro Pro
                405                 410                 415
Leu Leu Ser Ile His Ile Asn Arg Ser Val Phe Asp Pro Arg Thr Tyr
            420                 425                 430
Met Ile Arg Lys Asn Asn Ser Lys Val Leu Phe Lys Ser Arg Leu Asn
        435                 440                 445
Leu Ala Pro Trp Cys Cys Asp Ile Asn Glu Ile Asn Leu Asp Ala Arg
450                 455                 460
```

| | | | | | | | | | | | | | | | |
|---|---|---|---|---|---|---|---|---|---|---|---|---|---|---|---|
| Leu | Pro | Met | Ser | Lys | Lys | Glu | Lys | Ala | Ala | Gln | Gln | Asp | Ser | Ser | Glu |
| 465 | | | | | 470 | | | | | 475 | | | | | 480 |
| Asp | Glu | Asn | Ile | Gly | Gly | Glu | Tyr | Tyr | Thr | Lys | Leu | His | Glu | Arg | Phe |
| | | | | 485 | | | | | 490 | | | | | 495 | |
| Glu | Gln | Glu | Phe | Glu | Asp | Ser | Glu | Glu | Lys | Glu | Tyr | Asp | Asp | Ala | |
| | | | 500 | | | | | 505 | | | | 510 | | | |
| Glu | Gly | Asn | Tyr | Ala | Ser | His | Tyr | Asn | His | Thr | Lys | Asp | Ile | Ser | Asn |
| | | 515 | | | | | 520 | | | | | 525 | | | |
| Tyr | Asp | Pro | Leu | Asn | Gly | Glu | Val | Asp | Gly | Val | Thr | Ser | Asp | Asp | Glu |
| | 530 | | | | | 535 | | | | | 540 | | | | |
| Asp | Glu | Tyr | Ile | Glu | Glu | Thr | Asp | Ala | Leu | Gly | Asn | Thr | Ile | Lys | Lys |
| 545 | | | | | 550 | | | | | 555 | | | | | 560 |
| Arg | Ile | Ile | Glu | His | Ser | Asp | Val | Glu | Asn | Glu | Asn | Val | Lys | Asp | Asn |
| | | | | 565 | | | | | 570 | | | | | 575 | |
| Glu | Glu | Leu | Gln | Glu | Ile | Asp | Asn | Val | Ser | Leu | Asp | Glu | Pro | Lys | Ile |
| | | | 580 | | | | | 585 | | | | | 590 | | |
| Asn | Val | Glu | Asp | Gln | Leu | Glu | Thr | Ser | Ser | Asp | Glu | Glu | Asp | Val | Ile |
| | | 595 | | | | | 600 | | | | | 605 | | | |
| Pro | Ala | Pro | Pro | Ile | Asn | Tyr | Ala | Arg | Ser | Phe | Ser | Thr | Val | Pro | Ala |
| | 610 | | | | | 615 | | | | | 620 | | | | |
| Thr | Pro | Leu | Thr | Tyr | Ser | Leu | Arg | Ser | Val | Ile | Val | His | Tyr | Gly | Thr |
| 625 | | | | | 630 | | | | | 635 | | | | | 640 |
| His | Asn | Tyr | Gly | His | Tyr | Ile | Ala | Phe | Arg | Lys | Tyr | Arg | Gly | Cys | Trp |
| | | | | 645 | | | | | 650 | | | | | 655 | |
| Trp | Arg | Ile | Ser | Asp | Glu | Thr | Val | Tyr | Val | Val | Asp | Glu | Ala | Glu | Val |
| | | | 660 | | | | | 665 | | | | | 670 | | |
| Leu | Ser | Thr | Pro | Gly | Val | Phe | Met | Leu | Phe | Tyr | Glu | Tyr | Asp | Phe | Asp |
| | | 675 | | | | | 680 | | | | | 685 | | | |
| Glu | Glu | Thr | Gly | Lys | Met | Lys | Asp | Asp | Leu | Glu | Ala | Ile | Leu | Ser | Asn |
| | | 690 | | | | | 695 | | | | | 700 | | | |
| Asn | Glu | Glu | Asp | Asp | Glu | Lys | Glu | Gln | Glu | Gln | Lys | Gly | Val | Gln | Glu |
| 705 | | | | | 710 | | | | | 715 | | | | | 720 |
| Pro | Lys | Glu | Ser | Gln | Glu | Gln | Gly | Glu | Gly | Glu | Glu | Gln | Glu | Glu | Gly |
| | | | | 725 | | | | | 730 | | | | | 735 | |
| Gln | Glu | Gln | Met | Lys | Phe | Glu | Arg | Thr | Glu | Asp | His | Arg | Asp | Ile | Ser |
| | | | 740 | | | | | 745 | | | | | 750 | | |
| Gly | Lys | Asp | Val | Asn | Gly | Ser | His | His | His | His | His | | | | |
| | | 755 | | | | | 760 | | | | | 765 | | | |

Fig. 24b    (SEQ ID NO: 25)

Fig. 25 (SEQ ID NO: 26)

```
atg caa att ttt gtt aaa act tta act ggt aaa acc att acc tta gaa    48
Met Gln Ile Phe Val Lys Thr Leu Thr Gly Lys Thr Ile Thr Leu Glu
1               5                   10                  15
gtt gaa tct tca gat acc att gat aat gtt aaa tct aaa att caa gat    96
Val Glu Ser Ser Asp Thr Ile Asp Asn Val Lys Ser Lys Ile Gln Asp
                20                  25                  30
aaa gaa ggt att cct cca gat caa caa cgt cta ata ttt gca ggt aaa   144
Lys Glu Gly Ile Pro Pro Asp Gln Gln Arg Leu Ile Phe Ala Gly Lys
            35                  40                  45
cag tta gaa gat ggt cgt acc ctg tct gat tat aac att cag aaa gaa   192
Gln Leu Glu Asp Gly Arg Thr Leu Ser Asp Tyr Asn Ile Gln Lys Glu
        50                  55                  60
tct acc tta cat ctg gtc tta cgt ctc cgc ggt ggt ttc cca acc att   240
Ser Thr Leu His Leu Val Leu Arg Leu Arg Gly Gly Phe Pro Thr Ile
65                  70                  75                  80
ccc tta agt agg ctt ttt gac aac gct atg ctc cgc gcc cat cgt ctg   288
Pro Leu Ser Arg Leu Phe Asp Asn Ala Met Leu Arg Ala His Arg Leu
                85                  90                  95
cac cag ctg gcc ttt gac acc tac cag gag ttt gaa gaa gct tat atc   336
His Gln Leu Ala Phe Asp Thr Tyr Gln Glu Phe Glu Glu Ala Tyr Ile
            100                 105                 110
cca aag gaa cag aag tat tca ttc ctg cag aac ccc cag acc tcc ctc   384
Pro Lys Glu Gln Lys Tyr Ser Phe Leu Gln Asn Pro Gln Thr Ser Leu
        115                 120                 125
tgt ttc tca gag tct att ccg aca ccc tcc aac agg gag gaa aca caa   432
Cys Phe Ser Glu Ser Ile Pro Thr Pro Ser Asn Arg Glu Glu Thr Gln
130                 135                 140
cag aaa tcc aac ctc gag ctg ctc cgc atc tcc ctg ctc atc cag       480
Gln Lys Ser Asn Leu Glu Leu Leu Arg Ile Ser Leu Leu Leu Ile Gln
145                 150                 155                 160
tcg tgg ctg gag ccc gtg cag ttc ctc agg agt gtc ttc gcc aac agc   528
Ser Trp Leu Glu Pro Val Gln Phe Leu Arg Ser Val Phe Ala Asn Ser
                165                 170                 175
ctg gtg tac ggc gcc tct gac agc aac gtc tat gac ctc cta aag gac   576
Leu Val Tyr Gly Ala Ser Asp Ser Asn Val Tyr Asp Leu Leu Lys Asp
            180                 185                 190
cta gag gaa ggg atc caa acg ctg atg ggg agg ctg gaa gat ggc agc   624
Leu Glu Glu Gly Ile Gln Thr Leu Met Gly Arg Leu Glu Asp Gly Ser
        195                 200                 205
ccc cgg act ggg cag atc ttc aag cag acc tac agc aag ttc gac aca   672
Pro Arg Thr Gly Gln Ile Phe Lys Gln Thr Tyr Ser Lys Phe Asp Thr
210                 215                 220
aac tca cac aac gat gac gca cta ctc aag aac tac ggg ctg ctc tac   720
Asn Ser His Asn Asp Asp Ala Leu Leu Lys Asn Tyr Gly Leu Leu Tyr
225                 230                 235                 240
tgc ttc agg aag gac atg gac aag gtc gag aca ttc ctg cgc atc gtg   768
Cys Phe Arg Lys Asp Met Asp Lys Val Glu Thr Phe Leu Arg Ile Val
                245                 250                 255
cag tgc cgc tct gtg gag ggc agc tgt ggc ttc taa                   804
Gln Cys Arg Ser Val Glu Gly Ser Cys Gly Phe
            260                 265
```

METHOD FOR PRODUCTION OF RECOMBINANT GROWTH HORMONE IN FORM OF HYBRID PROTEIN

RELATED APPLICATIONS

This is a continuation-in-part of and claims benefit under 35 U.S.C. §120 International Patent Application No. PCT/PL2005/000003 filed on Jan. 10, 2005, which claims priority under 35 U.S.C. §119 to Polish Application No. P.364295 filed on Jan. 9, 2004 the teachings of both applications are incorporated in their entirety by reference.

BACKGROUND OF THE INVENTION

Human growth hormone ("hGH") also known as somatotropin consists of 191 amino acids with a molecular mass of 22 kDa, with two disulfide bridges between the chains, which is synthesized and secreted by cells called somatotrophs in the anterior pituitary. Growth hormone is produced in the anterior lobe or in the glandular portion of the pituitary during the entire life of an individual, in largest quantities during puberty. It is synthesized as a precursor, and released into the blood following modifications. Human growth hormone is used in the treatment of certain forms of dwarfism caused by its deficiencies, in obesity therapy and in wound and burn treatment. Due to the fact that only human growth hormone can be used in the treatment of growth abnormalities, a large demand exists for this compound.

Until recently, the only source of hGH were cadaver pituitaries, whose hormone was isolated using time consuming and complicated technologies. The efficiency of producing hGH from pituitaries is very low, since only 2-3 mg of hormone are obtained from one gland. recently, a series of methods have been designed to by pass this system. In U.S. Pat. No. 4,124,448, a method was described of producing hGH on a large scale through culturing human pituitary cells in a liquid culture. In the patent described, a 20-fold efficiency is obtained per pituitary, when compared to the extraction from autopsy glands. A significant reason to search for other methods of obtaining human growth hormone is that the administration of somatotropin from human pituitaries (the material came from, among others, Africa) bears a risk of infection with various incurable diseases such as Creutzfeldt-Jakob disease or AIDS.

Methods exist for producing hGH through fermentation using organisms transformed using DNA recombination.

Improved recombinant production of hGH and methods of purification thereof are detailed in U.S. Pat. Nos. 4,534,258; 4,898,830; 5,424,199; and 5,795,745.

A variety of bacterial hGH expression methods using conventional fermentation and induction conditions have been proposed in the art.

Attempts to bacterially express human and bovine somatotropin in non-secretion systems using structural genes having the sequences of their cDNAs were successful after introducing silent mutations into the front end of the structural gene attributed the original difficulties to translation being impeded by the secondary structure of the mRNA corresponding to the cDNA, and taught lessening such secondary structure to enable significant expression. DNA, Vol. 2, No. 1, 1983, pp. 37-45; U.S. Pat. Nos. 5,254,463 and 5,260,201.

EP1400593 describes a method of producing human growth hormone or a salt thereof, which comprises culturing the transformant *Escherichia coli* mM294/pNP3GHNO12 (FERM BP-7611). A promoter of the transformant has a novel nucleotide sequence between any −35 region sequence and any −10 region sequence. The promoter has a strong promoter activity and thus a target peptide or protein can be produced at a high efficiency and in large amounts through linking the structural gene encoding the target peptide or protein downstream of the promoter. Another mode of use of *E. coli* host cell for expression of the gene for somatotropin protein was proposed in EP0418219B1. The invention involves to *E. coli* host cell comprising a mutation of the rpoH or hflB gene and a plasmid consisting of a mutant R1 replicon from pBEU-17 or pBEU-50, an origin of replication from pBR322, and cDNA encoding the heterologous protein. WO9726334A1 provides methods for the production of heterologous polypeptides including human growth hormone, using a variety of recombinantly engineered mammalian secretory cell lines and blocking expression of native sequence and replacing with a construct giving improved secretion, useful to treat, e.g. diabetes.

An alternative approach for somatotropin production involves obtaining inclusion bodies. US20030229210A1 discloses a process for the preparation of active somatotropin from inclusion bodies of a recombinant host cell containing an inactive form of said somatotropin protein. The process comprises: contacting the inclusion bodies with an aqueous alcohol solution to solubilize said protein and bringing the solubilized protein into contact with a mild oxidizing agent to refold and form intramolecular disulfide bonds between cysteine residues of said protein.

Cleaval trials have been made to provide increased conformational and chemical stability of somatotropin. WO 94/10200 suggests a number of amino acid substitutions in somatotropin. Alterations of these characteristics are obtained via modification of somatotropins by site-directed mutagenesis.

As to purification of the growth hormone, methods for purifying and recovering biologically active somatotropin monomers from refold solution involve the solubilization and naturation of refractile bodies of host cells produced by recombinant DNA methodology. The purification process is based on the discovery that somatotropin monomers and somatotropin oligomers having overlapping isoelectric points may nevertheless be separated by selective precipitation over a narrow pH range (U.S. Pat. Nos. 5,182,369, 5,773, 588).

Despite significant progress made in this area over the last few years, production of recombinant human growth hormone through expression in cellular expression systems is still in need of perfection. The main problems in need of resolution are to increase the overall efficiency of the whole process, as well as designing a method of increasing the stability of the protein produced. Growth hormone is a protein sensitive to factors which occur during its production and purification, which makes it difficult to produce and causes great losses in the amounts of active protein produced.

In biotechnology, the most useful vectors are the so-called expression vectors, which facilitate efficient synthesis of proteins encoded by the genes contained on the vector. Such vectors bear promoter sequences which facilitate transcription and translation, and sequences ensuring the stability of the synthesized protein. There are expression vectors under the control of strong promoters, whose synthesis can lead to accumulations of a given protein totaling 30% or even more of total cellular protein. Such vectors have been used for years in the production of many well known and useful proteins, particularly ones with desirable pharmacological properties. It is particularly desirable to provide new plasmids which could be used to produce new constructs useful in microbiological production of growth hormone, especially ones facilitating stable or regulated expression thereof. In this context it is particularly desirable to provide autonomic functional elements which could be used in the production of other useful constructs. For example, it is still desirable to produce transcription regulatory elements, like strong transcriptional promoters.

Protease UBP1 is an enzyme isolated from yeast, which cleaves ubiquitin from proteins fused to its C-end. The enzyme was described in 1991 (J. Tobias, A. Varshavsky, J. Biol. Chem. 1991, 266; 12021-12028) and is the subject of the patent application WO91/17245 (European patent EP 531 404). Its activity and culture conditions were described in *E. coli*. In accordance to the contents of the description, it is a cysteine protease, which binds ubiquitin with an ester bond during the course of the reaction. UBP1 is 809 amino-acids long. The enzyme's activity is dependent on its ability to cleave the ubiquitin peptide from a polypeptide fused to its C-end, regardless of the amino-acid sequence of the N-end of the polypeptide being digested off.

Application No. WO93/09235 describes other yeast proteins belonging to the same family of proteases, namely UBP2 and UBP3. These proteins exhibit similar activity (see also U.S. Pat. Nos. 5,494,818, 5,212,058, 5,683,904).

There are expression systems known, in which fusion proteins are obtained composed of ubiquitin or its derivative and a polypeptide of interest, and then, using a ubiquitin-removing enzyme (eg. UBP1) the protein of interest is recovered (for examples see: U.S. Pat. Nos. 5,132,213, 6,018,102). This method has many advantages such as improved quality and efficiency of obtaining the protein, as well as simplification of purification, which is of great importance in the industrial production of recombinant proteins (for example see: WO03/010204). Using an enzyme which removes ubiquitin and appropriate fusion proteins one may also obtain N-terminally modified polypeptides (for example: U.S. Pat. No. 5,847,097).

The international submission published as WO 2004/097011 describes UBP1 protease deletion mutants, containing a deletion of at least a portion of the initial 54 amino-acids from the amino-acid sequence of the UBP1 protease, and also describes some point mutations, which improve the expression level of such a protease in microbiological expression systems.

The application of an enzyme which removes ubiquitin in technological processes requires large amounts of this protein, which should also exhibit the maximal proteolytic activity level. A majority of known methods do not facilitate the efficient expression of this enzyme, which has greatly limited its applicability, especially in industrial processes. The purity and activity of the enzyme are important, if it is to be used in a subsequent stage of the production of a particular protein, particularly human growth hormone protein. Despite the solutions presented in WO 2004/097011, there is still a need to obtain a protein for cleaving UBP1, which could be produced in an efficient manner, for example through the expression in known microbiological systems, which protein would also exhibit improved specific proteolytic activity characteristics.

To summarise, it should be stated that the goal of the present invention is to propose an efficient method of obtaining human growth hormone human growth hormone by way of expression in bacterial cells, particularly in *E. coli*. Such a method should facilitate the production of relatively large quantities of protein of appropriate quality and activity for its application in the production of pharmaceutical preparations.

In particular, it is desirable to produce tools necessary to carry out such a method, especially efficient expression promoters, vectors containing them, as well as other tools such as enzymes, which are essential to the production of growth hormone through expression in a bacterial cell, encompassing the production of a large amount of stable fusion protein.

Therefore, a particular goal of the present invention is to also deliver a new, improved ubiquitin-cleaving enzyme cleaving ubiquitin, which would also be characterised by improved specific proteolytic activity, and which could be successfully used in the industrial production of growth hormone expressed in bacterial cells as fusion proteins with ubiquitin.

The next goal of the present invention is to propose the subsequent stages of the production of growth hormone, particularly renaturation conditions and purification of the protein produced.

SUMMARY OF THE PRESENT INVENTION

The subject of the present invention is a method of producing somatotropin encompassing the microbiological expression of a recombinant protein containing somatotropin, characterised in that it encompasses:

(a) production of a hybrid polypeptide composed of polypeptide containing the amino-acid sequence of ubiquitin and a polypeptide containing the amino-acid sequence of somatotropin through such treatment of bacterial cells containing hybrid polypeptide DNA that the hybrid polypeptide is expressed;

(b) reclamation of the hybrid polypeptide;

(c) digestion of the hybrid polypeptide obtained with an ubiquitin-cleaving enzyme, (d) purification of thusly produced somatotropin.

Due to the difficulty of expressing the human growth hormone gene in bacteria, the plasmid was designed in such a way that the protein product coded for by an appropriate gene is a fusion protein, ubiquitin:somatotropin, which favourably influences the level of the heterologous protein.

In a preferential embodiment of a method according to present invention, stage (a) encompasses the culturing of *E. coli* cells transformed with a plasmid selected from among: pIGALUH (SEQ ID NO: 21) (FIGS. 11 and 12), pIGALUHM (SEQ ID NO: 22) (FIGS. 13 and 14), pIGDMKUH (SEQ ID NO: 23) (FIGS. 15 and 16), pIGRKKhGH (SEQ ID NO: 20) (FIGS. 9 and 10), pIGMS31PRH (SEQ ID NO: 18) (FIGS. 4 and 5), where it is preferential that the host cell be the *E. coli* DH5a strain.

In accordance with the preferential embodiment of a method according to present invention, reclamation in stage (b) encompasses:

(i) destruction of the bacterial cell wall or its fragments in order to form the lysate;

(ii) isolation of inclusion bodies from the lysate through centrifugation; and (iii) dissolution of the inclusion bodies.

In a particular embodiment of this form of the present invention, the isolation of inclusion bodies takes place in the presence of 25% glycerol, whereas the dissolution of the inclusion bodies may take place under denaturing conditions, preferentially in the presence of urea. For example, the dissolution of inclusion bodies may take place in a buffer, pH ca. 12 containing 6-8 M urea and 5 mM beta-mercaptoethanol.

In a preferential embodiment of a method according to the present invention stage (b) also encompasses purification through chromatography on DEAE-Sepharose, preferentially in the presence of 6-8 M urea and pH 7.0.

In a preferential embodiment of a method according to the present invention stage (b) also encompasses purification through chromatography on SP-Sepharose FF, preferentially in the presence of 6-8 M urea and pH 7.0.

In a preferential embodiment of a method according to the present invention stage (b) also encompasses the incubation of the hybrid polypeptide at a temperature of 4-24° C. over a period of 0.5-5 h at a pH of ca. 6.5-8.0, preferentially over ca. 1 h in a renaturation buffer 20 mM phosphate buffer, pH 7-8 and 50 mM NaCl, wherein the protein concentration in solution is about 0.1 mg/ml solution.

In a preferential embodiment of a method according to the present invention stage (b) also encompasses the production of a concentrated solution of the hybrid polypeptide through the precipitation of the hybrid polypeptide with ammonium sulphate, where it is preferential that the precipitation is performed up to 80% saturation with ammonium sulphate, centrifugation and resuspension of the hybrid polypeptide in a decreased amount of phosphate buffer with pH 7, containing 500 mM NaCl.

In a preferential embodiment of a method according to the present invention stage (c) encompasses:
(i) adjustment of pH to ca. 7-8, and
(ii) digestion of the hybrid polypeptide with an ubiquitin-cleaving enzyme at a temperature of ca. 37° C. over 30 min to 3 h, where the enzyme cleaving off the ubiquitin is contained in yeast extract or is the yeast protease UBP1 or its mutant, where in a particularly preferential embodiment of the present invention, the UBP1 protease mutant contains an amino-acid sequence containing at least one from among the following modifications:
  a substitution at position 754 of the UBP1 amino-acid sequence,
  a deletion of at least a portion of the amino-acids at positions 1 to 98 of the UBP1 sequence,
  replacement of the proline at position 415 of the UBP1 sequence with leucine,
  replacement of the phenylalanine at position 739 of the UBP1 sequence with leucine,
  fusion of the ubiquitin polypeptide to the N-terminal amino-acid with a peptide bond,
  fusion of a marker amino-acid sequence to the C-terminal amino-acid with a peptide bond, facilitating the isolation of a polypeptide containing it, particularly using affinity chromatography. The sequences of example UBP1 mutants are presented in FIG. 23 (SEQ ID NO: 24) and FIG. 24 (SEQ ID NO: 25), where UBP1ΔC2 (SEQ ID NO: 24) or UBP1ΔC (SEQ ID NO: 25) are particularly preferential.

In a preferential embodiment of a method according to the present invention stage (d) encompasses the separation of the protein mixture through chromatography on the hydrophobic carrier Phenylo-Sepharose FF and collection of the fraction containing somatotropin, where the column is preferentially equilibrated with 20 mM phosphate buffer, pH 7 containing 0.5 M NaCl, and protein elution is performed with 3-5 mM phosphate buffer, pH 7 to 9.

In a preferential embodiment of a method according to the present invention stage (d) also encompasses further somatotropin purification through chromatography on the anionic carrier Q-Sepharose FF and collection of the fractions containing somatotropin, where the column is preferentially equilibrated with 20 mM phosphate buffer, pH 7.5 and the elution is performed using a NaCl concentration gradient in phosphate buffer, pH 7.5 where the somatotrophin is eluted at a NaCl concentration of 0.25 M.

The next subject of the present invention is a hybrid polypeptide containing the amino-acid sequence of ubiquitin and the amino-acid sequence of somatotropin.

In a preferential embodiment of this aspect of the present invention, a sequence containing the amino-acid sequence of ubiquitin is fused to the N-end of the amino-acid sequence of somatotropin, which in a particularly preferential embodiment is coded by the sequence represented in FIG. 1 SEQ ID NO: 13 and 14.

Example preferential hybrid polypeptids according to the present invention are coded by the hybrid polypeptide gene contained in a plasmid selected from among: pIGALUH (SEQ ID NO: 21) (FIGS. 11 and 12), pIGALUHM (SEQ ID NO: 22) (FIGS. 13 and 14), pIGDMKUH (SEQ ID NO: 23) (FIGS. 15 and 16), pIGRKKhGH (SEQ ID NO: 20) (FIGS. 9 and 10), pIGMS31PRH (SEQ ID NO: 18) (FIGS. 4 and 5). Preferentially, the hybrid polypeptide according to the present invention contains one of the sequences presented in FIG. 25 (SEQ ID NO: 26).

To better illustrate the content of the description, it has been supplemented with figures.

BRIEF DESCRIPTION OF THE DRAWINGS

FIG. 1 represents the nucleotide and amino-acid sequences of the synthetic ubiquitin gene as well as the oligonucleotide sequences used in the production of the gene.

FIG. 2: the nucleotide and amino-acid sequences of the growth hormone gene.

FIG. 3: the nucleotide of the pms promoter.

FIG. 4 and FIG. 5 represent the restriction map and nucleotide sequence respectively of the plasmid pIGMS31PRH (SEQ ID NO: 18). FIG. 5(a) is the first portion of the SEQ ID NO:18 and FIG. 5(b) is the second portion of SEQ ID NO:18. Together the sequences of FIGS. 5(a) and 5(b) represent the entire sequence of SEQ ID NO:18.

FIG. 7 and FIG. 8 represent the restriction map and nucleotide sequence respectively of the plasmid vector pIGRK-KAN (SEQ ID NO: 19). The immunogenic sequences imm1 and imm2 have been indicated on the map. Nucleotides 1169 to 1199 encompass a multicloning site. Arrows indicate open reading frames for proteins coded by the plasmid. The frame located between nucleotides 147 and 962 codes for an aminoglycoside phosphotransferase, a protein involved in kanamycin resistance. The functions of the remaining open reading frames are unknown. FIG. 8(a) is the first portion of the SEQ ID NO:19 and FIG. 8(b) is the second portion of SEQ ID NO:19. Together the sequences of FIGS. 8(a) and 8(b) represent the entire sequence of SEQ ID NO:19.

FIG. 9 and FIG. 10 represent the restriction map and nucleotide sequence respectively of the expression vector pIGRKKhGH (SEQ ID NO: 20). FIG. 10(a) is the first portion of the SEQ ID NO:20, FIG. 10(b) is the second portion of SEQ ID NO:20 and FIG. 10(c) is the third portion of SEQ ID NO:20. Together the sequences of FIGS. 10(a), 10(b) and 10(c) represent the entire sequence of SEQ ID NO:20. FIG. 11 and FIG. 12 represent the restriction map and nucleotide sequence respectively of the expression vector pIGALUH (SEQ ID NO: 21). FIG. 12(a) is the first portion of the SEQ ID NO:21, and FIG. 12(b) is the second portion of SEQ ID NO:21. Together the sequences of FIGS. 12(a), and 12(b) represent the entire sequence of SEQ ID NO:21.

FIG. 13 and FIG. 14 represent the restriction map and nucleotide sequence respectively of the expression vector pIGALUHM (SEQ ID NO: 22). FIG. 14(a) is the first portion of the SEQ ID NO:22, and FIG. 14(b) is the second portion of SEQ ID NO:22. Together the sequences of FIGS. 14(a), and 14(b) represent the entire sequence of SEQ ID NO:22.

FIG. 15 and FIG. 16 represent the restriction map and nucleotide sequence respectively of the expression vector pIGDMKUH (SEQ ID NO: 23). FIG. 16(a) is the first portion of the SEQ ID NO:23, and FIG. 16(b) is the second portion of SEQ ID NO:23. Together the sequences of FIGS. 16(a), and 16(b) represent the entire sequence of SEQ ID NO:23.

FIG. 22 represents an example schematic of stages according to a method according to the present invention which encompasses purification of growth hormone; example values of selected parameters of the process are given, as are concentration values of the purified protein.

FIGS. 23(a) and 23(b) show the UBP1 mutant UBP1ΔC2 (SEQ ID NO: 24) and FIGS. 24 and 24(b) show the UBP1 mutant UBP1ΔC (SEQ ID NO: 25). FIG. 23(a) is the first portion of SEQ ID NO:24, and FIG. 23(b) is the second portion of SEQ ID NO:24. Together the sequences of FIGS. 23(a), and 23(b) represent the entire sequence of SEQ ID NO:24. FIG. 24 is the first portion of SEQ ID NO:25, and FIG. 24(b) is the second portion of SEQ ID NO:25. Together the sequences of FIGS. 24, and 24(b) represent the entire sequence of SEQ ID NO:25.

Figure 4:
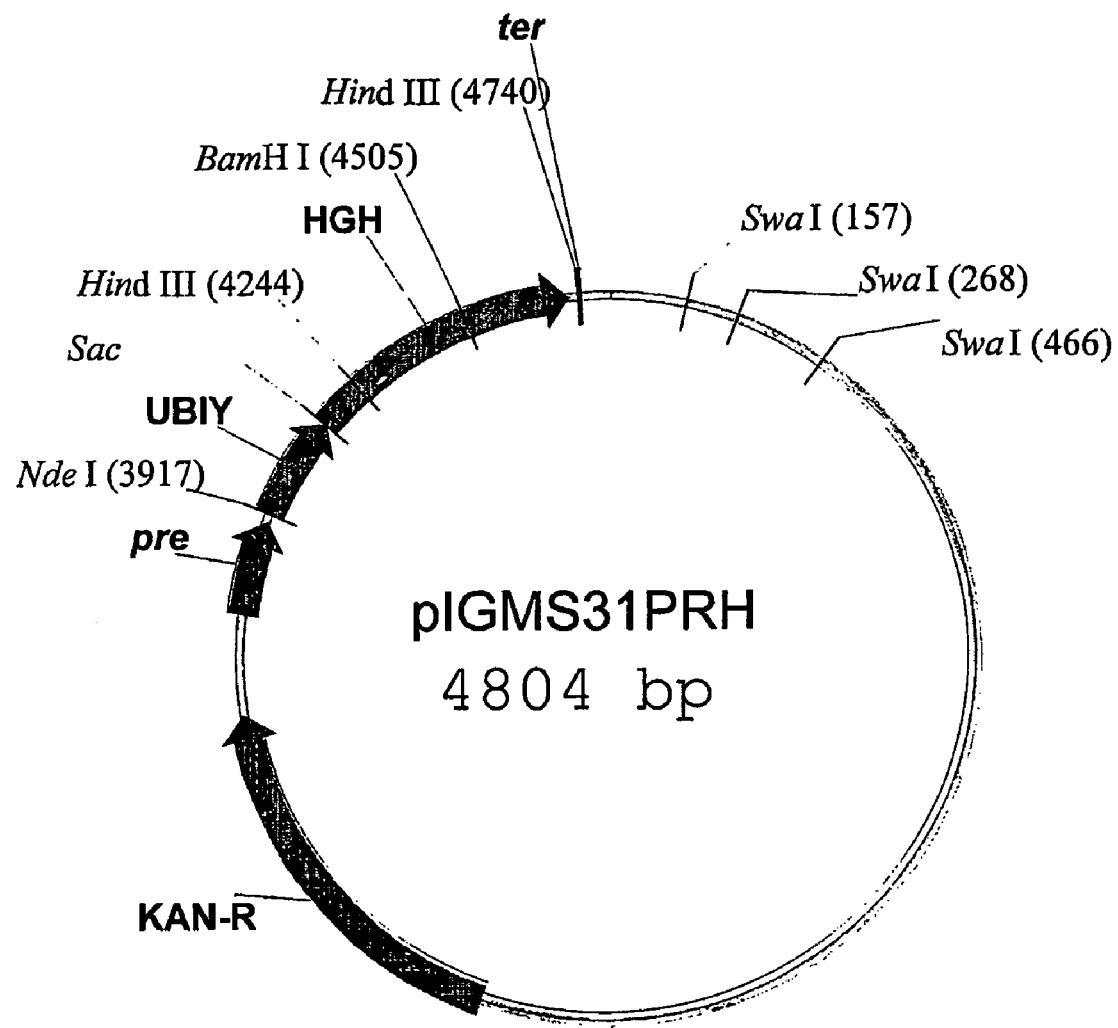

The following examples are only meant to present assorted embodiments of the present invention and should not be viewed as the whole of its scope.

EXAMPLE 1

Construction of Plasmids Coding the Fusion Protein Ubiquitin-growth Hormone; Elements Useful in the Construction of Such Plasmids The ubiquitin gene, 253 base pairs long, was obtained from synthetic DNA fragments.

Gene fragments were designed in accordance with the codon frequency E. coli with gaps in the lower 3'-5'strand. (FIG. 1)

The synthetic DNA fragments UBIS2 (SEQ ID NO: 2), UBI3P (SEQ ID NO: 3), UBI4P (SEQ ID NO:4), UBI5P (SEQ ID NO: 5) and UBIS6 (SEQ ID NO: 6) were treated with kinase for an hour at 37° C.

Next, complementary strand fragments were added: UBIS12 (SEQ ID NO: 7), UBI23P (SEQ ID NO: 8), UBI34P (SEQ ID NO: 9), UBI54P (SEQ ID NO: 10), UBIS56 (SEQ ID NO: 11) and UBIS1 (SEQ ID NO: 12) and ligation took place overnight at 16° C.

Using PCR, the DNA fragments were amplified and joined together. The renaturation and annealing temperature was 72° C.

The fragment obtained was eluted from the gel. It was digested with the EcoRI and SalI restrictases, in 50 μl for one hour at 37° C.

Following the digestion, the fragment was ligated with the pUC19, treated with the same enzymes, and transformed into E. coli NM 522.

Clones were obtained containing the recombinant NUbi-pUC19, which were analysed with the EcoRI and HindIII restrictases.

Sequencing was performed to ascertain the correctness of the nucleotide sequence of the synthetic ubiquitin gene.

FIG. 2 (SEQ ID NO: 15) represents the nucleotide and amino-acid sequences of the growth hormone gene. FIG. 25 (SEQ ID NO: 26) represents example of a hybrid polypeptide according to the invention.

The PMS Promoter

Bacterial expression vectors were constructed under the control of the very efficient pms promoter which produce large amounts of hybrid proteins in E. coli. This promoter was isolated from a plasmid found in a wild-type strain of Klebsiella pneumoniae (GenBank Accession No AY543071). The nucleotide sequence of the constitutive transcription promoter is represented in FIG. 3 (SEQ ID NO: 17). The region of plasmid pIGRKKAN (SEQ ID NO: 19) (see below) contained between nucleotides 1240 and 1367 was transferred to the polylinker sequence of plasmid pIGMS31KAN (see below). The gene coding the ubiquitin and human growth factor fusion protein and transcription terminator was placed downstream of this sequence. Electrophoretic analysis of cell lysates of E. coli DH5α cells transformed with this plasmid indicated the presence of considerable quantities of a protein corresponding in size to the fusion protein. This means that the region of plasmid pIGRKKAN (SEQ ID NO: 19) contained between nucleotides 1240 and 1367 contains a sequence which functions as a very efficient transcription promoter. The region described contains the polypurine (AG-GAGG) (SEQ ID NO: 28) Shine-Dalgarno sequence between nucleotides 1356-1361 in close proximity to the ATG codon at the start of one of the reading frames in plasmid pIGRKAN. The sequence of the identified promoter has been called pms.

Plasmid pIGMS31KAN

The promoter sequence of retron Ec86 and its following transcription terminator sequence [Lim D., Maas W. K. (1989), Cell 56, 891-904] were inserted into plasmid pIGMS31KAN. The plasmid formed was designated pIGMS31PR. Plasmid pIGMS31PR was used to clone a gene coding a fusion protein composed of yeast ubiquitin and human growth hormone.

Figure 6:
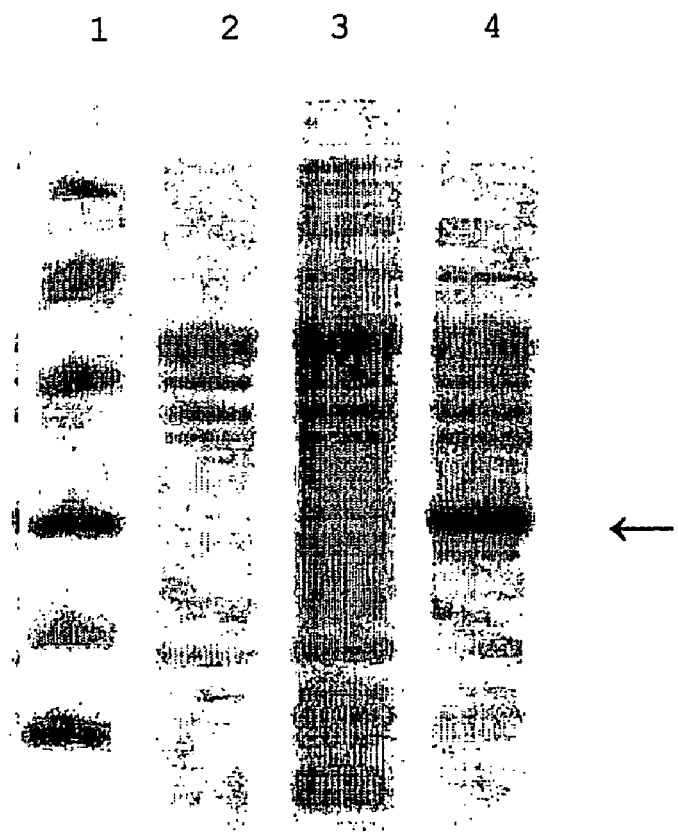
FIG. 6 represents the electrophoretic analysis of cell lysates in a 15% polyacrylamide gel. 1. molecular mass marker (97.0, 66.0, 45.0, 30.0 20.1 14.4 kDa). 2. Host strain E. coli. DH5α. 3. The E. coli DH5α strain transformed with plasmid pIGMS31PR. 4. The E. coli DH5α strain transformed with plasmid pIGMS31PRH (SEQ ID NO: 18). The arrow indicates the location of the fusion protein.

Plasmid pIGMS31PRH (SEQ ID NO: 18) is 4804 base pairs long and contains the following sequences:
- a kanamycin resistance gene (KAN-R) at 2669-3484 bp
- promoter of retron Ec86 (pre) at 3699-3898 bp
- a sequence coding yeast ubiquitin (UBIY) at 3918-4145 bp
- a sequence coding human growth hormone (HGH) at 4146-4721 bp
- a sequence coding a transcription terminator (ter) at 4746-4764 bp The full sequence of the derivative plasmid, pIGMS31PRH (SEQ ID NO: 18) is presented in FIGS. 4 and 5. The plasmid was used to transform cells of E. coli strain DH5α. Electrophoretic analysis of cell lysates showed the presence of a protein of a size corresponding to the fusion protein ubiquitin-growth hormone (FIG. 6)

Plasmid pIGRKKAN (SEQ ID NO: 19)

Figure 7:
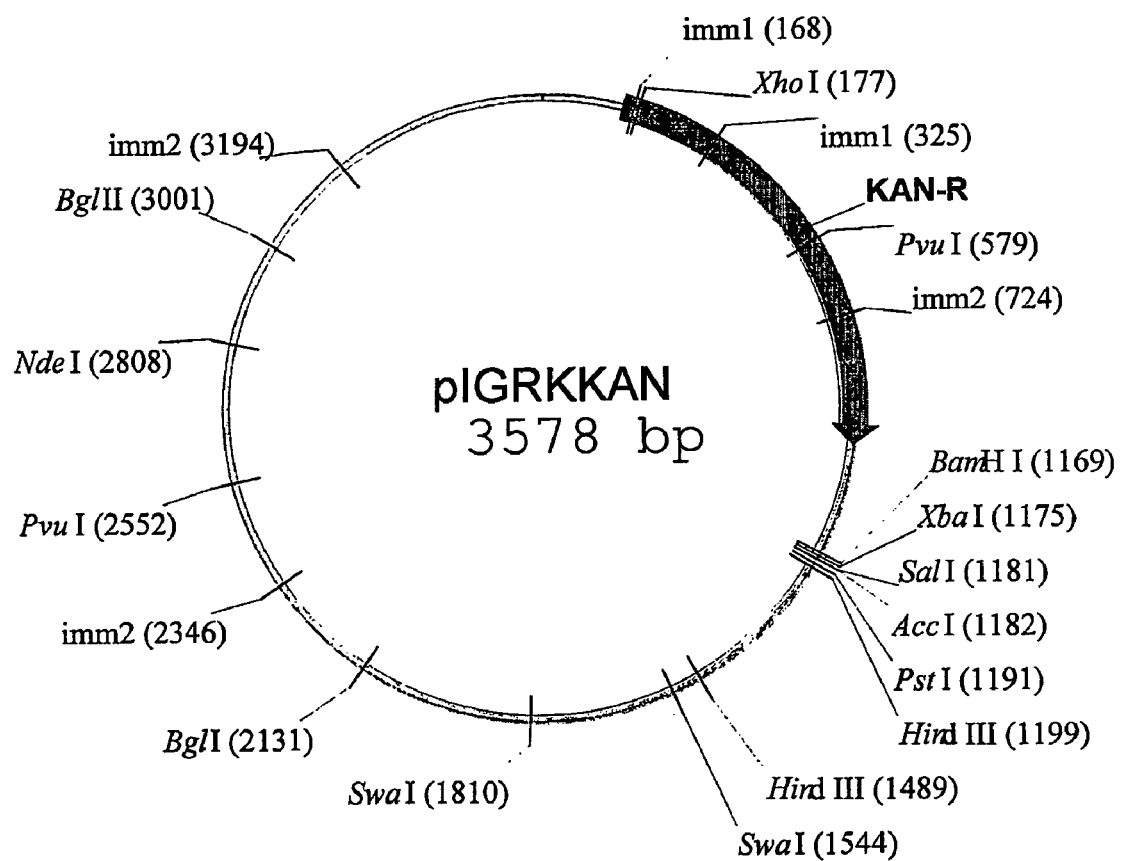
Figure 9:
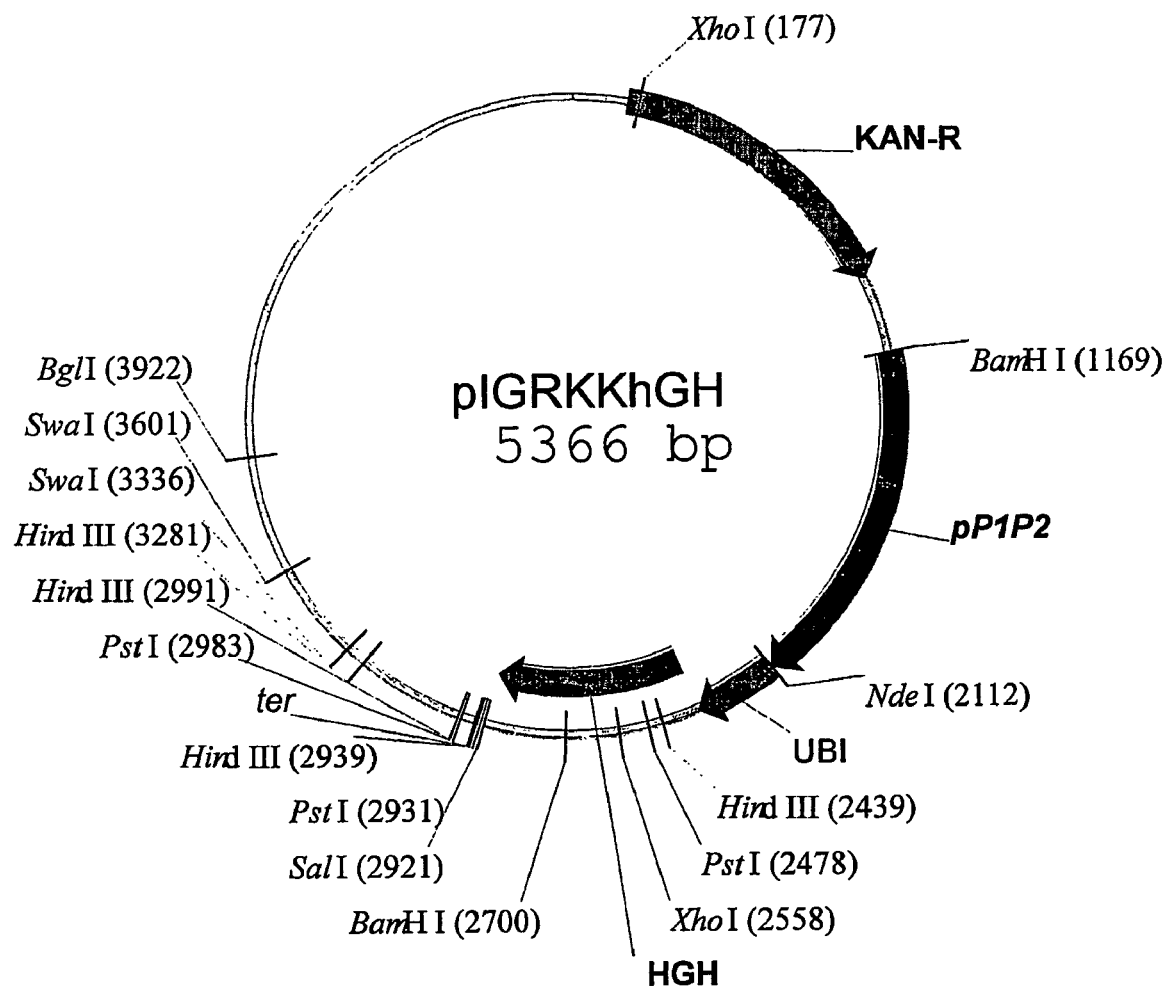

DNA fragments containing the promoters P1 and P2 [Fischer M, Short S. A. 1982, Gene, 17: 291-298] from the deo operon of E. coli strain K-12, the growth hormone and modified ubiquitin gene fusion and the transcription terminator sequence were cloned into new plasmid pIGRKKAN (SEQ ID NO: 19), which has been isolated from Klebsiella pneumoniae strain 287-w. The restriction map and nucleotide sequence of the plasmid pIGRKKAN are presented in FIGS. 7 and 8 (SEQ ID NO: 19). The restriction map of the recombined plasmid designated pIGRKKhGH (SEQ ID NO: 20) is presented in FIGS. 9 and 10. The selection factor in the expression vector is the kanamycin resistance gene from the commercial transposon EZ::TN™<KAN-2>.

Plasmid pIGRKKhGH (SEQ ID NO: 20) is 5366 base pairs and contains the following sequences:
- promoters P1 and P2 of the E. coli deo operon at 1169-2112 bp
- a sequence coding ubiquitin (UBI) at 2113-2340 bp
- a sequence coding human growth hormone (hGH) at 2341-2916 bp
- a gene coding kanamycin resistance (KAN-R) at 147-962.

The plasmid was used to transform cells of E. coli strain DH5α. Electrophoretic analysis of lysates indicated the presence of a protein nearly identical in size with a UBI-Hgh marker.

Plasmid pIGALUH (SEQ ID NO: 21)

Figure 11:
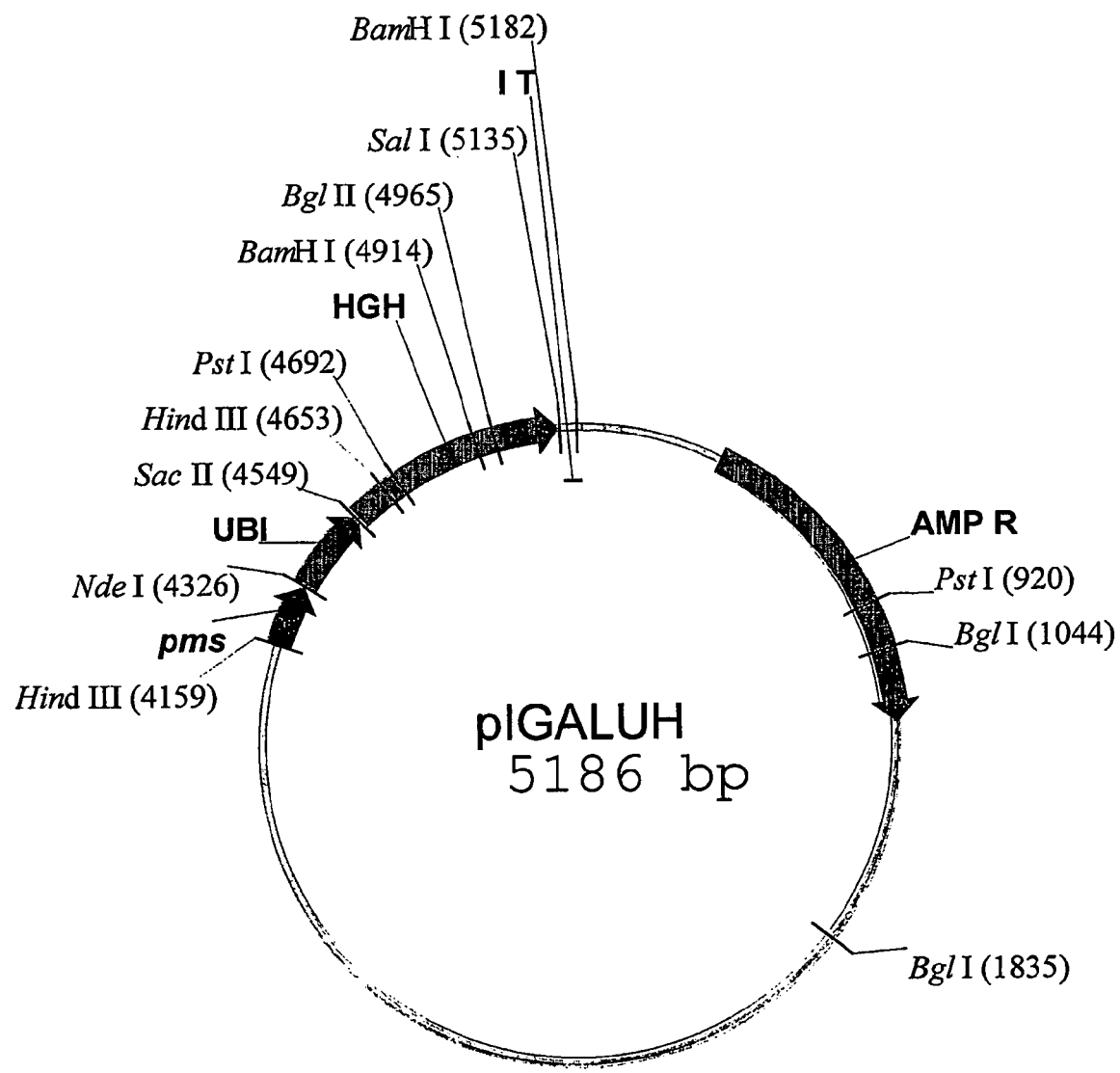

FIG. 11 i 12 (SEQ ID NO: 21) represents the structure of the plasmid coding the ubiquitin-growth hormone fusion, which is capable of efficiently expressing the fusion protein useful in manufacturing human growth hormone following transfection into an appropriate E. coli host. The nucleotide and amino-acid sequences of the plasmid pIGALUH are represented in FIG. 11 i 12 (SEQ ID NO: 21).

The plasmid is introduced into E. coli strain DH5α cells, where the efficient expression of the hybrid protein ubiquitin-human growth hormone takes place.

The plasmid, pIGALUH (SEQ ID NO: 21), is 5186 bp long and is composed of the following genes and sequences:
- 374 bp to 1234 bp contains the ampicillin resistance gene,
- 4158 bp to 4323 bp contains the pms promoter
- 4327 bp to 4554 bp contains the to ubiquitin-coding region
- 4555 bp to 5130 bp contains the human growth hormone-coding region
- 5140 bp to 5186 bp contains the transcription terminator sequence.

The plasmid pIGAL1 was used in the vector construction, from which a significant portion of the TN3 transposon (the stretch between Bam HI restriction sites) was removed. The NdeI site was also removed from the resultant plasmid. The sequence of the plasmid pIGAL1 is stored in GenBank under the accession AY424310.

plasmid pIGALUHM (SEQ ID NO: 22)

Figure 13:
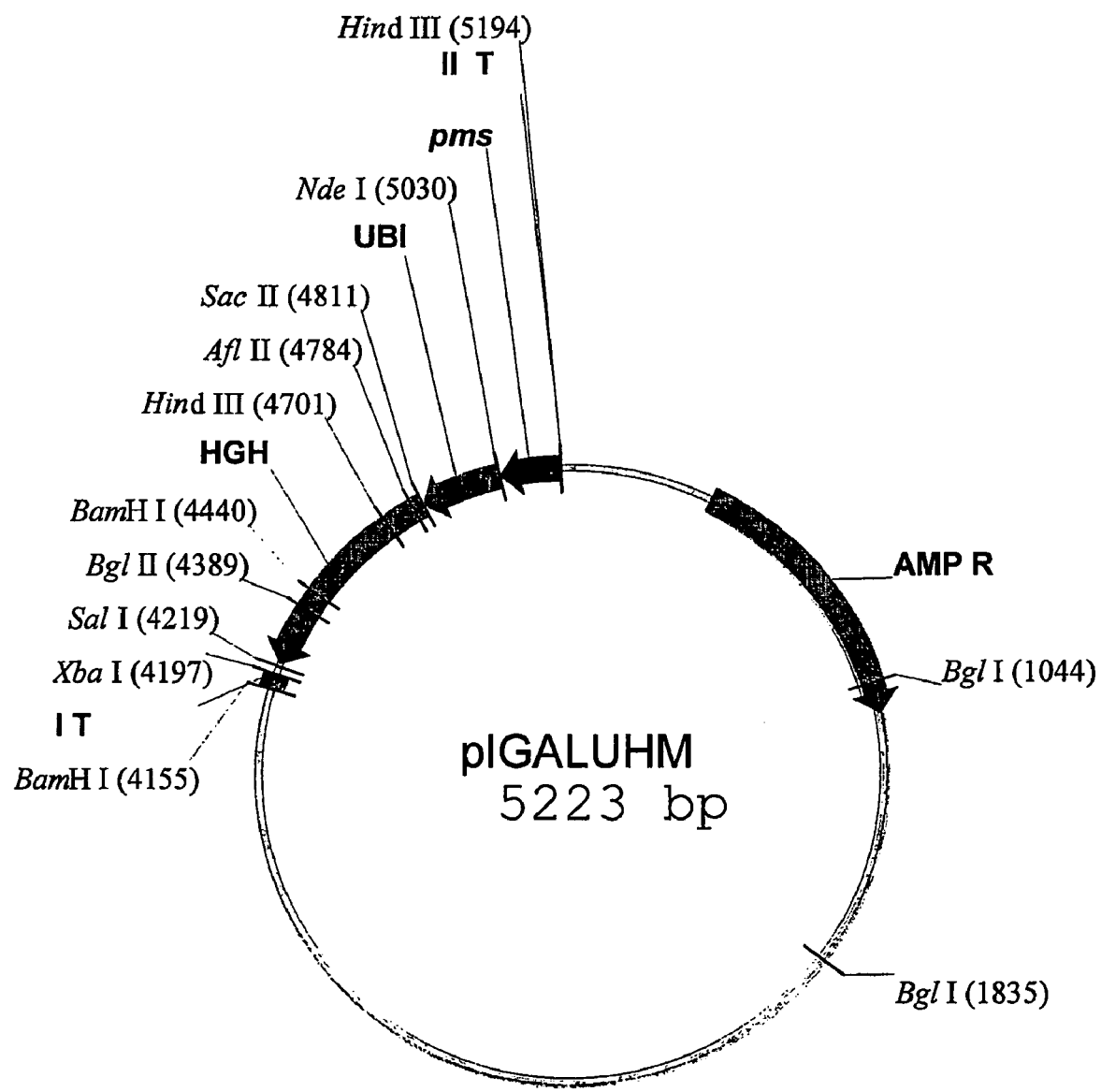

The nucleotide and amino-acid sequences of plasmid pIGALUHM as well as its structure are represented in FIGS. 13 and 14. the plasmid is introduced into E. coli strain DH5α cells, where the efficient expression of the hybrid protein ubiquitin—human growth hormone takes place.

Plasmid pIGALUHM (SEQ ID NO: 22) is 5229 base pairs long and is composed of the following genes and sequences:
- 374 bp to 1234 bp contains the ampicillin resistance gene,
- 5033 bp to 5198 bp contains the pms promoter on the complementary strand
- 4802 bp to 5029 bp contains the ubiquitin-coding region on the complementary strand
- 4226 bp to 4801 bp contains the human growth hormone-coding region on the complementary strand
- 4153 bp to 4197 bp contains the transcription terminator I sequence on the complementary strand
- 5194 bp to 5218 contains the additional, transcription terminator II sequence on the complementary strand.

Plasmid pIGDMKUH (SEQ ID NO: 23)

Figure 15:
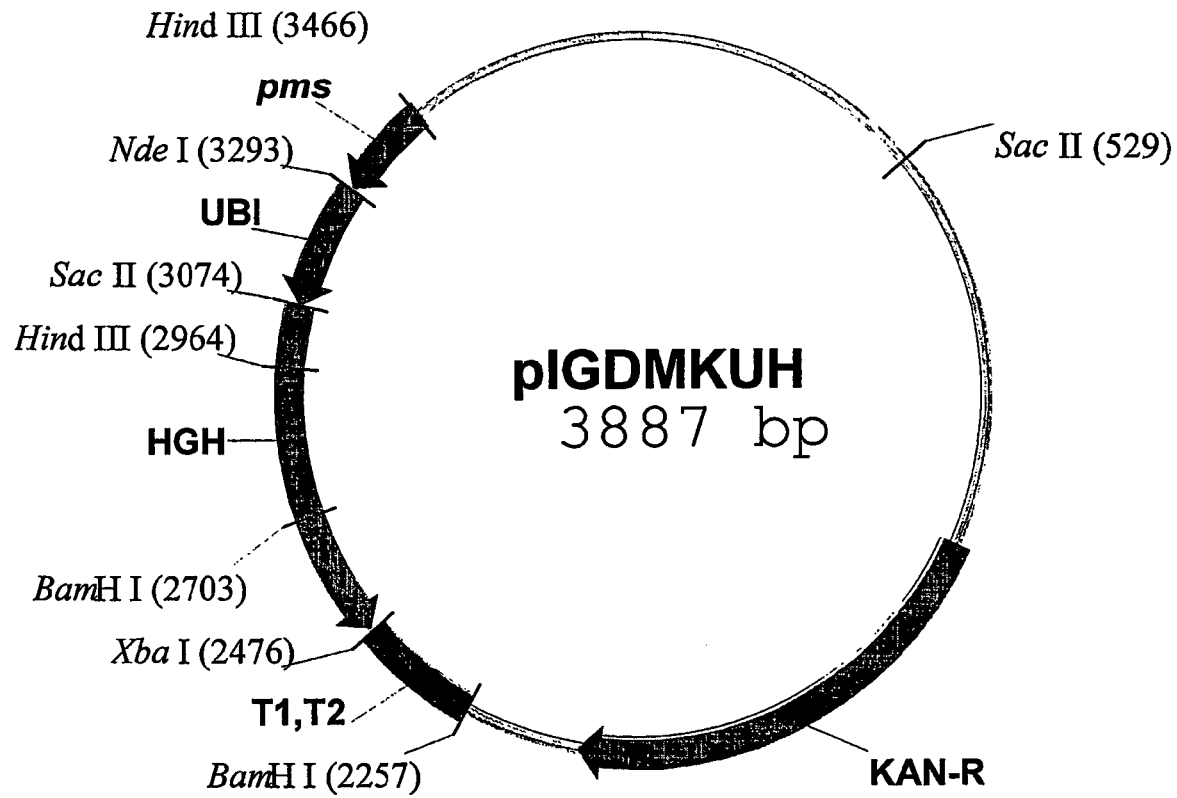
Figure 17A:
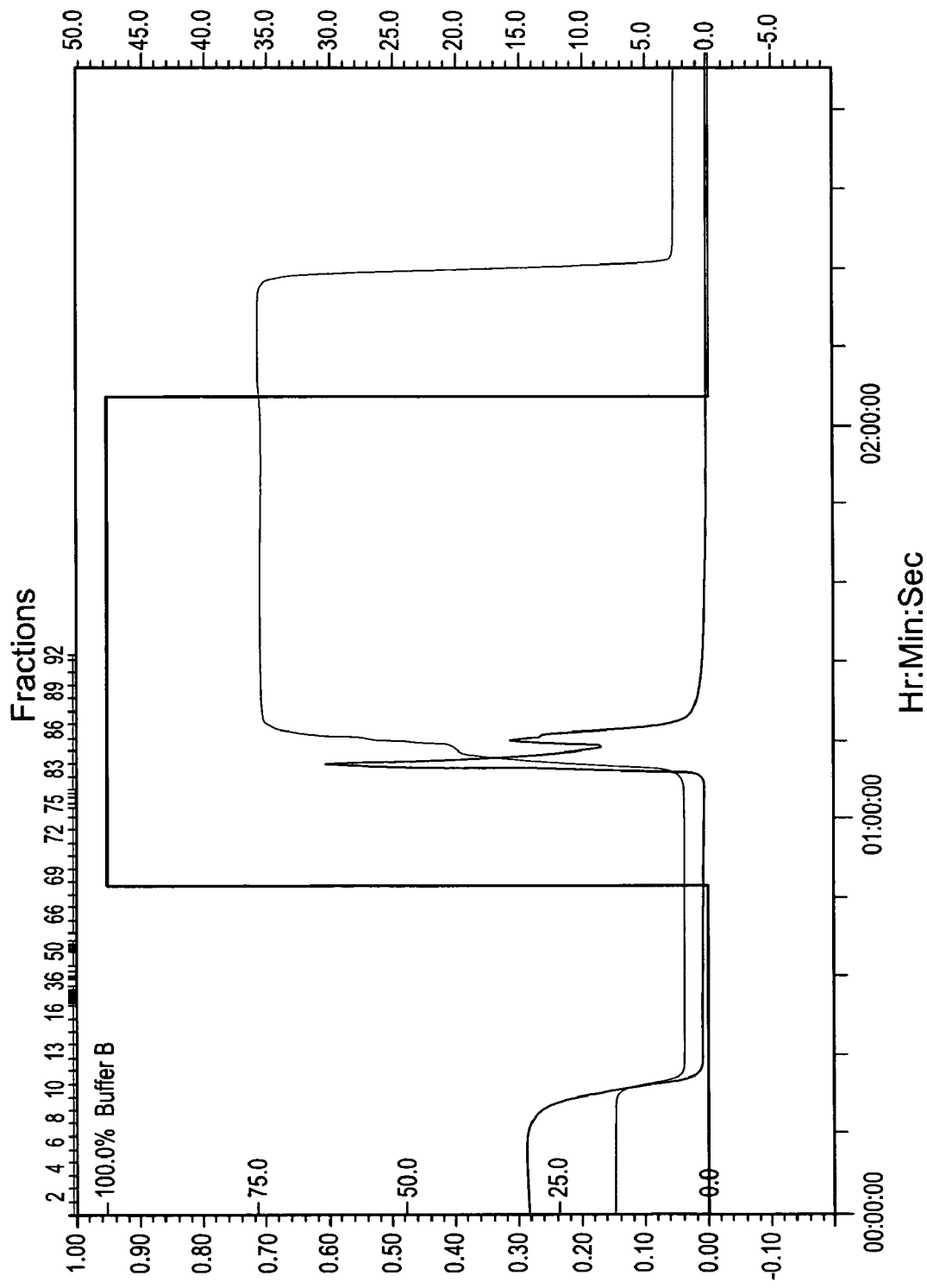
FIG. 17a shows the separation on a DEAE Sepharose FF column, FIG. 17b the separation on a SP Sepharose FF column.
Figure 17B:
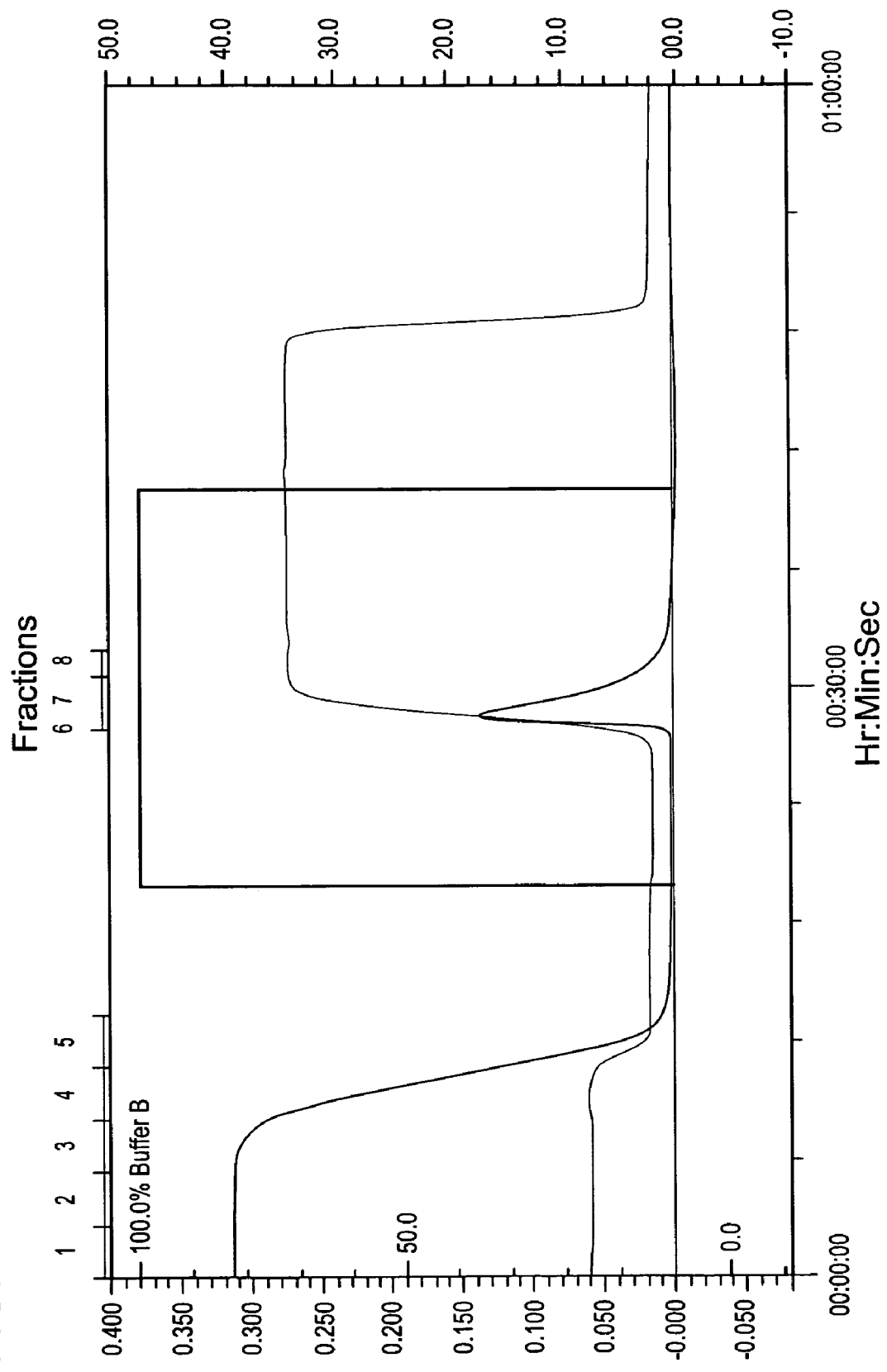
FIG. 17 represents chromatographs from sequential steps of purification of the protein.
FIG. 17c shows the separation on a Phenyl Sepharose FF column.
Figure 17C:
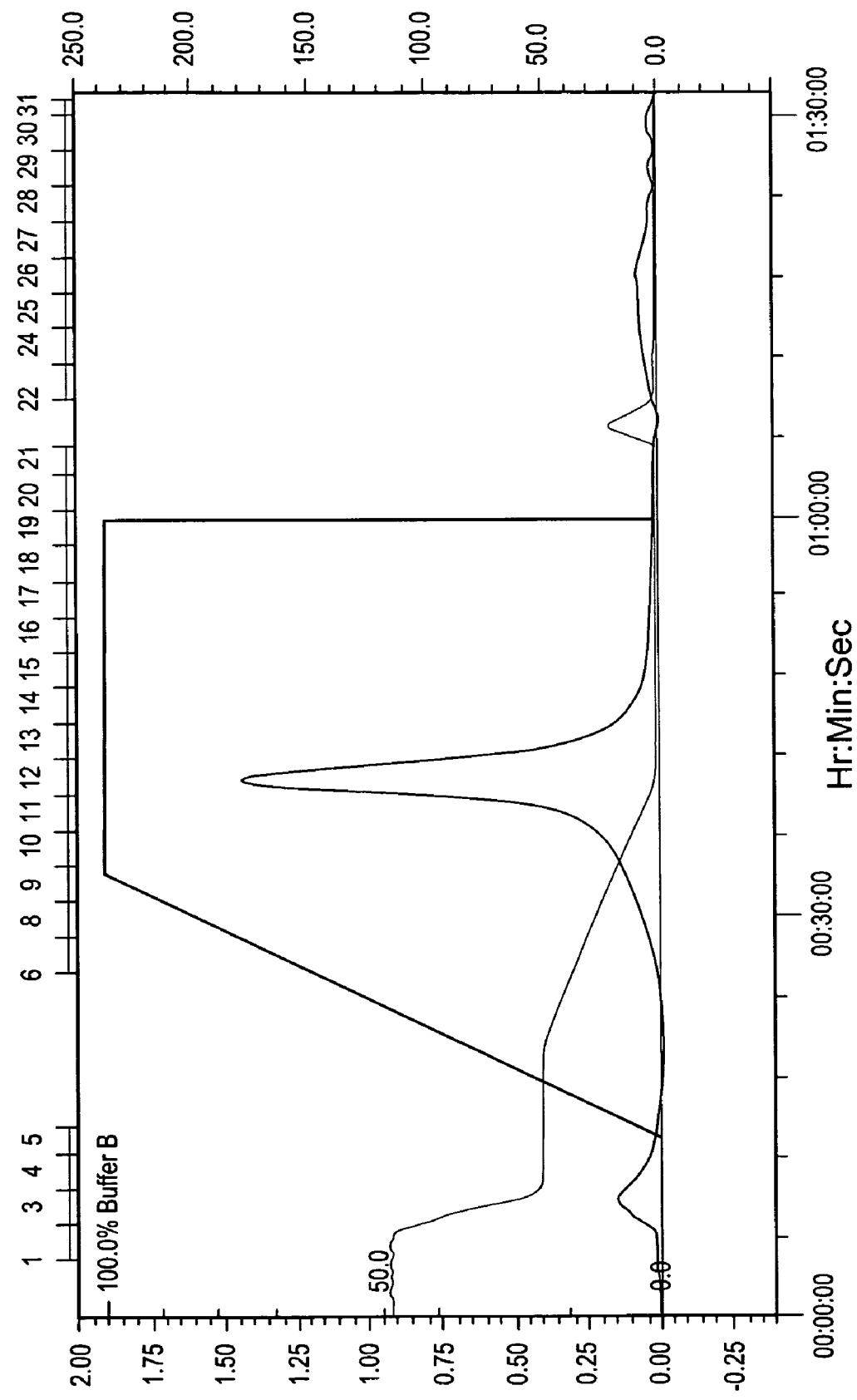
Figure 18A:
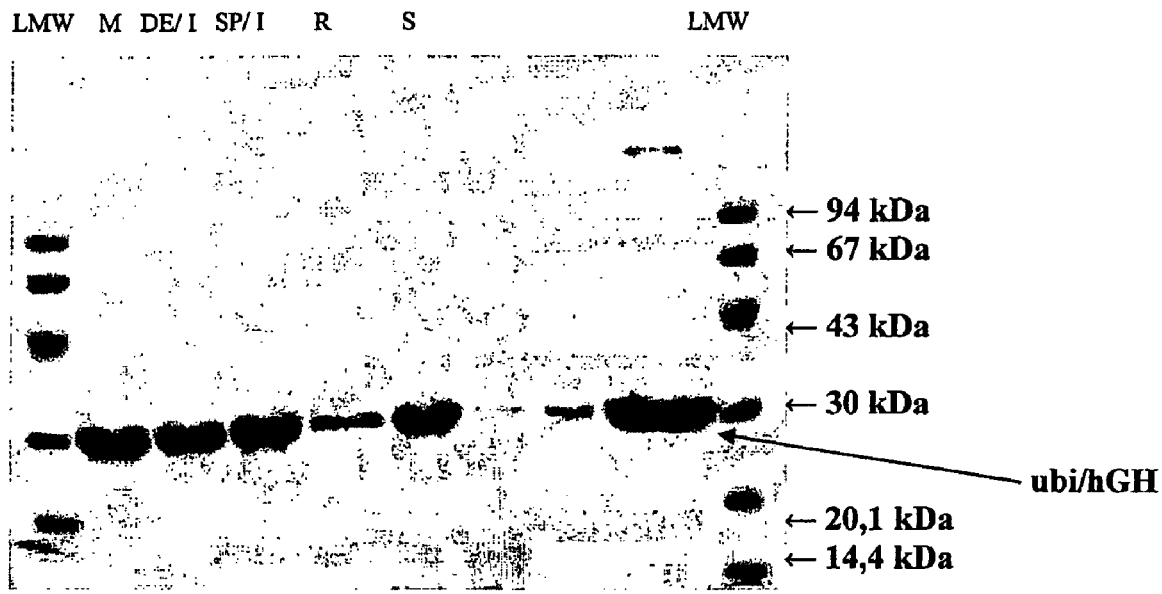
FIGS. 18(a) and 18(b) each represents electrophorograms from sequential steps of the purification of growth hormone, where the symbols used mean: LMW—standard LMW (94 kDa; 67 kDa; 43 kDa; 30 kDa; 20.1 kDa; 14.4 kDa), STD/E—European growth hormone standard, M—the protein dissolved in DRCI—6 buffer, R—renatured protein, DE/I—peak I from the DEAE Sepharose fast flow column, SP/I—peak I from the SP Sepharose fast flow column, S—sample following ammonium sulphate precipitation, Ph/W—input into the Phenyl Sepharose fast flow column (after digestion with UBP1ΔC2 and centrifugation, Ph/fraction No.—fractions from the Phenyl Sepharose fast flow column.
Figure 18B:
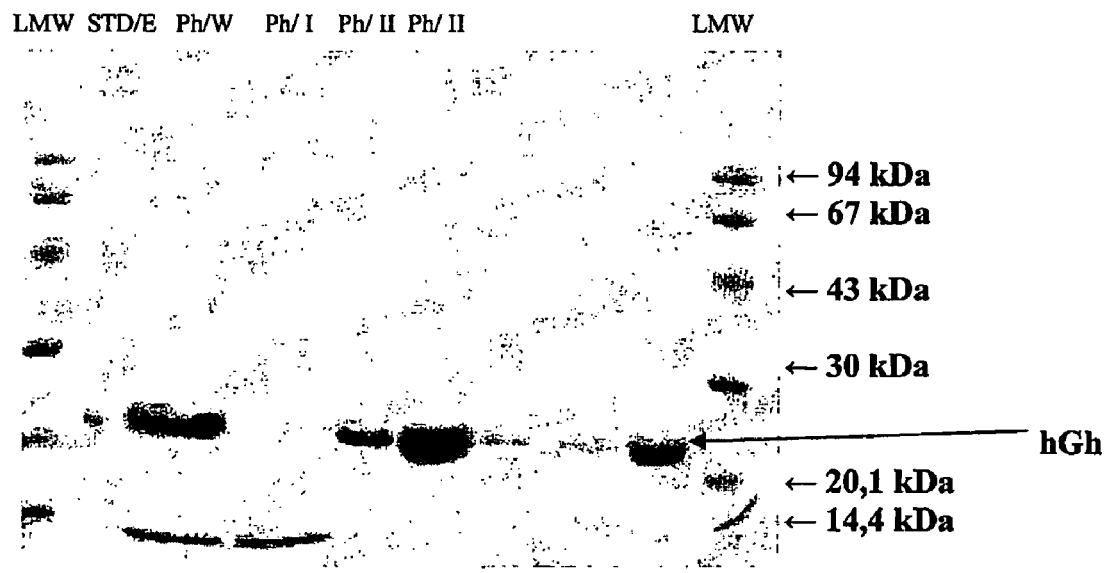
Figure 19:
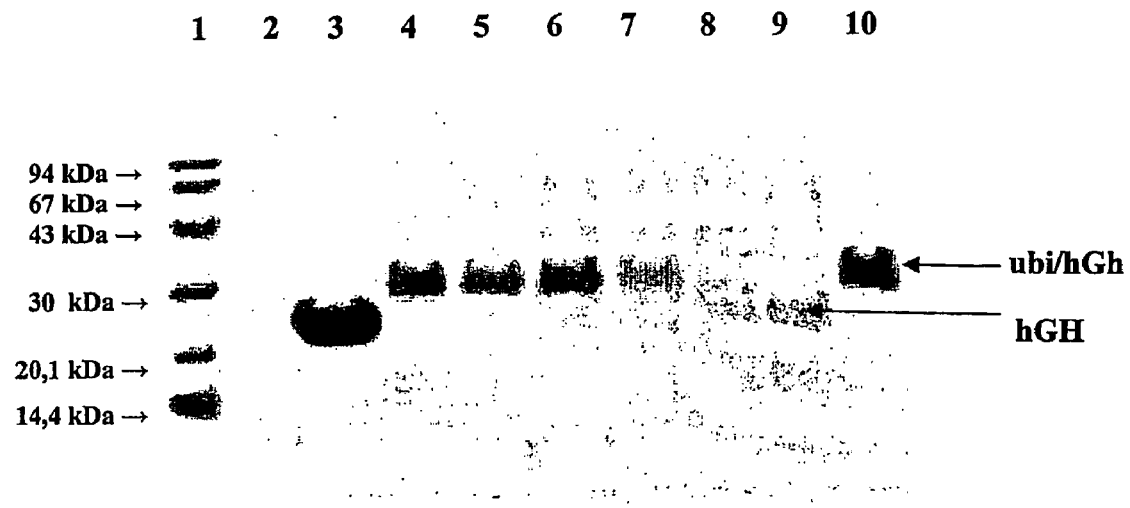
FIG. 19 represents the results of cleaving the ubiquitin carrier protein with yeast extract, where the symbols used represent: 1—Standard LMW, 2—yeast extract, 3—Standard hGH, 4—5 min digestion, 5—10 min digestion, 6—20 min digestion, 7—30 min digestion, 8—60 min digestion, 9—120 min digestion, 10—Standard ubi/hGH.
Figure 20:
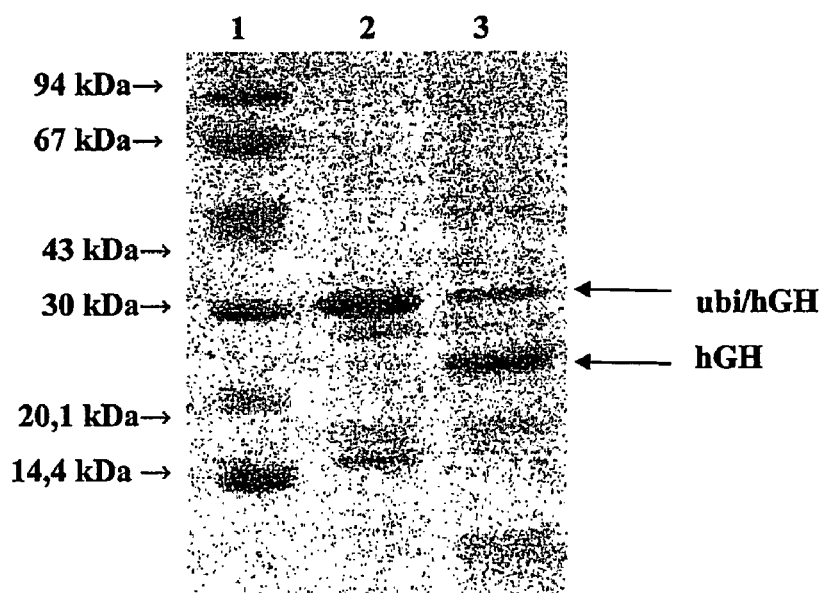
FIG. 20 represents the results of cleaving the ubiquitin carrier protein with the enzyme UBP1 ΔC, where the symbols used represent: 1—Standard LMW, 2—ubi/hGH preparation used for digestion, 3—UBP1ΔC digestion for 60 min.

Plasmid pIGDMKUH (SEQ ID NO: 23) (FIGS. 15 and 16) was constructed, capable of efficiently directing the expression of the hybrid polypeptide synthetic ubiquitin-human growth hormone useful in producing human growth hormone, upon transfection into appropriate E. coli host cells.

The structure of plasmid pIGDMKUH (SEQ ID NO: 23), coding the hybrid protein synthetic ubiquitin-human growth hormone is represented in FIG. 1. The DNA sequence with the delineated amino-acid sequence of the hybrid protein synthetic ubiquitin—human growth hormone is represented in FIG. 2.

Plasmid pIGDMKUH (SED ID NO: 23) is 3887 base pairs long and contains the following elements:
- A 172 bp DNA fragment, between nucleotides 3298-3470 on the complementary strand, which contains a modified pms promoter,
- A 227 bp DNA fragment, between nucleotides 3293-3066 on the complementary strand, which contains the gene coding synthetic ubiquitin UBI,
- A 575 bp DNA fragment, between nucleotides 3065-2490 on the complementary strand, which contains the gene coding human growth hormone HGH,
- A 202 bp DNA fragment, between nucleotides 2269-2471 on the complementary strand, which contains the transcription terminators T1, T2 [Brosius J., Holy A. (1984), Proc. Natl. Acad. Sci. USA, Vol. 81, pp. 6929-6933]
- An 815 bp DNA fragment, between nucleotides 1235-2050 containing the kanamycin resistance gene KAN-R.

Plasmid pIGDMKUH (SEQ ID NO: 23) was constructed based on plasmid pIGDM1, which was entered in GenBank under the accession number AF014880.

EXAMPLE 2

Stock Preparation

The method of preparing stocks is important in maintaining the efficient expression and stability of a plasmid in host cells. A fresh transformation, temperature of culturing as well as the time and OD of the bacterial culture are significant points of this stage.

Plasmid pIGALUH (SEQ ID NO: 21) was used to transform E. coli strain DH5α cells. The transformation was performed using the modified protocol of Chung and Miller (1988).

Competent cells were thawed immediately before transformation in an ice bath. 0.1 μg of the pIGALUH plasmid solution was added, and left on ice for 30 min. All material was transferred into sterile tubes containing 0.85 ml of LB medium with PEG-6000 (polyethylene glycol), 50 μl DMSO (dimethyl sulfoxide), 20 μl glucose. The mixture was incubated for 1 hour on a shaker at 37° C. bacteria prepared in this fashion were inoculated onto plates with solid LB medium with antibiotic (ampicillin 100 μg/ml). These were incubated overnight at 37° C.

One bacterial colony was used to inoculate 3 ml of liquid LB medium with ampicillin. After 4 hours of shaken culture at 37° C., all material was transferred into 20 ml of LB medium with ampicillin. Shaken cultures were maintained at 37° C. until clouding occurred, where at $\lambda$=600 nm OD was ~1.

0.5 ml of culture were transferred into sterile Eppendorf tubes, to which 0.5 ml of 40% glycerol were added. Stocks prepared in this fashion were stored at −70° C.

Generally, further stages of the example embodiment according to the present invention, described below, encompass the production of the fusion protein ubiquitin-growth hormone through the expression of this protein in a bacterial cell, reclamation of this protein (isolation), purification of the fusion protein, conformation of the fusion protein obtained due to the purification of the hybrid protein, enzymatic digestion of the conformed (and possibly concentrated) fusion protein in order to obtain growth hormone, as well as he purification of growth hormone thus produced. A schematic representing purification stages is shown in FIG. 22.

Fermentation, growth conditions, isolation of inclusion bodies

The following solutions were used in the example embodiment:

Buffer C
  50 mM Tris HCl pH 7.5, 0.5 M NaCl, 5 mM beta-mercaptoethanol

Buffer CT
  50 mM Tris HCl pH 7.5, 0.5 M NaCl, 5 mM beta-mercaptoethanol, 1% triton X-100

Inclusion Body Dissolution Buffer (DRCI)
  6-8 M urea, 50 mM phosphate buffer pH 12.0, 5 mM beta-mercaptoethanol Renaturation Buffer (BR)
  20 mM phosphate buffer pH 7.0, 50 mM NaCl, Protein Lysis Buffer
  50 mM Tris HCl pH 6.8, 2% SDS, 0.1% bromophenol blue, 10% glycerol, 0.5% β-mercaptoethanol Medium LB: yeast extract (Difco): 5 g, tryptone (Difco): 10 g, NaCl (Baker): 10 g, distilled water up to 1000 ml.

Stock Preparation

Competent cells were thawed immediately before transformation in an ice bath. 0.1 μg of the pIGDMKUH plasmid solution was added, and left on ice for 30 min. All material was transferred into sterile tubes containing 0.85 ml of LB medium with PEG-6000, 50 μl DMSO, 20 μl glucose. The mixture was incubated for 1 hour on a shaker at 37° C. bacteria prepared in this fashion were inoculated onto plates with solid LB medium with antibiotic (kanamycin 50 μg/ml). These were incubated overnight at 37° C.

One bacterial colony was used to inoculate 3 ml of liquid LB medium with ampicillin. After 4 hours of shaken culture at 37° C., all material was transferred into 20 ml of LB medium with kanamycin. Shaken cultures were maintained at 37° C. until clouding occurred, where at $\lambda$=600 nm OD was ~1.

0.5 ml of culture were transferred into sterile Eppendorf tubes, to which 0.5 ml of 40% glycerol were added. Stocks prepared in this fashion were stored at −70° C.

Production Culture

Was used added 0.5-1% stock/1 L culture medium. 200 ml of LB medium were added into a 500 ml flask, as well as: 200 μl ampicillin (100 mg/ml) or 200 μl kanamycin (50 mg/ml) and 100 μl of the inoculate. The culture was maintained in a rotary shaker at 160 obr./min, a temperature of 37° C. for 18 hours. The culture was centrifuged at 6 000 rpm for 15 min. at 4° C. Further procedures used the bacterial cell precipitate.

Isolation of Inclusion Bodies (with 25% Glycerol)

Cell Biomass:
  suspended in 100 ml of buffer C, added lysozyme to a final concentration of 0.43 mg/ml and incubated for 35 minutes at 20° C.
  added Triton X-100 to a final concentration of 1%, sonificated (Ultrasonic processor 400 W) over 20 min, in an ice bath with a 33% amplitude.
  PMSF was addet to a final conc. of 1 mM, ⅓ of the bacteria-glycerol suspension mass was added.
  centrifugation at 8 000 rpm for 20 min. at 20° C.
  the precipitate was suspended in 100 ml buffer CT, and sonificated for 10 min in an ice bath with a 33% amplitude.
  centrifugation at 8 000 rpm for 20 min. at 20° C.
  the precipitate was suspended in 100 ml PBS with 1% Triton X-100, and sonificated for 10 min in an ice bath with a 33% amplitude.
  centrifugation at 8 000 rpm for 20 min. at 20° C.
  the precipitate was suspended in 100 ml PBS with 2M urea, and sonificated for 10 min in an ice bath with a 33% amplitude.
  centrifugation at 8 000 rpm for 20 min at 20° C.

The sonification yielded from 0.7 to 1.2 g of inclusion bodies per 1 L of culture.

The results from the culturing and isolation of inclusion bodies from both strains are shown in the table below.

TABLE 1

| STAGE | VOLUME [ml] | OD λ = 600 | MASS [g] |
| --- | --- | --- | --- |
| Stock | 0.5 | — | — |
| Production culture | 1000 | 1-1.5 | — |
| bacterial cells | — | — | 5-7 |
| Inclusion bodies | — | — | 0.7-1.2 |

The inclusion bodies were dissolved in 6-8 M urea, 50 mM phosphate buffer, 5 mM beta-mercaptoethanol pH 12 (DRCI). The solution was centrifuged, pH was adjusted up to 7.0 with concentrated phosphate acid and added to the following chromatography columns:

DEAE Sepharose Fast Flow

A column of ca. 100 ml was filled with the weak anionite DEAE Sepharose fast flow from Amersham Pharmacia Biotech AB and equilibrated with 6-8 M urea, 20 mM phosphate buffer pH 7.0. Unbound material was collected and the fusion protein was placed on SP Sepharose FF.

SP Sepharose Fast Flow

A column of 30 ml filled with the strong cationite SP Sepharose fast flow from Amersham Pharmacia Biotech AB was equilibrated with 6-8 M urea, 20 mM phosphate buffer pH 7.0. Fusion protein fractions from the DEAE Sepharose FF were placed on this column. Material unbound to the column was collected and subjected to renaturation. Separation on this column is not necessary if the protein yield from the DEAE column is about 70%.

Renaturation

Fractions from the SP Sepharose FF column were renatured through a ca. 10-fold dilution in BR buffer (until a concentration of 0.09-0.15 mg/ml protein was reached) and incubated for an hour at room temperature.

Ammonium Sulphate Precipitation.

After renaturation, the fusion protein was precipitated with ammonium sulphate to 80% saturation, at 4° C. with stirring. Next, the samples were centrifuged at 12 000 rpm for 15 min at 4° C. The pellet was suspended in ca 50 ml (1/40 pre-centrifugation sample volume) 20 mM phosphate buffer pH 7.5+0.5 M NaCl, and then centrifuged at 12 000 rpm for 15 min at 4° C.

Cleavage of the Carrier Protein—Ubiquitin.

The supernatant obtained (partially purified fusion protein in 20 mM phosphate buffer pH 7.5+0.5 M NaCl) underwent an enzymatic reaction as a result of which the carrier protein ubiquitin was cleaved from growth hormone. The reaction was performed with an appropriate amount of enzyme at 37° C. for 1 h (UBP1Δ C 2 1 µg-60 µg protein, UBP1Δ C 1 µg-14 µg protein, yeast extract 1 µg-4 µg protein). Next, the sample was centrifuged at 12000 rpm for 15 min at 4° C. The supernatant was placed on a column.

Phenylo Sepharose Fast Flow

A ca. 20 ml column, filled with the hydrophobic carrier Phenylo Sepharose fast flow from Amersham Pharmacia Biotech AB, was equilibrated with 0.5M NaCl, 20 mM phosphate buffer pH 7.0. The post-digestion protein was eluted with a 3 mM phosphate buffer pH 7.0-9.0. Fractions containing growth hormone were collected. The protein solution was corrected to pH 7.0 using concentrated phosphoric acid and stored at 4° C.

Q Sepharose Fast Flow

In order to concentrate the samples, an additional stage was used. A ca. 10 ml column was filled with the strong anionite Q Sepharose fast flow from Amersham Pharmacia Biotech AB. The carrier was equilibrated with 20 mM phosphate buffer pH 7.5. Growth hormone fractions obtained in the previous separation were transferred to the column and eluted with a linear gradient of 0.5 M NaCl in 20 mM phosphate buffer pH 7.5 (growth hormone-containing fractions are eluted at 0.25 M NaCl).

All stages of purifications may be performed at a temperature range of 4-24° C.

Figure 21:
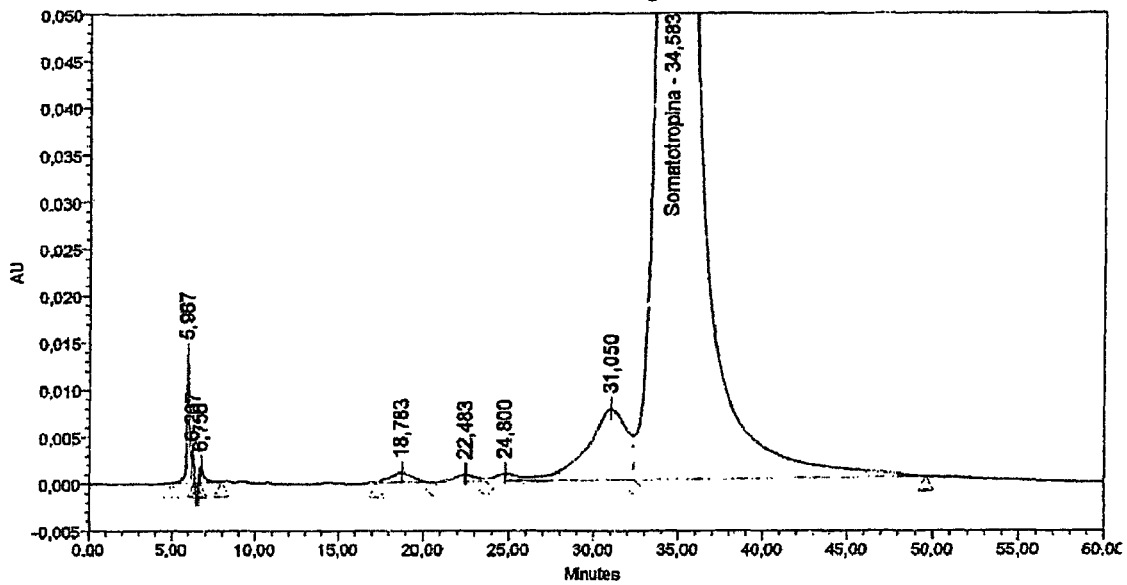
FIG. 21 represents hGH purity assay results following the final stage of purification, Phenylo Sepharose FF.

The following analyses were performed to identify the protein as pure growth hormone:
HPLC purity (FIG. 21) performed by the Chemical Analysis Department of IBA Warsaw, sequencing of the N-end (15 amino-acid residues) performed by Biocentrum Kraków and mass spectroscopy (confirmation of the molecular mass of pure hGH) performed by IBB, Warszawa.

The assays performed show that the protein is human growth hormone.

To summarise the described embodiment of the method according to the present invention it is possible to state for both strains of *Escherichia coli* transformed with plasmid DNA with an inserted ubiquitin-growth hormone gene yielded satisfactory expressions of the ubiquitin-growth hormone protein in LB medium, where in both cases the majority of the fusion protein ubiquitin—growth hormone was produced in inclusion bodies. The efficiency of protein expression is sufficiently high, and the presented strains of *Escherichia coli* may be assayed for production of hGH on an industrial scale. An example embodiment of further stages of protein purification which encompass cell lysis, isolation of inclusion bodies and their dissolution, renaturation and purification on various chromatographic carriers.

REFERENCES

1. R. Baker, Current Opinion In Biotechnology 1996, 7:541-546.
2. J. Brosius, A. Holy (1984), Proc. Natl. Acad. Sci. USA, Vol. 81, 6929-6933
3. C. T. Chung, R. T. Miller, Nucleid Acids Res. 1988, 16 (8): 3580.
4. M. Fischer, S. A. Short 1982, Gene, 17: 291-298
5. M. M. Harding, D. H. Williams, D. N. Woolfson, Biochemistry 1991, 30: 3120-3128
6. J. Tobias, A. Varshavsky, J. Biol. Chem. 1991, 266: 12021-12028
7. S. Vijay-Kumar, C. Bugg, W. Cook, J. Mol. Biol. 1987, 194:531-544

What is claimed is:

1. A method of producing somatotropin comprising:
   (a) expressing a hybrid polypeptide in bacterial cells wherein the hybrid polypeptide comprises ubiquitin and somatotropin;
   (b) extracting the hybrid polypeptide from the bacterial cells;
   (c) digesting the extracted hybrid polypeptide with a ubiquitin-cleaving enzyme so as to produce biologically active somatotropin, wherein the ubiquitin-cleaving enzyme is a UBP1 protease mutant containing an amino-acid sequence containing at least one of the modifications selected from the group consisting of:
      a substitution at position 754 of the UBP1 amino acid sequence,
      a deletion of at least a portion of the amino acids at positions 1 to 98 of the UBP1 sequence,
      replacement of the proline at position 415 of the UBP1 sequence with leucine, and
      replacement of the phenylalanine at position 739 of the UBP1 sequence with leucine, and
   (d) purifying the produced somatotropin from a protein mixture.

2. The method according to claim 1, wherein the bacterial cells are E. coli cells transformed with a plasmid selected from the group consisting of pIGALUH (SEQ ID NO: 21), pIGALUHM (SEQ ID NO: 22), pIGDMKUH (SEQ ID NO:23), and pIGMS31PRH (SEQ ID NO: 18).

3. The method of claim 2 wherein the E. coli is a DH5αstrain of E. coli.

4. A method according to claim 1 wherein the hybrid polypeptide is extracted in step (b) in a process comprising
   (i) lysing a bacterial cell wall or its fragments in order to form a lysate containing inclusion bodies;
   (ii) isolating inclusion bodies from the lysate; and
   (iii) solubilizing the inclusion bodies.

5. The method according to claim 4, wherein the isolation of the inclusion bodies occurs in the presence of 25% glycerol.

6. The method according to claim 4, further characterised in that the solubilization of the inclusion bodies takes place in denaturing conditions.

7. The method of claim 6 wherein the inclusion bodies are solubilized in the presence of urea.

8. The method according to claim 6, further characterised in that the solubilization of the inclusion bodies takes place in a buffer with a pH of about 12 containing: 6-8 M urea and 5 mM beta-mercaptoethanol.

9. The method according to claim 1, further comprising purifying the hybrid polypeptide extracted from the bacterial cells by means of DEAE-Sepharose chromatography.

10. The method of claim 9 wherein the hybrid polypeptide is solubilized in the presence of 6-8 M urea and pH 7.0 prior to DEAE-Sepharose chromatography.

11. The method according to claim 1, further comprising purifying the hybrid polypeptide extracted from the bacterial cells by means of SP-Sepharose FF chromatography.

12. The method of claim 11 wherein the hybrid polypeptide is solubilized in the presence of 6-8 M urea at about pH 7.0 prior to SP-Sepharose chromatography.

13. A method according to claim 1, wherein the hybrid polypeptide in step (b) is incubated at a temperature of 4-24° C. for 0.5-5 hours at a pH of about 6.5-8.0, in a renaturation buffer containing 20 mM phosphate buffer, pH 7-8 and 50 mM NaCl, wherein the protein concentration in solution is about 0.1 mg/ml solution.

14. The method according to claim 1, further comprising in that step (b) comprises producing a concentrated solution of the hybrid polypeptide through precipitation of the hybrid polypeptide with ammonium sulphate.

15. The method of claim 14 wherein the precipitation is performed up to 80% saturation with ammonium sulphate, centrifugation and resuspension of the hybrid polypeptide in a decreased amount of phosphate buffer with pH 7, containing 50 mM NaCl.

16. The method according to claim 1, further comprising in step (c):
   (i) adjusting the pH to about 7-8, and
   (ii) digesting the hybrid polypeptide with a ubiquitin-cleaving enzyme at a temperature of about 37° C. over 30 min to 3 hours, where the enzyme cleaving off the ubiquitin is contained in yeast extract or is the yeast protease ubiquitin protease 1 or its mutant.

17. The method according to claim 1, characterised in that the UBP1 protease mutant is UBP1ΔC2 (SEQ ID NO: 24) or UBP1ΔC (SEQ ID NO: 25).

18. The method according to claim 1, wherein in step (d) the protein mixture is separated through chromatography on the hydrophobic carrier Phenylo-Sepharose FF and collection of the fraction containing somatotropin, wherein a column is preferentially equilibrated with 20mM phosphate buffer, pH 7 containing 0.5 M NaCl, and protein elution is performed with 3-5 mM phosphate buffer, pH 7 to 9.

19. A method according to claim 1, characterised in that step (d) also encompasses further somatotropin purification through chromatography on the anionic carrier Q-Sepharose FF and collection of the fractions containing somatotropin, column is preferentially equilibrated with 20 mM phosphate buffer, pH 7.5 and the elution is performed using a NaCl concentration gradient in phosphate buffer, pH 7.5 where the somatotropin is eluted at a NaCl concentration of 0.25 M.

20. A plasmid selected from the group consisting of pIGA-LUH (SEQ ID NO: 21), pIGALUHM (SEQ ID NO: 22), pIGDMKUH (SEQ ID NO: 23), and pIGMS31PRH (SEQ ID NO: 18).

* * * * *

SEQUENCE LISTING

<160> NUMBER OF SEQ ID NOS: 36

<210> SEQ ID NO 1
<211> LENGTH: 42
<212> TYPE: DNA
<213> ORGANISM: Saccharomyces cerevisiae

<400> SEQUENCE: 1
ggggaattca tatgcaaatt tttgttaaaa ctttaactgg ta                42

<210> SEQ ID NO 2
<211> LENGTH: 42
<212> TYPE: DNA
<213> ORGANISM: Saccharomyces cerevisiae

<400> SEQUENCE: 2
aaaccattac cttagaagtt gaatcttcag ataccattga ta                42

<210> SEQ ID NO 3
<211> LENGTH: 42
<212> TYPE: DNA
<213> ORGANISM: Saccharomyces cerevisiae

<400> SEQUENCE: 3
atgttaaatc taaaattcaa gataaagaag gtattcctcc ag                42

<210> SEQ ID NO 4
<211> LENGTH: 42
<212> TYPE: DNA
<213> ORGANISM: Saccharomyces cerevisiae

<400> SEQUENCE: 4
atcaacaacg tctaatattt gcaggtaaac agttagaaga tg                42

<210> SEQ ID NO 5
<211> LENGTH: 42
<212> TYPE: DNA
<213> ORGANISM: Saccharomyces cervisiae

<400> SEQUENCE: 5
gtcgtaccct gtctgattat aacattcaga aagaatctac ct                42

<210> SEQ ID NO 6
<211> LENGTH: 42
<212> TYPE: DNA
<213> ORGANISM: Saccharomyces cervisiae

<400> SEQUENCE: 6
tacatctggt cttacgtctc cgcggtggtt aagtcgacga ga                42

<210> SEQ ID NO 7
<211> LENGTH: 24
<212> TYPE: DNA
<213> ORGANISM: Saccharomyces cervisiae

<400> SEQUENCE: 7
aggtaatggt tttaccagtt aaag                                    24

<210> SEQ ID NO 8
<211> LENGTH: 26
<212> TYPE: DNA
<213> ORGANISM: Saccharomyces cervisiae

```
<400> SEQUENCE: 8
ttagatttaa cattatcaat ggtatc                                              26

<210> SEQ ID NO 9
<211> LENGTH: 25
<212> TYPE: DNA
<213> ORGANISM: Saccharomyces cerevisiae

<400> SEQUENCE: 9
agacgttgtt gatctggagg aatac                                               25

<210> SEQ ID NO 10
<211> LENGTH: 24
<212> TYPE: DNA
<213> ORGANISM: Saccharomyces cerevisiae

<400> SEQUENCE: 10
acagggtacg accatcttct aact                                                24

<210> SEQ ID NO 11
<211> LENGTH: 24
<212> TYPE: DNA
<213> ORGANISM: Saccharomyces cerevisiae

<400> SEQUENCE: 11
agaccagatg taaggtagat tctt                                                24

<210> SEQ ID NO 12
<211> LENGTH: 27
<212> TYPE: DNA
<213> ORGANISM: Saccharomyces cerevisiae

<400> SEQUENCE: 12
tctcgtcgac ttaaccaccg cggagac                                             27

<210> SEQ ID NO 13
<211> LENGTH: 252
<212> TYPE: DNA
<213> ORGANISM: Saccharomyces cerevisiae
<220> FEATURE:
<221> NAME/KEY: CDS
<222> LOCATION: (12)...(239)

<400> SEQUENCE: 13
ggggaattca t atg caa att ttt gtt aaa act tta act ggt aaa acc att          50
            Met Gln Ile Phe Val Lys Thr Leu Thr Gly Lys Thr Ile
              1               5                  10 acc tta gaa gtt gaa tct tca gat acc att gat aat gtt aaa tct aaa           98
Thr Leu Glu Val Glu Ser Ser Asp Thr Ile Asp Asn Val Lys Ser Lys
         15                  20                  25 att caa gat aaa gaa ggt att cct cca gat caa caa cgt cta ata ttt          146
Ile Gln Asp Lys Glu Gly Ile Pro Pro Asp Gln Gln Arg Leu Ile Phe
 30                  35                  40                  45 gca ggt aaa cag tta gaa gat ggt cgt acc ctg tct gat tat aac att          194
Ala Gly Lys Gln Leu Glu Asp Gly Arg Thr Leu Ser Asp Tyr Asn Ile
                 50                  55                  60 cag aaa gaa tct acc tta cat ctg gtc tta cgt ctc cgc ggt ggt              239
Gln Lys Glu Ser Thr Leu His Leu Val Leu Arg Leu Arg Gly Gly
                 65                  70                  75 taagtcgacg aga                                                           252
```

```
<210> SEQ ID NO 14
<211> LENGTH: 76
<212> TYPE: PRT
<213> ORGANISM: Saccharomyces cerevisiae

<400> SEQUENCE: 14

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 15
<211> LENGTH: 576
<212> TYPE: DNA
<213> ORGANISM: Homo sapiens
<220> FEATURE:
<221> NAME/KEY: CDS
<222> LOCATION: (1)...(576)

<400> SEQUENCE: 15 ttc cca acc att ccc tta agt agg ctt ttt gac aac gct atg ctc cgc      48
Phe Pro Thr Ile Pro Leu Ser Arg Leu Phe Asp Asn Ala Met Leu Arg
 1               5                  10                  15 gcc cat cgt ctg cac cag ctg gcc ttt gac acc tac cag gag ttt gaa      96
Ala His Arg Leu His Gln Leu Ala Phe Asp Thr Tyr Gln Glu Phe Glu
            20                  25                  30 gaa gct tat atc cca aag gaa cag aag tat tca ttc ctg cag aac ccc     144
Glu Ala Tyr Ile Pro Lys Glu Gln Lys Tyr Ser Phe Leu Gln Asn Pro
        35                  40                  45 cag acc tcc ctc tgt ttc tca gag tct att ccg aca ccc tcc aac agg     192
Gln Thr Ser Leu Cys Phe Ser Glu Ser Ile Pro Thr Pro Ser Asn Arg
    50                  55                  60 gag gaa aca caa cag aaa tcc aac ctc gag ctg ctc cgc atc tcc ctg     240
Glu Glu Thr Gln Gln Lys Ser Asn Leu Glu Leu Leu Arg Ile Ser Leu
65                  70                  75                  80 ctg ctc atc cag tcg tgg ctg gag ccc gtg cag ttc ctc agg agt gtc     288
Leu Leu Ile Gln Ser Trp Leu Glu Pro Val Gln Phe Leu Arg Ser Val
                85                  90                  95 ttc gcc aac agc ctg gtg tac ggc gcc tct gac agc aac gtc tat gac     336
Phe Ala Asn Ser Leu Val Tyr Gly Ala Ser Asp Ser Asn Val Tyr Asp
            100                 105                 110 ctc cta aag gac cta gag gaa ggg atc caa acg ctg atg ggg agg ctg     384
Leu Leu Lys Asp Leu Glu Glu Gly Ile Gln Thr Leu Met Gly Arg Leu
        115                 120                 125 gaa gat ggc agc ccc cgg act ggg cag atc ttc aag cag acc tac agc     432
Glu Asp Gly Ser Pro Arg Thr Gly Gln Ile Phe Lys Gln Thr Tyr Ser
    130                 135                 140 aag ttc gac aca aac tca cac aac gat gac gca cta ctc aag aac tac     480
Lys Phe Asp Thr Asn Ser His Asn Asp Asp Ala Leu Leu Lys Asn Tyr
145                 150                 155                 160 ggg ctg ctc tac tgc ttc agg aag gac atg gac aag gtc gag aca ttc     528
Gly Leu Leu Tyr Cys Phe Arg Lys Asp Met Asp Lys Val Glu Thr Phe
                165                 170                 175 ctg cgc atc gtg cag tgc cgc tct gtg gag ggc agc tgt ggc ttc taa     576
Leu Arg Ile Val Gln Cys Arg Ser Val Glu Gly Ser Cys Gly Phe  *
```

180             185             190

<210> SEQ ID NO 16
<211> LENGTH: 191
<212> TYPE: PRT
<213> ORGANISM: Homo sapiens

<400> SEQUENCE: 16

Phe Pro Thr Ile Pro Leu Ser Arg Leu Phe Asp Asn Ala Met Leu Arg
  1               5                  10                  15

Ala His Arg Leu His Gln Leu Ala Phe Asp Thr Tyr Gln Glu Phe Glu
                 20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
         50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 17
<211> LENGTH: 172
<212> TYPE: DNA
<213> ORGANISM: E. coli

<400> SEQUENCE: 17
aagcttcagg gttgagatgt gtataagaga cagactctag ccagtttcca agtagaaact      60
acagtttcta aactgcaact ttttctactt tttgcaactt aatctattga ctagtccttt     120
ataaatgtta aacatatat atagaaataa ataaaaagag gaggttcata tg              172

<210> SEQ ID NO 18
<211> LENGTH: 4804
<212> TYPE: DNA
<213> ORGANISM: Homo sapiens

<400> SEQUENCE: 18
aggtttataa ctgagttata atacttata acttaattat taatgggtt ttaatatgaa         60 aaaaaataaa ttagtaaata aagaaaatta ctcaatatta gagactttgc cggaagatcc     120
attatttgaa aataaatcga ctttagaaat tgatttaaat caattcgatt tatttaatag     180
aattgcaaac gaaactgtag aagaacttat aataaaagaa gttaacgatc ctaatgaccg     240
aagcgataaa agcaatggtg ttaatttaaa tgcaaaagtt tatgtagaaa agaaaaaaa     300 gacttcatta aaaaaagatt tgttattac atttgtagat aatcttgagg ctttagcaaa     360

-continued

```
attaaattta aaacctaatg agtttagaat tatcgtcgag attgtaaagg ttatggaata    420
cggaaatcta attaaccttt cacaatctac aattgcgaaa aatttaaatc ttgcaaaatc    480
aaatgtaagt tattatttta aaaaccttaa aaagaaaaat atattagtag aaaaagacgg    540
acacgtcttt atgaatagta atattttttc taaaggatta gcccatcgtt tggacgaaga    600
aaaaagaaaa aatttgaaat ccgcacaagt cgaagacgat aattttaaaa actcatttta    660
aaacccaacg ggaattttt cactgttttcc cgttccgggc tttataattt taaagccttt    720
ggcttattct ggggtgtgta gttattattt tgctgtttct gtgaatattc ggcatctgct    780
gctgcaatag cagcattgaa gagttgttta aattctgccg gtttatgctc ttgtattaga    840
tctaaaacat cactgttaat tttatatttt tcatatctct gagaaattga agcattttcc    900
tttaactgcc ttttgtattc tattatttcc aactccatat cttttatttt tctgttttta    960
ttttgaatga tttgttcttg ctcagccgtg gctctggcca ctgctaactt ttgctcctgt   1020
tgtacccgtt cctggactct tctgttgaag ttctgacgga gatcagacaa ctcagcctct   1080
gaatgctcta aacggctctt aaacccgttt agacgagcta aaggggctt tcgttcgttc    1140
ttgtaaggtt ttagagcctt tcgtatgtaa cgattaacct cagctcctgt gtagtgctta   1200
ggcactacct ccggatctct aaataatttt ttcttttctt ctgtttcaac aactctaatt   1260
ttttcaattt tattattttc tatttctaat tcggtttcat tcttaatgtt tttaatatcg   1320
ctgtaaaatt ctttaacttc cttatattct gcattcgaaa cctcttttt aatcccacgg    1380
attaaaccta atggcttatt gtatttaaaa tatatatcct gcattgtttc gtattttttc   1440
atatacgatt tattgtttag tttatatatt ccgtttttat tttcgattgg tgttataaag   1500
gcgtgaatat gtggagtttg ctcgtccaag tgtaaaactg cattaattgc attttcccca   1560
tattcacttt gcaaatattc catttgaact ttaatccaat cctccaattt tttgttattt   1620
gcaaaaaatt ctggggaagc tgttaaaact aattcattac aaataacaga agtgaaatta   1680
cgagctttaa cattggttgc ttgaaacctt gcattaatat cagtccttaa atcaccagaa   1740
ccgattaaaa ttcggttttg ggatttaagg ttaggatctg cattatgtgt tttcctcaat   1800
cgcatattgt gagaattttt cccggcgatt gaagtatttt ttgttttttc cactcttaaa   1860
attgcataag ccatattcga aaacctcccg ttaaaagcag taaggttttt ttcttttttgg   1920
cccctgccag gctcacaccg agatttctcg gtatagtgag tataccttt ctgcaatatt    1980
gaaaatctat aaatacatct acaataaaaa aagcaaaagt caacggctca atccctcgca   2040
agggaaaatt aaaatttccc cttactcacg atttccaata aagaaaaaa gacagaacgc    2100
tgagcaagtc aaaattttaa ttttggcttg tgaagggttg accaagcgaa gcgcggtagg   2160
gaaatctgcg cagatgctta tgtattgccc ggaacgggaa acgtctgttg tagcggtagc   2220
gaaacacat ctcccggaac gggggttttc ttttgcgtag cctggcaagt tctgctcgat    2280
ctggaggttt gcaccgttta ctctcttact ttcttattgt ttaaatcttt acataccct    2340
ccagcccttg ctattactga cttaaatcaa aaaaagtta tagattccta taacctaaaa   2400
gttatagatt tctataaccc cagttataga ttcctataac cccctaagt tggtcattcg    2460
accaacttct tataactaag ttataaaaag ttgtaatcat gtattgacta gttgtatatt   2520
ttgtttataa cctgtctctt atacacatct caaccatcat cgatgaattg tgtctcaaaa   2580
tctctgatgt tacattgcac aagataaaaa tatatcatca tgaacaataa aactgtctgc   2640
ttacataaac agtaatacaa ggggtgttat gagccatatt caacgggaaa cgtcttgctc   2700
```

```
gaggccgcga ttaaattcca acatggatgc tgatttatat gggtataaat gggctcgcga    2760
taatgtcggg caatcaggtg cgacaatcta tcgattgtat gggaagcccg atgcgccaga    2820
gttgtttctg aaacatggca aaggtagcgt tgccaatgat gttacagatg agatggtcag    2880
actaaactgg ctgacggaat ttatgcctct tccgaccatc aagcattta tccgtactcc     2940 tgatgatgca tggttactca ccactgcgat ccccggaaaa acagcattcc aggtattaga    3000
agaatatcct gattcaggtg aaaatattgt tgatgcgctg cagtgttcc tgcgccggtt     3060 gcattcgatt cctgtttgta attgtccttt taacagcgat cgcgtatttc gtctcgctca    3120
ggcgcaatca cgaatgaata acggtttggt tgatgcgagt gattttgatg acgagcgtaa    3180
tggctggcct gttgaacaag tctggaaaga aatgcataaa cttttgccat tctcaccgga    3240
ttcagtcgtc actcatggtg atttctcact tgataacctt attttgacg aggggaaatt      3300 aataggttgt attgatgttg gacgagtcgg aatcgcagac cgataccagg atcttgccat    3360
cctatggaac tgcctcggtg agttttctcc ttcattacag aaacggcttt ttcaaaaata    3420
tggtattgat aatcctgata tgaataaatt gcagtttcat ttgatgctcg atgagttttt    3480
ctaatcagaa ttggttaatt ggttgtaaca ctggcagagc attacgctga cttgacggga    3540
cggcggcttt gttgaataaa tcgaactttt gctgagttga aggatcagat cacgcatctt    3600
cccgacaacg cagaccgttc cgtggcaaag caaaagttca aaatcaccaa ctggtccacc    3660
tacaacaaag ctctcatcaa ccgtggcggg gatcgatctt agatccgttg tttctcgtct    3720
aataaatgaa cgaaaaatac ttcaaatgac tgatggttat caggtcactg cttgggggc     3780 tagctatgtt aggagcgtct ttgatagaaa gacacttgac cgattgcggc ttgagattat    3840
gaattttgaa aaccgtagaa aatcaacatt taactatgat aagattccgt atgcgcacca    3900
agaaggaaga attccatatg cagattttcg tcaaaacttt gaccggtaaa accataacat    3960
tggaagttga atcttccgat accatcgaca acgttaagtc gaaaattcaa gacaaggaag    4020
gtatccctcc agatcaacaa agattgatct ttgccggtaa gcagctagaa gacggtagaa    4080
cgctgtctga ttcaacatt cagaaggagt ccaccttaca tcttgtctta agactccgcg      4140
gtggtttccc aaccattccc ttatccaggc tttttgacaa cgctagtctc cgcgcccatc    4200
gtctgcacca gctggccttt gacacctacc aggagtttga agaagcttat atcccaaagg    4260
aacagaagta ttcattcctg cagaaccccc agacctccct ctgtttctca gagtctattc    4320
cgacaccctc caacagggag gaaacacaac agaaatccaa cctcgagctg ctccgcatct    4380
ccctgctgct catccagtcg tggctggagc ccgtgcagtt cctcaggagt gtcttcgcca    4440
acagcctggt gtacggcgcc tctgacagca acgtctatga cctcctaaag gacctagagg    4500
aagggatcca aacgctgatg gggaggctgg aagatggcag ccccggact gggcagatct      4560 tcaagcagac ctacagcaag ttcgacacaa actcacacaa cgatgacgca ctactcaaga    4620
actacgggct gctctactgc ttcaggaagg acatggacaa ggtcgagaca ttcctgcgca    4680
tcgtgcagtg ccgctctgtg gagggcagct gtggcttcta aaaagtcgac gcggccgcaa    4740
gcttagcccg cttaatgagc gggctttttt ttagcttcag ggttgagatg tgtataagag    4800
acag                                                                 4804
```

<210> SEQ ID NO 19
<211> LENGTH: 3578
<212> TYPE: DNA
<213> ORGANISM: E. coli

<400> SEQUENCE: 19

```
actctagccc tgtctcttat acacatctca accatcatcg atgaattgtg tctcaaaatc     60
tctgatgtta cattgcacaa gataaaaata tatcatcatg aacaataaaa ctgtctgctt    120
acataaacag taatacaagg ggtgttatga gccatattca acgggaaacg tcttgctcga    180
ggccgcgatt aaattccaac atggatgctg atttatatgg gtataaatgg gctcgcgata    240
atgtcgggca atcaggtgcg acaatctatc gattgtatgg gaagcccgat gcgccagagt    300
tgtttctgaa acatggcaaa ggtagcgttg ccaatgatgt tacagatgag atggtcagac    360
taaactggct gacggaattt atgcctcttc cgaccatcaa gcattttatc cgtactcctg    420
atgatgcatg gttactcacc actgcgatcc ccggaaaaac agcattccag gtattagaag    480
aatatcctga ttcaggtgaa aatattgttg atgcgctggc agtgttcctg cgccggttgc    540
attcgattcc tgtttgtaat tgtcctttta acagcgatcg cgtatttcgt ctcgctcagg    600
cgcaatcacg aatgaataac ggtttggttg atgcgagtga ttttgatgac gagcgtaatg    660
gctggcctgt tgaacaagtc tggaaagaaa tgcataaact tttgccattc tcaccggatt    720
cagtcgtcac tcatggtgat ttctcacttg ataaccttat ttttgacgag gggaaattaa    780
taggttgtat tgatgttgga cgagtcggaa tcgcagaccg ataccaggat cttgccatcc    840
tatggaactg cctcggtgag ttttctcctt cattacagaa acggcttttt caaaaatatg    900
gtattgataa tcctgatatg aataaattgc agtttcattt gatgctcgat gagttttttct   960
aatcagaatt ggttaattgg ttgtaacact ggcagagcat tacgctgact tgacgggacg   1020
gcggctttgt tgaataaatc gaacttttgc tgagttgaag gatcagatca cgcatcttcc   1080
cgacaacgca gaccgttccg tggcaaagca aaagttcaaa atcaccaact ggtccaccta   1140
caacaaagct ctcatcaacc gtggcgggga tcctctagag tcgacctgca ggcatgcaag   1200
cttcagggtt gagatgtgta taagagacag actctagcca gtttccaagt agaaactaca   1260
gtttctaaac tgcaactttt tctacttttt gcaacttaat ctattgacta gtcctttata   1320
aatgttaaaa catatatata gaaataaata aaagaggag gtttctatgg atattggaaa   1380
tatattaaat gagagtttaa gtattgatta cgaaaaatta gatttgtttt tggaaaaata   1440
tgatttaaca ccagaacaaa aagttgcagt ttatgaattt cacgcaaaag cttataaaaa   1500
aaataaaact ttagttattt ctgaaacaaa agaaaataaa tttaaatcta tttccgaagg   1560
tgttgaatac gtgcatttat tcccaaaaaa tttaaaaatt ttaattaaaa aatatggttt   1620
aaatacaaac gaattattgg ttttaacgga aataatggag tcaatgcttt cacacggaaa   1680
tttattaatt aattttttcgc aaaaggcact tgcgaatta acaggaatta ataaatctac   1740
aatgtgtaaa acatttaaaa ccctcaaaca aaagcagtgt ttaattgaga aaacgaca   1800
tatttattta aattctgtga tatttatgaa agggttacct cataaattgt ttatgcaatt   1860
tagagatcat ttttttaaatt ctatctcata taaattagat gatgaagaag aatttgaaaa   1920
agtcttcgac gataatttta ttaaagcata cgaaaaaaat ctcaaagaga ttaaaaagaa   1980
aaagcaacaa ataaaagaaa agaaaatatc aaaagcatta gataattttg aaaaagaaat   2040
ctcgaaagaa tggaaggaaa agtttaaaga cgaagaggaa aatttcgaat tggttttga    2100
atcggaaata taaaaccgcc ctcgccgggc aggcgaatcc cttattgaaa tagaataaat   2160
tctattccac taagggattt ttttttattca ttgtttctcc acatttgcaa tattgacatt   2220
aacttccacc cggatataac agtagtataa gttgttgttt caacccgtct ttttgggtgg   2280
aacaacaagg cattttaggg atagagcaaa gcgaaggcca taaaattgcc acccccaacc   2340
```

```
gggggtcgtt gttcgatttg agcgatagcg aaaaattgaa cataaggggg gagggtttgg    2400
gttttacggt atttcaaatt tgagcaaagc gaattttttga aatttccggt tcttttaatt   2460
tgcaatgagg aaaaatcaat atgggtaatt caaaagaaa  tataaaaaaa ctaaatgata   2520
attttagaga ggatattta  gattatgcga tcgcgcacaa tctaaaatgt gctaacgcac    2580
ttgctatttt atacgcaacg ggttgccgtc cggacgaact ccaaaccgga gttactgtaa    2640
actatgacag taaaaaaat  gaaattgaat ttagaataat tggatcaaaa ctaaatagaa    2700
gaatgagaag aggcataggg gttagaaaaa taaaagtaaa aatcaataat gaaaatgcca    2760 ggtttttaa  aaacattgtt gataaattta ttgaaaccc  aatgtcatat gatcacaaaa    2820
tcaaaattga aagtgccaaa gcattttccg ggtacataac aaaaatatcg aaaaagctat    2880
ggcccaggaa aacctatcat gcttctgcat attctttttag acatgcaaaa gcaacggaat    2940
taaaaaattc cgattatgat aaaatcgaaa tagctcagat tatgggccat gcctcagtta    3000
gatctcagca gagttacgga agaaagagca aaaaagcaa  aggtggattt gatgacatcg    3060
cagatgtcga aaccaatgtt aaaccccgtg gcggtgatag attattgaga tttaagatcg    3120
caaataaaaa caaagcagcg gcaaaaattg ccgatacttc caccccccagc agtcctccac   3180 cggctcccgt tcgtcgcttc aaaatgtgaa ccgtgagcag ttcaggaggt tccctcctgg    3240
actgtgaagg gttggcccgt ccggtcagga cggttttaca gcaaaatcct ccatagcgaa    3300
gcagaagccc ggaacgggta actggatggt tttcccccgt gggggattga tctgttactt    3360
gaaaaccaat gatcttaaaa gccatctcaa aagttgaaaa tttcaccccc ttagtgttct    3420
taaaattctt agatgttctt aggagttaaa aaactactct ctaaccattg atattactgg    3480
atttttaaaa aaggcagttg tcaaaaactt caaccgtagt tgtcaaattc gtcaactcca    3540
gttgtcaaat tcgtcaactg aggttgtcaa atccgaca                            3578

<210> SEQ ID NO 20
<211> LENGTH: 5366
<212> TYPE: DNA
<213> ORGANISM: E. coli

<400> SEQUENCE: 20
actctagccc tgtctcttat acacatctca accatcatcg atgaattgtg tctcaaaatc      60
tctgatgtta cattgcacaa gataaaaata tatcatcatg aacaataaaa ctgtctgctt     120
acataaacag taatacaagg ggtgttatga gccatatttca acgggaaacg tcttgctcga    180
ggccgcgatt aaattccaac atggatgctg atttatatgg gtataaatgg gctcgcgata    240
atgtcgggca atcaggtgcg acaatctatc gattgtatgg gaagcccgat gcgccagagt    300
tgtttctgaa acatggcaaa ggtagcgttg ccaatgatgt tacagatgag atggtcagac    360
taaactggct gacggaattt atgcctcttc cgaccatcaa gcattttatc cgtactcctg    420
atgatgcatg gttactcacc actgcgatcc ccggaaaaac agcattccag gtattagaag    480
aatatcctga ttcaggtgaa aatattgttg atgcgctggc agtgttcctg cgccggttgc    540
attcgattcc tgtttgtaat tgtcctttta acagcgatcg cgtatttcgt ctcgctcagg    600
cgcaatcacg aatgaataac ggtttggttg atgcgagtga ttttgatgac gagcgtaatg    660
gctggcctgt tgaacaagtc tggaaagaaa tgcataaact tttgccattc tcaccggatt    720
cagtcgtcac tcatggtgat ttctcacttg ataaccttat ttttgacgag gggaaattaa    780
taggttgtat tgatgttgga cgagtcggaa tcgcagaccg ataccaggat cttgccatcc    840
tatggaactg cctcggtgag ttttctcctt cattacagaa acggcttttt caaaaatatg    900
```

```
gtattgataa tcctgatatg aataaattgc agtttcattt gatgctcgat gagttttcct    960
aatcagaatt ggttaattgg ttgtaacact ggcagagcat tacgctgact tgacgggacg   1020
gcggctttgt tgaataaatc gaacttttgc tgagttgaag gatcagatca cgcatcttcc   1080
cgacaacgca gaccgttccg tggcaaagca aaagttcaaa atcaccaact ggtccaccta   1140
caacaaagct ctcatcaacc gtggcgggga tccggaccgt tggcgatgtg cggtttgcta   1200
cattcacaga tgttcttcgc cacttccagc agcaggtcat caggggtgat ttcaggatcg   1260
tagataaagg tcaggttcgg tgaaacctgc ttcaactctg catctgcacg taagatcgcg   1320
cgggtaatgg gcgaatcaga cgggccgata ttggcgtgca taaaggcgtc tggcagggtt   1380
ctgtcgaggt aacgccagaa acgttttatt cgaacatcga tctcgtcttg tgttagaatt   1440
aattctaaca tacggttgca acaacgcatc cagttgcccc aggtagaccg gcatcgatgt   1500
gaccgacggt acgtggtggt aaagaatggt cagcagagag agtgcgtcat caagatcttt   1560
cgcgccttcc agctccagcc attcggaacc gttcgccaga aacgggcgt aatcgggtaa   1620
gacatagcgc ggtttgtacg gcgcatgacc ttcaaacata tcgcagatta caccttcatc   1680
cagcgcgcgg cgggcttcgg caggaagctg tgggtaaggc agattgtttt ctgcttccag   1740
tgccagaaaa tggcgcttct gctccgggct aagcactggg ctggtgacaa tttgctggca   1800
acgttgttgc agtgcatttt catgagaagt gggcatcttc ttttcctttt atgccgaagg   1860
tgatgcgcca ttgtaagaag tttcgtgatg ttcactttga tcctgatgcg tttgccacca   1920
ctgacgcatt catttgaaag tgaattattt gaaccagatc gcattacagt gatgcaaact   1980
tgtaagtaga tttccttaat tgtgatgtgt atcgaagtgt gttgcggagt agatgttaga   2040
atactaacaa actcgcaagg tgaatttat ggcgacaag cctaggtttg tttaacttta   2100
aggagaaatc atatgcaaat ttttgttaaa actttaactg gtaaaaccat taccttagaa   2160
gttgaatctt cagataccat tgataatgtt aaatctaaaa ttcaagataa agaaggtatt   2220
cctccagatc aacaacgtct aatatttgca ggtaaacagt tagaagatgg tcgtaccctg   2280
tctgattata acattcagaa agaatctacc ttacatctgg tcttacgtct ccgcggtggt   2340
ttcccaacca ttcccttaag taggcttttt gacaacgcta tgctccgcgc ccatcgtctg   2400
caccagctgg cctttgacac ctaccaggag tttgaagaag cttatatccc aaaggaacag   2460
aagtattcat tcctgcagaa ccccccagacc tccctctgtt tctcagagtc tattccgaca   2520
ccctccaaca gggaggaaac acaacagaaa tccaacctcg agctgctccg catctccctg   2580
ctgctcatcc agtcgtggct ggagcccgtg cagttcctca ggagtgtctt cgccaacagc   2640
ctggtgtacg gcgcctctga cagcaacgtc tatgacctcc taaaggacct agaggaaggg   2700
atccaaacgc tgatggggag gctggaagat ggcagccccc ggactgggca gatcttcaag   2760
cagacctaca gcaagttcga cacaaactca cacaacgatg acgcactact caagaactac   2820
gggctgctct actgcttcag gaaggacatg gacaaggtcg agacattcct gcgcatcgtg   2880
cagtgccgct ctgtgggg cagctgtggc ttctaaaaag tcgacctgca ggcatgcaag   2940
cttagcccgc ttaatgagcg ggcttttttt tctcgacctg caggcatgca agcttcaggg   3000
ttgagatgtg tataagagac agactctagc cagtttccaa gtagaaacta cagtttctaa   3060
actgcaactt tttctacttt ttgcaactta atctattgac tagtccttta taaatgttaa   3120
aacatatata tagaaataaa taaaagagg aggtttctat ggatattgga aatatattaa   3180
atgagagttt aagtattgat tacgaaaaat tagatttgtt tttggaaaaa tatgatttaa   3240
```

```
caccagaaca aaaagttgca gtttatgaat ttcacgcaaa agcttataaa aaaaataaaa    3300
ctttagttat ttctgaaaca aaagaaaata aatttaaatc tatttccgaa gtgttgaata    3360
cgtgcattta ttcccaaaaa atttaaaaat tttaattaaa aaatatggtt taaatacaaa    3420
cgaattattg gttttaacgg aaataatgga gtcaatgctt tcacacgaaa atttattaat    3480
taatttttcg caaaaggcac tttgcgaatt aacaggaatt aataaatcta caatgtgtaa    3540
aacatttaaa accctcaaac aaaagcagtg tttaattgag aaaaacggac atatttattt    3600
aaattctgtg atatttatga aagggttacc tcataaattg tttatgcaat ttagagatca    3660
ttttttaaat tctatctcat ataaattaga tgatgaagaa gaatttgaaa aagtcttcga    3720
cgataatttt attaaagcat acgaaaaaaa tctcaaagag attaaaaaga aaaagcaaca    3780
aataaaagaa aagaaaatat caaaagcatt agataatttt gaaaagaaa tctcgaaaga    3840
atggaaggaa aagtttaaag acgaagagga aaatttcgaa tttggttttg aatcggaaat    3900
ataaaaccgc cctcgccggg caggcgaatc ccttattgaa atagaataaa ttctattcca    3960
ctaagggatt tttttattc attgtttctc cacatttgca atattgacat taacttccac    4020
ccggatataa cagtagtata agttgttgtt tcaacccgtc ttttgggtg gaacaacaag    4080
gcatttagg gatagagcaa agcgaaggcc ataaaattgc cacccccaac cggggggtcgt    4140
tgttcgattt gagcgatagc gaaaaattga acataagggg ggagggttg ggttttacgg    4200
tatttcaaat ttgagcaaag cgaattttttg aaatttccgg ttcttttaat ttgcaatgag    4260
gaaaaatcaa tatgggtaat tcaaaagaa atataaaaaa actaaatgat aattttagag    4320
aggatatttt agattatgcg atcgcgcaca atctaaaatg tgctaacgca cttgctattt    4380
tatacgcaac gggttgccgt ccggacgaac tccaaaccgg agttactgta aactatgaca    4440
gtaaaaaaaa tgaaattgaa tttagaataa ttggatcaaa actaaataga agaatgagaa    4500
gaggcatagg ggttagaaaa ataaaagtaa aaatcaataa tgaaaatgcc aggtttttta    4560
aaaacattgt tgataaattt attgaaaacc caatgtcatg atcacaaaat caaaattgaa    4620
agtgccaaag cattttccgg gtacataaca aaaatatcga aaagctatg gcccaggaaa    4680
acctatcatg cttctgcata ttcttttaga catgcaaaag caacggaatt aaaaaattcc    4740
gattatgata aaatcgaaat agctcagatt atgggccatg cctcagttag atctcagcag    4800
agttacggaa gaaagagcaa aaaaagcaaa ggtggatttg atgacatcgc agatgtcgaa    4860
accaatgtta aaccccgtgg cggtgataga ttattgagat ttaagatcgc aaataaaaac    4920
aaagcagcgg caaaaattgc cgatacttcc accccccagca gtcctccacc ggctcccgtt    4980
cgtcgcttca aaatgtgaac cgtgagcagt tcaggaggtt ccctcctgga ctgtgaaggg    5040
ttggcccgtc cggtcaggac ggttttacag caaaatcctc catagcgaag cagaagcccg    5100
gaacggtaac tggatggttt tcccccgtgg gggattgatc tgttacttga aaccaatga    5160
tcttaaaagc catctcaaaa gttgaaaatt tcacccccctt agtgttctta aaattcttag    5220
atgttcttag gagttaaaaa actactctct aaccattgat attactggat ttttaaaaaa    5280
ggcagttgtc aaaaacttca accgtagttg tcaaattcgt caactccagt tgtcaaattc    5340
gtcaactgag gttgtcaaat ccgaca                                         5366
```

<210> SEQ ID NO 21
<211> LENGTH: 5186
<212> TYPE: DNA
<213> ORGANISM: E. coli

<400> SEQUENCE: 21

```
tagagcgcac gaatgagggc cgacaggaag caaagctgaa aggaatcaaa tttggccgca      60
ggcgtaccgt ggacaggaac gtcgtgctga cgcttcatca gaagggcact ggtgcaacgg     120
aaattgctca tcagctcagt attgcccgct ccacggttta taaaattctt gaagacgaaa     180
gggcctcgtg atacgcctat ttttataggt taatgtcatg ataataatgg tttcttagac     240
gtcaggtggc acttttcggg gaaatgtgcg cggaaccccT attTgtttaT ttttctaaat     300
acattcaaat atgtatccgc tcatgagaca ataaccctga taaatgcttc aataatattg     360
aaaaaggaag agtatgagta ttcaacattt ccgtgtcgcc cttattccct tttttgcggc     420
attttgcctt cctgtttttg ctcacccaga aacgctggtg aaagtaaaag atgctgaaga     480
tcagttgggt gcacgagtgg gttacatcga actggatctc aacagcggta agatccttga     540
gagttttcgc cccgaagaac gttttccaat gatgagcact tttaaagttc tgctatgtgg     600
cgcggtatta tcccgtgttg acgccgggca agagcaactc ggtcgccgca tacactattc     660
tcagaatgac ttggttgagt actcaccagt cacagaaaag catcttacgg atggcatgac     720
agtaagagaa ttatgcagtg ctgccataac catgagtgat aacactgcgg ccaacttact     780
tctgacaacg atcggaggac cgaaggagct aaccgctttt ttgcacaaca tgggggatca     840
tgtaactcgc cttgatcgtt gggaaccgga gctgaatgaa gccataccaa acgacgagcg     900
tgacaccacg atgcctgcag caatggcaac aacgttgcgc aaactattaa ctggcgaact     960
acttactcta gcttcccggc aacaattaat agactggatg gaggcggata aagttgcagg    1020
accacttctg cgctcggccc ttccggctgg ctggtttatt gctgataaat ctggagccgg    1080
tgagcgtggg tctcgcggta tcattgcagc actggggcca gatggtaagc cctcccgtat    1140
cgtagttatc tacacgacgg ggagtcaggc aactatggat gaacgaaata cagatcgc     1200
tgagataggt gcctcactga ttaagcattg gtaactgtca gaccaagttt actcatatat    1260
actttagatt gatttaaaac ttcattttta atttaaaagg atctaggtga agatcctttt    1320
tgataatctc atgaccaaaa tcccttaacg tgagttttcg ttccactgag cgtcagaccc    1380
catcgccgtt ctcgatacgc tgaaccgtgc gcacgctcat cccggacagt tcagcaagct    1440
gctcctggga ccaggcacgc gcaagacgca gcgacctgaa tttgttggta tcactcattt    1500
cctgtctccg aatggaagat ggtcagcaca cagtgttgac cgcgtaatcc tgcgcgacca    1560
cgatcttaac ccgacagtaa cgtgacagcg gtctgacatg ccgcattgag gtctttgaaa    1620
ccgtaacttc agaagcatgt acggtcagat ttaacataag agttcattgt acgcaccgtt    1680
aaaacgcgct cagcgcgctt ctggcgcaaa accgtaaaa atggatgttt tccccggggt    1740
aaaccggaaa aatgcgtcag gaacgctttc agcgcgttgc atgactatgc atgaaactga    1800
atggcgatcg gtttgggcgc gtctgatgcc cataaggcgt attttcggac gttttcagcc    1860
ctgataagaa gaaatcagac tgtagttaca gacgagtcgt gagcgattca ctacgggagt    1920
cgtcggcgag tcatccagta ttttcctcg cgactctctg gcgactcgcc ttctctgaac    1980
accagagcga cagtgtgttg agtcatcgat aaatcaccga cgactcgttg ccgagtcatc    2040
cagtagtcgc cgacgagccg cttttgtata atccgaata agaaaatata ttttcaaac     2100
cataacaaca tgatttaaaa agcaaatcag aaaaagtta gttttgcgtg gggtgtgggc    2160
atcctgggaa tgagaacaga ctcgcgtttt tctggaggaa ctgcggggat ttttgattaa    2220
acaatagtca ccgcagagcg gaattttatg caacgctggc tgtgcggcac ggggattttt    2280
aatccccgg ccgttattc atctccacgg gcgacgggga tacataaacc cgacagcaga    2340
```

```
ggacgggtga gcgcgaatcc cagagatgat gaaaaaagag gcagagaaac gcgcccaggt    2400
acgttttatc ttattgcttt ggtgttgtcc agggtgtcgg ggctgtgccc tgaccaggtg    2460
gcatttgtct gattgcgcgt gcgcggtccg acaaatgcac atcctgcccc gtcctgtacg    2520 tgttttttc  accagaacaa cttcacgaag tggcggatga acgctaccaa cgttgccggg    2580
aacgcttcgg cgatgatggc ataacgggct gatacaggca gctcccggag acggacacag    2640
cttgcctgtg agcggatgcc gggagccgac aagcccgtca gggcgcgtca gcggttttta    2700
gcgggtgtcg gggcgcagcc atgacccagt cacgtagcga tagcggagtg tatactggct    2760
taatatgtta aatcggagtg gtaattcagg gaagtgcttc atgtggcaaa ggaaaaatgt    2820
ggctatcgtg cgtaagtgca acatgtaggt aaaggtgaaa tgacgcctcc tcgctcactc    2880
ggtcgctacg ctcctgccgt gagactgcgg cgggcgttac cggctcacaa ataacgggat    2940
acgcaggcag tgctcaaatc aggaaggacc ggaaaaagga tgcggcgtag ccgttttttcc    3000 ataggctccg ccccctgac  aagcatcacg aaatctgacg ctcaaatcag tggcggcgaa    3060
acccgacagg actataaaga tcccaggcgt ttccccctgg tagctccctc gtgcgctctc    3120
ctgttcctgc ctttcggttt accggtgtca ttccgctgtt atggccgcgt ttgtctcatt    3180
ccacgcctga cactcagttc cgggtaggca gttcgctcca agctggactg tatgcacgaa    3240
ccccccgttc agtccgacta ccacgcccgt tccgtaact  atcaacttga gtccaacccg    3300
gaaagacacg acaaatcgcc agtggcggta gccattggta actgagatgt gcgagagatt    3360
tatctggagt tcttgaagtg ggggcctgag tgcggctaca ctggaaggac agtttaggtg    3420
actcgtctcg cacaagacag ttaccaggtt aagcagttcc ccaactgacc taaccttcga    3480
tcaaaccacc tcccaggtg  gttttttcgt tttcagagca agagattacg cgcagaaaaa    3540
aaggatctca agaagatcct ttttacagga gcgattatcg tcttcatcca tgaaggcgtt    3600
tgaagattaa accggcctat ttcatagatc gtaaaatcag ggttttggga tggccgatga    3660
aaccccataa aaacccataa atacatacac ctactaacaa tcatcttttg ctgtaccagg    3720
gtatgaaaag tctcagggtt ccaccccaga atacgccatc aacaagtcct gtcacaccgc    3780
caaataacat gcaaaaaatt gcggatgacc gtaatccggg gtgcagatca atgactgaga    3840
caagtataaa cttcatgcaa aaagtaatta caatcagtcc caaagtcagc ggtgtcccgg    3900
ccctgataat catgcccgga ttatctgaat ttctcagcgg gggctgtgag cgccacaacc    3960
tgtatccaag agcggtgcct acgagcagtc ctgccgtcat cattgtaagg cttacgccag    4020
caagttttgt ctcagtgata acaccttatg ctccccatac aaggaaaagt atcgggagaa    4080
aaaacaaacg cccggttgtc atctcccggt cataaagagc agcaaaaccg cgtcgtagta    4140
aaaaagccag caggatcaag cttcagggtt gagatgtgta taagagacag actctagcca    4200
gtttccaagt agaaactaca gtttctaaac tgcaactttt tctacttttt gcaacttaat    4260
ctattgacta gtcctttata aatgttaaaa catatatata gaaataaata aaagaggag    4320 gttcatatgc aaattttgt  taaaacttta actggtaaaa ccattacctt agaagttgaa    4380
tcttcagata ccattgataa tgttaaatct aaaattcaag ataaagaagg tattcctcca    4440
gatcaacaac gtctaatatt tgcaggtaaa cagttagaag atggtcgtac cctgtctgat    4500
tataacattc agaagaatc  taccttacat ctggtcttac gtctccgcgg tggtttccca    4560
accattccct taagtaggct ttttgacaac gctatgctcc gcgcccatcg tctgcaccag    4620
ctggcctttg acacctacca ggagtttgaa gaagcttata tcccaaagga acagaagtat    4680
tcattcctgc agaaccccca gacctccctc tgtttctcag agtctattcc gacaccctcc    4740
```

-continued

```
aacagggagg aaacacaaca gaaatccaac ctcgagctgc tccgcatctc cctgctgctc    4800
atccagtcgt ggctggagcc cgtgcagttc ctcaggagtg tcttcgccaa cagcctggtg    4860 tacgcgcct ctgacagcaa cgtctatgac ctcctaaagg acctagagga agggatccaa     4920
acgctgatgg ggaggctgga agatggcagc ccccggactg ggcagatctt caagcagacc    4980
tacagcaagt tcgacacaaa ctcacacaac gatgacgcac tactcaagaa ctacgggctg    5040
ctctactgct tcaggaagga catggacaag gtcgagacat tcctgcgcat cgtgcagtgc    5100
cgctctgtgg agggcagctg tggcttctaa aaagtcgact ctagctacag cctcctttcg    5160
gaggctgttt tttatctcga ggatcc                                         5186

<210> SEQ ID NO 22
<211> LENGTH: 5229
<212> TYPE: DNA
<213> ORGANISM: E. coli

<400> SEQUENCE: 22
tagagcgcac gaatgagggc cgacaggaag caaagctgaa aggaatcaaa tttggccgca      60
ggcgtaccgt ggacaggaac gtcgtgctga cgcttcatca gaagggcact ggtgcaacgg    120
aaattgctca tcagctcagt attgcccgct ccacggttta taaaattctt gaagacgaaa    180
gggcctcgtg atacgcctat ttttataggt taatgtcatg ataataatgg tttcttagac    240
gtcaggtggc acttttcggg gaaatgtgcg cggaacccct atttgtttat ttttctaaat    300
acattcaaat atgtatccgc tcatgagaca ataaccctga taaatgcttc aataatattg    360
aaaaaggaag agtatgagta ttcaacattt ccgtgtcgcc cttattccct ttttgcggc     420 attttgcctt cctgttttg ctcacccaga acgctggtg aaagtaaaag atgctgaaga     480
tcagttgggt gcacgagtgg gttacatcga actggatctc aacagcggta agatccttga    540
gagttttcgc cccgaagaac gttttccaat gatgagcact tttaaagttc tgctatgtgg    600
cgcggtatta tcccgtgttg acgccgggca agagcaactc ggtcgccgca tacactattc    660
tcagaatgac ttggttgagt actcaccagt cacagaaaag catcttacgg atggcatgac    720
agtaagagaa ttatgcagtg ctgccataac catgagtgat aacactgcgg ccaacttact    780
tctgacaacg atcggaggac cgaaggagct aaccgctttt ttgcacaaca tgggggatca    840
tgtaactcgc cttgatcgtt gggaaccgga gctgaatgaa gccataccaa acgacgagcg    900
tgacaccacg atgcctgcag caatggcaac aacgttgcgc aaactattaa ctggcgaact    960
acttactcta gcttcccggc aacaattaat agactggatg gaggcggata agttgcagg    1020 accacttctg cgctcggccc ttccggctgg ctggtttatt gctgataaat ctggagccgg    1080
tgagcgtggg tctcgcggta tcattgcagc actggggcca gatggtaagc cctcccgtat    1140
cgtagttatc tacacgacgg ggagtcaggc aactatggat gaacgaaata cagatcgc     1200 tgagataggt gcctcactga ttaagcattg gtaactgtca gaccaagttt actcatatat    1260
actttagatt gatttaaaac ttcatttta atttaaaagg atctaggtga agatccttt     1320 tgataatctc atgaccaaaa tcccttaacg tgagttttcg ttccactgag cgtcagaccc    1380
catcgccgtt ctcgatacgc tgaaccgtgc gcacgctcat cccggacagt tcagcaagct    1440
gctcctggga ccaggcacgc gcaagacgca gcgacctgaa tttgttggta tcactcattt    1500
cctgtctccg aatggaagat ggtcagcaca cagtgttgac cgcgtaatcc tgcgcgacca    1560
cgatcttaac ccgacagtaa cgtgacagcg gtctgacatg ccgcattgag gtctttgaaa    1620
```

-continued

```
ccgtaacttc agaagcatgt acggtcagat ttaacataag agttcattgt acgcaccgtt      1680
aaaacgcgct cagcgcgctt ctggcgcaaa aaccgtaaaa atggatgttt tcccccgggt      1740
aaaccggaaa aatgcgtcag gaacgctttc agcgcgttgc atgactatgc atgaaactga      1800
atggcgatcg gtttgggcgc gtctgatgcc cataaggcgt attttcggac gttttcagcc      1860
ctgataagaa gaaatcagac tgtagttaca gacgagtcgt gagcgattca ctacgggagt      1920
cgtcggcgag tcatccagta ttttctcctcg cgactctctg gcgactcgcc ttctctgaac      1980
accagagcga cagtgtgttg agtcatcgat aaatcaccga cgactcgttg ccgagtcatc      2040
cagtagtcgc cgacgagccg cttttgtata atccgaata agaaaatata ttttccaaac      2100
cataacaaca tgatttaaaa agcaaatcag aaaaaagtta gttttgcgtg gggtgtgggc      2160
atcctgggaa tgagaacaga ctcgcgtttt tctggaggaa ctgcggggat ttttgattaa      2220
acaatagtca ccgcagagcg gaattttatg caacgctggc tgtgcggcac ggggattttt      2280 aatccccccgg cccgttattc atctccacgg gcgacgggga tacataaacc cgacagcaga      2340
ggacgggtga gcgcgaatcc cagagatgat gaaaaaagag gcagagaaac gcgcccaggt      2400
acgttttatc ttattgcttt ggtgttgtcc agggtgtcgg ggctgtgccc tgaccaggtg      2460
gcatttgtct gattgcgcgt gcgcggtccg acaaatgcac atcctgcccc gtcctgtacg      2520 tgttttttc accagaacaa cttcacgaag tggcggatga acgctaccaa cgttgccggg      2580
aacgcttcgg cgatgatggc ataacgggct gatacaggca gctcccggag acggacacag      2640
cttgcctgtg agcggatgcc gggagccgac aagcccgtca gggcgcgtca gcgggtttta      2700
gcgggtgtcg gggcgcagcc atgacccagt cacgtagcga tagcggagtg tatactggct      2760
taatatgtta aatcggagtg gtaattcagg gaagtgcttc atgtggcaaa ggaaaaatgt      2820
ggctatcgtg cgtaagtgca acatgtaggt aaaggtgaaa tgacgcctcc tcgctcactc      2880
ggtcgctacg ctcctgccgt gagactgcgg cgggcgttac cggctcacaa ataacgggat      2940
acgcaggcag tgctcaaatc aggaaggacc ggaaaaagga tgcggcgtag ccgttttttcc      3000 ataggctccg ccccccctgac aagcatcacg aaatctgacg ctcaaatcag tggcggcgaa      3060
acccgacagg actataaaga tcccaggcgt ttccccctgg tagctccctc gtgcgctctc      3120
ctgttcctgc ctttcggttt accggtgtca ttccgctgtt atggccgcgt ttgtctcatt      3180
ccacgcctga cactcagttc cgggtaggca gttcgctcca agctggactg tatgcacgaa      3240
ccccccgttc agtccgacta ccacgcccgt tccggtaact atcaacttga gtccaacccg      3300
gaaagacacg acaaatcgcc agtggcgtta gccattggta actgagatgt gcgagagatt      3360
tatctggagt tcttgaagtg ggggcctgag tgcggctaca ctggaaggac agtttaggtg      3420
actcgtctcg cacaagacag ttaccaggtt aagcagttcc ccaactgacc taaccttcga      3480
tcaaaccacc tccccaggtg gttttttcgt tttcagagca agagattacg cgcagaaaaa      3540
aaggatctca agaagatcct ttttacagga gcgattatcg tcttcatcca tgaaggcgtt      3600
tgaagattaa accggcctat ttcatagatc gtaaaatcag ggttttggga tggccgatga      3660
aaccccataa aaacccataa atacatacac ctactaacaa tcatcttttg ctgtaccagg      3720
gtatgaaaag tctcagggtt ccaccccaga atacgccatc aacaagtcct gtcacaccgc      3780
caaataacat gcaaaaaatt gcggatgacc gtaatccggg gtgcagatca atgactgaga      3840
caagtataaa cttcatgcaa aaagtaatta caatcagtcc caaagtcagc ggtgtcccgg      3900
ccctgataat catgcccgga ttatctgaat ttctcagcgg gggctgtgag cgccacaacc      3960
tgtatccaag agcggtgcct acgagcagtc ctgccgtcat cattgtaagg cttacgccag      4020
```

-continued

```
caagttttgt ctcagtgata acaccttatg ctccccatac aaggaaaagt atcgggagaa    4080
aaaacaaacg cccggttgtc atctcccggt cataaagagc agcaaaaccg cgtcgtagta    4140
aaaaagccag caggatcctc gagataaaaa acagcctccg aaaggaggct gtagtctaga    4200
gcggccgcat ttaaatgtcg acttttaga agccacagct gccctccaca gagcggcact     4260
gcacgatgcg caggaatgtc tcgaccttgt ccatgtcctt cctgaagcag tagagcagcc    4320
cgtagttctt gagtagtgcg tcatcgttgt gtgagtttgt gtcgaacttg ctgtaggtct    4380
gcttgaagat ctgcccagtc cggggggctgc catcttccag cctccccatc agcgtttgga    4440
tcccttcctc taggtccttt aggaggtcat agacgttgct gtcagaggcg ccgtacacca    4500
ggctgttggc aagacactc ctgaggaact gcacgggctc cagccacgac tggatgagca    4560
gcagggagat gcggagcagc tcgaggttgg atttctgttg tgtttcctcc ctgttggagg    4620
gtgtcggaat agactctgag aaacagaggg aggtctgggg gttctgcagg aatgaatact    4680
tctgttcctt tgggatataa gcttcttcaa actcctggta ggtgtcaaag gccagctggt    4740
gcagacgatg ggcgcggagc atagcgttgt caaaaagcct acttaaggga atggttggga    4800
aaccaccgcg gagacgtaag accagatgta aggtagattc tttctgaatg ttataatcag    4860
acagggtacg accatcttct aactgtttac ctgcaaatat tagacgttgt tgatctggag    4920
gaataccttc tttatcttga attttagatt taacattatc aatggtatct gaagattcaa    4980
cttctaaggt aatggtttta ccagttaaag ttttaacaaa aatttgcata tgaacctcct    5040 cttttttattt atttctatat atatgtttta acatttataa aggactagtc aatagattaa    5100
gttgcaaaaa gtagaaaaag ttgcagttta gaaactgtag tttctacttg gaaactggct    5160
agagtctgtc tcttatacac atctcaaccc tgaagcttag cccgctcatt aagcgggcta    5220
gcttgatcc                                                            5229
```

<210> SEQ ID NO 23
<211> LENGTH: 3887
<212> TYPE: DNA
<213> ORGANISM: E. coli

<400> SEQUENCE: 23

```
gttaggcgcg aggtgctatg gtcaaagtgt ggtgtcaggc ggggaggagg cttatatgag      60
atgtaatccg gccgatacat ataccaagat gatttaagta ttcctctttg tgaggttgga    120
tgtctaattt ataaaggatc ttcttgagat cctttttttc cgcgcgtaat ctcttgccct    180
gtaaacgaaa aaaccaccct ggcaggtggt ttttcgaagg ttaggtaatc ctggcagatc    240
ccctaaccgt ggtaacagtc ttgtgcgaga catgtcacca aatttgtcct ttcagtgtag    300
cctcactaag gccgccactt caagaactct tgagacatct ctcgcacatc ctgtttgcca    360
atggccgttg ccaatggcga ttagtcgtgt ctttccgggt tggactcaag ttgatagtta    420
ccggataagg cgcagcggtc ggactgaacg gggggttcgt gcatacagtc catcctggag    480
cgaactgcct tcccggaact gagtgtcagg cgtggaatga aaaccgcgg ccataacagc    540 ggagtgacac cggtaaaccg aaaggcagga atgcgggga gcacgaggga gccaccaggg    600
ggaaacgcct ggtatcttta agccgcatcg ggtttcgcca ccactgattt gagcgtcaga    660
ttctgtgatg cttgtcaggg gggcggagcc tatgaaaaa cggctttggc gcggccttat    720
gctttcttcg ttaagtatct tcctggcatc ccccaggaaa tttctgatcc atccgtaagc    780
ccgtcccgct cgccgcagcc gaacgaccga gcggagcgag tcagtgagcg aggaagcgga    840
```

```
atatattctg tatcacattt tctcctgacg cgttttcttt cactttctgc gcctgtctta    900
tgtggcatta atgctatgtg ttactgccat gctacatctt aagccagtat acactccgct    960
agtgctccgt gactggtccg gcgctgcgcc cggaacccgc ctgtaccggt tcagcagccg   1020
ttccggcctg actgcaattt ttttttttc atccctgccc gctaccctgt aaacctttct   1080
tctgcgttgc cgttaacctg tctcttatac acatctcaac catcatcgat gaattgtgtc   1140
tcaaaatctc tgatgttaca ttgcacaaga taaaaatata tcatcatgaa caataaaact   1200
gtctgcttac ataaacagta atacaagggg tgttatgagc catattcaac gggaaacgtc   1260
ttgctcgagg ccgcgattaa attccaacat ggatgctgat ttatatgggt ataaatgggc   1320
tcgcgataat gtcgggcaat caggtgcgac aatctatcga ttgtatggga agcccgatgc   1380
gccagagttg tttctgaaac atggcaaagg tagcgttgcc aatgatgtta cagatgagat   1440
ggtcagacta aactggctga cggaatttat gcctcttccg accatcaagc attttatccg   1500
tactcctgat gatgcatggt tactcaccac tgcgatcccc ggaaaaacag cattccaggt   1560
attagaagaa tatcctgatt caggtgaaaa tattgttgat gcgctggcag tgttcctgcg   1620
ccggttgcat tcgattcctg tttgtaattg tccttttaac agcgatcgcg tatttcgtct   1680
cgctcaggcg caatcacgaa tgaataacgg tttggttgat gcgagtgatt ttgatgacga   1740
gcgtaatggc tggcctgttg aacaagtctg gaaagaaatg cataaacttt tgccattctc   1800
accggattca gtcgtcactc atggtgattt ctcacttgat aaccttattt ttgacgaggg   1860
gaaattaata ggttgtattg atgttggacg agtcggaatc gcagaccgat accaggatct   1920
tgccatccta tggaactgcc tcggtgagtt ttctccttca ttacagaaac ggcttttca   1980 aaaatatggt attgataatc ctgatatgaa taaattgcag tttcatttga tgctcgatga   2040 gttttttctaa tcagaattgg ttaattggtt gtaacactgg cagagcatta cgctgacttg   2100
acgggacggc ggctttgttg aataaatcga acttttgctg agttgaagga tcagatcacg   2160
catcttcccg acaacgcaga ccgttccgtg gcaaagcaaa agttcaaaat caccaactgg   2220
tccacctaca caaagctct catcaaccgt ggcgggatc caaacgcaaa aaggccatcc   2280
gtcaggatgg ccttctgctt aatttgatgc ctggcagttt atggcgggcg tcctgcccgc   2340
caccctccgg gccgttgctt cgcaacgttc aaatccgctc ccggcggatt tgtcctactc   2400
aggagagcgt tcaccgacaa acaacagata aaacgaaagg cccagtcttt cgactgagcc   2460
tttcgtttta tttgtctaga gtcgactttt tagaagccac agctgccctc cacagagcgg   2520
cactgcacga tgcgcaggaa tgtctcgacc ttgtccatgt ccttcctgaa gcagtagagc   2580
agcccgtagt tcttgagtag tgcgtcatcg ttgtgtgagt ttgtgtcgaa cttgctgtag   2640
gtctgcttga agatctgccc agtccggggg ctgccatctt ccagcctccc catcagcgtt   2700
tggatccctt cctctaggtc ctttaggagg tcatagacgt tgctgtcaga ggcgccgtac   2760
accaggctgt tggcgaagac actcctgagg aactgcacgg gctccagcca cgactggatg   2820
agcagcaggg agatgcggag cagctcgagg ttggatttct gttgtgtttc ctccctgttg   2880
gagggtgtcg aatagactc tgagaaacag agggaggtct gggggttctg caggaatgaa   2940
tacttctgtt cctttgggat ataagcttct tcaaactcct ggtaggtgtc aaaggccagc   3000
tggtgcagac gatgggcgcg gagactacgc ttgtcaaaaa gcctacttaa gggaatggtt   3060
gggaaaccac cgcggagacg taagaccaga tgtaaggtag attctttctg aatgttataa   3120
tcagacaggt tacgaccatc ttctaactgt ttacctgcaa atattagacg ttgttgatct   3180
ggaggaatac cttctttatc ttgaattta gatttaacat tatcaatggt atctgaagat   3240
```

-continued

```
tcaacttcta aggtaatggt tttaccagtt aaagttttaa caaaaatttg catatgaaac    3300
ctccttaaag ttaattttat ttatttctat atatatgttt taacatttat aaaggactag    3360
tcaatagatt aagttgcaaa aagtagaaaa agttgcagtt tagaaactgt agtttctact    3420
tggaaactgg ctagagtctg tctcttatac acatctcaac cctgaagctt ttagctttgg    3480
tgatgcaatt tgctgggatt ttggcggaga accacaggta aagaaaaagg ccacattagc    3540 ggccttttc ggagaagatg ctcagtgcgg aatttcggag acttctttaa cgtcggtttt    3600
attgatctgc tgtttgacac cattcgcgtc tgtatagcca agcaggcctg agtctgattc    3660
tttaggtttg ccgtcgctga caatagtgcg accgtcattg gtgtgtatgg catagcttgt    3720
gcgcgtgcag ccggtgaggg ctgaaagcgc aactgccgct gcaacactg aaacaaaaat    3780 cttttcaaa gccagctcct tttatccata tcagttttgg tcactaacca tctaactata    3840
ggtcattttt tatgtgaaaa gaggcttgat ggtgggctgt atatcga                 3887
```

<210> SEQ ID NO 24
<211> LENGTH: 721
<212> TYPE: PRT
<213> ORGANISM: Saccharomyces cerevisiae

<400> SEQUENCE: 24

```
Gly Gly Phe Ile Ala Gly Leu Val Asn Asp Gly Asn Thr Cys Phe Met
  1               5                  10                  15

Asn Ser Val Leu Gln Ser Leu Ala Ser Ser Arg Glu Leu Met Glu Phe
             20                  25                  30

Leu Asp Asn Asn Val Ile Arg Thr Tyr Glu Glu Ile Glu Gln Asn Glu
         35                  40                  45

His Asn Glu Glu Gly Asn Gly Gln Glu Ser Ala Gln Asp Glu Ala Thr
     50                  55                  60

His Lys Lys Asn Thr Arg Lys Gly Gly Lys Val Tyr Gly Lys His Lys
 65                  70                  75                  80

Lys Lys Leu Asn Arg Lys Ser Ser Lys Glu Asp Glu Glu Lys Ser
                 85                  90                  95

Gln Glu Pro Asp Ile Thr Phe Ser Val Ala Leu Arg Asp Leu Leu Ser
            100                 105                 110

Ala Leu Asn Ala Lys Tyr Tyr Arg Asp Lys Pro Tyr Phe Lys Thr Asn
        115                 120                 125

Ser Leu Leu Lys Ala Met Ser Lys Ser Pro Arg Lys Asn Ile Leu Leu
    130                 135                 140

Gly Tyr Asp Gln Glu Asp Ala Gln Glu Phe Phe Gln Asn Ile Leu Ala
145                 150                 155                 160

Glu Leu Glu Ser Asn Val Lys Ser Leu Asn Thr Glu Lys Leu Asp Thr
                165                 170                 175

Thr Pro Val Ala Lys Ser Glu Leu Pro Asp Asp Ala Leu Val Gly Gln
            180                 185                 190

Leu Asn Leu Gly Glu Val Gly Thr Val Tyr Ile Pro Thr Glu Gln Ile
        195                 200                 205

Asp Pro Asn Ser Ile Leu His Asp Lys Ser Ile Gln Asn Phe Thr Pro
    210                 215                 220

Phe Lys Leu Met Thr Pro Leu Asp Gly Ile Thr Ala Glu Arg Ile Gly
225                 230                 235                 240

Cys Leu Gln Cys Gly Glu Asn Gly Gly Ile Arg Tyr Ser Val Phe Ser
                245                 250                 255
```

```
Gly Leu Ser Leu Asn Leu Pro Asn Glu Asn Ile Gly Ser Thr Leu Lys
            260                 265                 270

Leu Ser Gln Leu Leu Ser Asp Trp Ser Lys Pro Glu Ile Ile Glu Gly
        275                 280                 285

Val Glu Cys Asn Arg Cys Ala Leu Thr Ala Ala His Ser His Leu Phe
    290                 295                 300

Gly Gln Leu Lys Glu Phe Glu Lys Lys Pro Glu Gly Ser Ile Pro Glu
305                 310                 315                 320

Lys Pro Ile Asn Ala Val Lys Asp Arg Val His Gln Ile Glu Glu Val
                325                 330                 335

Leu Ala Lys Pro Val Ile Asp Asp Glu Asp Tyr Lys Lys Leu His Thr
            340                 345                 350

Ala Asn Met Val Arg Lys Cys Ser Lys Ser Lys Gln Ile Leu Ile Ser
        355                 360                 365

Arg Pro Pro Leu Leu Ser Ile His Ile Asn Arg Ser Val Phe Asp
370                 375                 380

Pro Arg Thr Tyr Met Ile Arg Lys Asn Asn Ser Lys Val Leu Phe Lys
385                 390                 395                 400

Ser Arg Leu Asn Leu Ala Pro Trp Cys Cys Asp Ile Asn Glu Ile Asn
                405                 410                 415

Leu Asp Ala Arg Leu Pro Met Ser Lys Lys Glu Lys Ala Ala Gln Gln
            420                 425                 430

Asp Ser Ser Glu Asp Glu Asn Ile Gly Gly Glu Tyr Tyr Thr Lys Leu
        435                 440                 445

His Glu Arg Phe Glu Gln Glu Phe Glu Asp Ser Glu Glu Lys Glu
    450                 455                 460

Tyr Asp Asp Ala Glu Gly Asn Tyr Ala Ser His Tyr Asn His Thr Lys
465                 470                 475                 480

Asp Ile Ser Asn Tyr Asp Pro Leu Asn Gly Glu Val Asp Gly Val Thr
                485                 490                 495

Ser Asp Asp Glu Asp Glu Tyr Ile Glu Glu Thr Asp Ala Leu Gly Asn
            500                 505                 510

Thr Ile Lys Lys Arg Ile Ile Glu His Ser Asp Val Glu Asn Glu Asn
        515                 520                 525

Val Lys Asp Asn Glu Glu Leu Gln Glu Ile Asp Asn Val Ser Leu Asp
    530                 535                 540

Glu Pro Lys Ile Asn Val Glu Asp Gln Leu Glu Thr Ser Ser Asp Glu
545                 550                 555                 560

Glu Asp Val Ile Pro Ala Pro Pro Ile Asn Tyr Ala Arg Ser Phe Ser
                565                 570                 575

Thr Val Pro Ala Thr Pro Leu Thr Tyr Ser Leu Arg Ser Val Ile Val
            580                 585                 590

His Tyr Gly Thr His Asn Tyr Gly His Tyr Ile Ala Phe Arg Lys Tyr
        595                 600                 605

Arg Gly Cys Trp Trp Arg Ile Ser Asp Glu Thr Val Tyr Val Val Asp
    610                 615                 620

Glu Ala Glu Val Leu Ser Thr Pro Gly Val Phe Met Leu Phe Tyr Glu
625                 630                 635                 640

Tyr Asp Phe Asp Glu Glu Thr Gly Lys Met Lys Asp Asp Leu Glu Ala
                645                 650                 655

Ile Leu Ser Asn Asn Glu Glu Asp Asp Glu Lys Glu Gln Glu Gln Lys
            660                 665                 670

Gly Val Gln Glu Pro Lys Glu Ser Gln Glu Gln Gly Glu Gly Glu Glu
```

```
                      675                 680                 685
Gln Glu Glu Gly Gln Gln Met Lys Phe Arg Thr Glu Asp His
        690                 695                 700

Arg Asp Ile Ser Gly Lys Asp Val Asn Gly Ser His His His His
705                 710                 715                 720

His

<210> SEQ ID NO 25
<211> LENGTH: 765
<212> TYPE: PRT
<213> ORGANISM: E. coli

<400> SEQUENCE: 25

Gly Gly Asp His Leu Asn Tyr Ile Trp Glu Ser Trp Ser Glu Met Thr
1               5                   10                  15

Thr Asn Phe Arg Asn Asn Asn Ser Leu Ser Arg Trp Leu Pro Arg Ser
            20                  25                  30

Lys Phe Thr His Leu Asp Glu Glu Ile Leu Lys Arg Gly Gly Phe Ile
        35                  40                  45

Ala Gly Leu Trp Asn Asp Gly Asn Thr Cys Phe Met Asn Ser Trp Leu
    50                  55                  60

Gln Ser Leu Ala Ser Ser Arg Glu Leu Met Glu Phe Leu Asp Asn Asn
65                  70                  75                  80

Trp Ile Arg Thr Tyr Glu Glu Ile Glu Gln Asn Glu His Asn Glu Glu
                85                  90                  95

Gly Asn Gly Gln Glu Ser Ala Gln Asp Glu Ala Thr His Lys Lys Asn
            100                 105                 110

Thr Arg Lys Gly Gly Lys Trp Tyr Gly Lys His Lys Lys Lys Leu Asn
        115                 120                 125

Arg Lys Ser Ser Ser Lys Glu Asp Glu Glu Lys Ser Gln Glu Pro Asp
    130                 135                 140

Ile Thr Phe Ser Trp Ala Leu Arg Asp Leu Leu Ser Ala Leu Asn Ala
145                 150                 155                 160

Lys Tyr Tyr Arg Asp Lys Pro Tyr Phe Lys Thr Asn Ser Leu Leu Lys
                165                 170                 175

Ala Met Ser Lys Ser Pro Arg Lys Asn Ile Leu Leu Gly Tyr Asp Gln
            180                 185                 190

Glu Asp Ala Gln Glu Phe Phe Gln Asn Ile Leu Ala Glu Leu Glu Ser
        195                 200                 205

Asn Trp Lys Ser Leu Asn Thr Glu Lys Leu Asp Thr Thr Pro Trp Ala
    210                 215                 220

Lys Ser Glu Leu Pro Asp Asp Ala Leu Trp Gly Gln Leu Asn Leu Gly
225                 230                 235                 240

Glu Trp Gly Thr Trp Tyr Ile Pro Thr Glu Gln Ile Asp Pro Asn Ser
                245                 250                 255

Ile Leu His Asp Lys Ser Ile Gln Asn Phe Thr Pro Phe Lys Leu Met
            260                 265                 270

Thr Pro Leu Asp Gly Ile Thr Ala Glu Arg Ile Gly Cys Leu Gln Cys
        275                 280                 285

Gly Glu Asn Gly Gly Ile Arg Tyr Ser Trp Phe Ser Gly Leu Ser Leu
    290                 295                 300

Asn Leu Pro Asn Glu Asn Ile Gly Ser Thr Leu Lys Leu Ser Gln Leu
305                 310                 315                 320

Leu Ser Asp Trp Ser Lys Pro Glu Ile Ile Glu Gly Trp Glu Cys Asn
```

-continued

```
                325                 330                 335
Arg Cys Ala Leu Thr Ala Ala His Ser His Leu Phe Gly Gln Leu Lys
            340                 345                 350

Glu Phe Glu Lys Lys Pro Glu Gly Ser Ile Pro Glu Lys Pro Ile Asn
        355                 360                 365

Ala Trp Lys Asp Arg Trp His Gln Ile Glu Glu Trp Leu Ala Lys Pro
    370                 375                 380

Trp Ile Asp Asp Glu Asp Tyr Lys Lys Leu His Thr Ala Asn Met Trp
385                 390                 395                 400

Arg Lys Cys Ser Lys Ser Lys Gln Ile Leu Ile Ser Arg Pro Pro
                405                 410                 415

Leu Leu Ser Ile His Ile Asn Arg Ser Trp Phe Asp Pro Arg Thr Tyr
                420                 425                 430

Met Ile Arg Lys Asn Asn Ser Lys Trp Leu Phe Lys Ser Arg Leu Asn
                435                 440                 445

Leu Ala Pro Trp Cys Cys Asp Ile Asn Glu Ile Asn Leu Asp Ala Arg
            450                 455                 460

Leu Pro Met Ser Lys Lys Glu Lys Ala Ala Gln Gln Asp Ser Ser Glu
465                 470                 475                 480

Asp Glu Asn Ile Gly Gly Glu Tyr Tyr Thr Lys Leu His Glu Arg Phe
                485                 490                 495

Glu Gln Glu Phe Glu Asp Ser Glu Glu Lys Glu Tyr Asp Asp Ala
            500                 505                 510

Glu Gly Asn Tyr Ala Ser His Tyr Asn His Thr Lys Asp Ile Ser Asn
        515                 520                 525

Tyr Asp Pro Leu Asn Gly Glu Trp Asp Gly Trp Thr Ser Asp Asp Glu
    530                 535                 540

Asp Glu Tyr Ile Glu Glu Thr Asp Ala Leu Gly Asn Thr Ile Lys Lys
545                 550                 555                 560

Arg Ile Ile Glu His Ser Asp Trp Glu Asn Glu Asn Trp Lys Asp Asn
                565                 570                 575

Glu Glu Leu Gln Glu Ile Asp Asn Trp Ser Leu Asp Glu Pro Lys Ile
            580                 585                 590

Asn Trp Glu Asp Gln Leu Glu Thr Ser Ser Asp Glu Glu Asp Trp Ile
        595                 600                 605

Pro Ala Pro Pro Ile Asn Tyr Ala Arg Ser Phe Ser Thr Trp Pro Ala
    610                 615                 620

Thr Pro Leu Thr Tyr Ser Leu Arg Ser Trp Ile Trp His Tyr Gly Thr
625                 630                 635                 640

His Asn Tyr Gly His Tyr Ile Ala Phe Arg Lys Tyr Arg Gly Cys Trp
                645                 650                 655

Trp Arg Ile Ser Asp Glu Thr Trp Tyr Trp Asp Glu Ala Glu Trp
            660                 665                 670

Leu Ser Thr Pro Gly Trp Phe Met Leu Phe Tyr Glu Tyr Asp Phe Asp
        675                 680                 685

Glu Glu Thr Gly Lys Met Lys Asp Asp Leu Glu Ala Ile Leu Ser Asn
    690                 695                 700

Asn Glu Glu Asp Asp Glu Lys Glu Gln Glu Lys Gly Trp Gln Glu
705                 710                 715                 720

Pro Lys Glu Ser Gln Glu Gln Gly Glu Gly Glu Gln Glu Glu Gly
                725                 730                 735

Gln Glu Gln Met Lys Phe Glu Arg Thr Glu Asp His Arg Asp Ile Ser
            740                 745                 750
```

```
            Gly Lys Asp Trp Asn Gly Ser His His His His His
                    755                 760                 765

<210> SEQ ID NO 26
<211> LENGTH: 804
<212> TYPE: DNA
<213> ORGANISM: Homo sapiens
<220> FEATURE:
<221> NAME/KEY: CDS
<222> LOCATION: (1)...(804)

<400> SEQUENCE: 26 atg caa att ttt gtt aaa act tta act ggt aaa acc att acc tta gaa      48
Met Gln Ile Phe Val Lys Thr Leu Thr Gly Lys Thr Ile Thr Leu Glu
  1               5                  10                  15 gtt gaa tct tca gat acc att gat aat gtt aaa tct aaa att caa gat      96
Val Glu Ser Ser Asp Thr Ile Asp Asn Val Lys Ser Lys Ile Gln Asp
                 20                  25                  30 aaa gaa ggt att cct cca gat caa caa cgt cta ata ttt gca ggt aaa     144
Lys Glu Gly Ile Pro Pro Asp Gln Gln Arg Leu Ile Phe Ala Gly Lys
             35                  40                  45 cag tta gaa gat ggt cgt acc ctg tct gat tat aac att cag aaa gaa     192
Gln Leu Glu Asp Gly Arg Thr Leu Ser Asp Tyr Asn Ile Gln Lys Glu
         50                  55                  60 tct acc tta cat ctg gtc tta cgt ctc cgc ggt ggt ttc cca acc att     240
Ser Thr Leu His Leu Val Leu Arg Leu Arg Gly Gly Phe Pro Thr Ile
 65                  70                  75                  80 ccc tta agt agg ctt ttt gac aac gct atg ctc cgc gcc cat cgt ctg     288
Pro Leu Ser Arg Leu Phe Asp Asn Ala Met Leu Arg Ala His Arg Leu
                 85                  90                  95 cac cag ctg gcc ttt gac acc tac cag gag ttt gaa gaa gct tat atc     336
His Gln Leu Ala Phe Asp Thr Tyr Gln Glu Phe Glu Glu Ala Tyr Ile
                100                 105                 110 cca aag gaa cag aag tat tca ttc ctg cag aac ccc cag acc tcc ctc     384
Pro Lys Glu Gln Lys Tyr Ser Phe Leu Gln Asn Pro Gln Thr Ser Leu
            115                 120                 125 tgt ttc tca gag tct att ccg aca ccc tcc aac agg gag gaa aca caa     432
Cys Phe Ser Glu Ser Ile Pro Thr Pro Ser Asn Arg Glu Glu Thr Gln
        130                 135                 140 cag aaa tcc aac ctc gag ctg ctc cgc atc tcc ctg ctc atc cag         480
Gln Lys Ser Asn Leu Glu Leu Leu Arg Ile Ser Leu Leu Leu Ile Gln
145                 150                 155                 160 tcg tgg ctg gag ccc gtg cag ttc ctc agg agt gtc ttc gcc aac agc     528
Ser Trp Leu Glu Pro Val Gln Phe Leu Arg Ser Val Phe Ala Asn Ser
                165                 170                 175 ctg gtg tac ggc gcc tct gac agc aac gtc tat gac ctc cta aag gac     576
Leu Val Tyr Gly Ala Ser Asp Ser Asn Val Tyr Asp Leu Leu Lys Asp
            180                 185                 190 cta gag gaa ggg atc caa acg ctg atg ggg agg ctg gaa gat ggc agc     624
Leu Glu Glu Gly Ile Gln Thr Leu Met Gly Arg Leu Glu Asp Gly Ser
        195                 200                 205 ccc cgg act ggg cag atc ttc aag cag acc tac agc aag ttc gac aca     672
Pro Arg Thr Gly Gln Ile Phe Lys Gln Thr Tyr Ser Lys Phe Asp Thr
    210                 215                 220 aac tca cac aac gat gac gca cta ctc aag aac tac ggg ctg ctc tac     720
Asn Ser His Asn Asp Asp Ala Leu Leu Lys Asn Tyr Gly Leu Leu Tyr
225                 230                 235                 240 tgc ttc agg aag gac atg gac aag gtc gag aca ttc ctg cgc atc gtg     768
Cys Phe Arg Lys Asp Met Asp Lys Val Glu Thr Phe Leu Arg Ile Val
                245                 250                 255
```

```
cag tgc cgc tct gtg gag ggc agc tgt ggc ttc taa                     804
Gln Cys Arg Ser Val Glu Gly Ser Cys Gly Phe *
        260                 265
```

<210> SEQ ID NO 27
<211> LENGTH: 267
<212> TYPE: PRT
<213> ORGANISM: Homo sapiens

<400> SEQUENCE: 27

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Phe Pro Thr Ile
65                  70                  75                  80

Pro Leu Ser Arg Leu Phe Asp Asn Ala Met Leu Arg Ala His Arg Leu
                85                  90                  95

His Gln Leu Ala Phe Asp Thr Tyr Gln Glu Phe Glu Glu Ala Tyr Ile
            100                 105                 110

Pro Lys Glu Gln Lys Tyr Ser Phe Leu Gln Asn Pro Gln Thr Ser Leu
        115                 120                 125

Cys Phe Ser Glu Ser Ile Pro Thr Pro Ser Asn Arg Glu Glu Thr Gln
    130                 135                 140

Gln Lys Ser Asn Leu Glu Leu Leu Arg Ile Ser Leu Leu Leu Ile Gln
145                 150                 155                 160

Ser Trp Leu Glu Pro Val Gln Phe Leu Arg Ser Val Phe Ala Asn Ser
                165                 170                 175

Leu Val Tyr Gly Ala Ser Asp Ser Asn Val Tyr Asp Leu Leu Lys Asp
            180                 185                 190

Leu Glu Glu Gly Ile Gln Thr Leu Met Gly Arg Leu Glu Asp Gly Ser
        195                 200                 205

Pro Arg Thr Gly Gln Ile Phe Lys Gln Thr Tyr Ser Lys Phe Asp Thr
    210                 215                 220

Asn Ser His Asn Asp Asp Ala Leu Leu Lys Asn Tyr Gly Leu Leu Tyr
225                 230                 235                 240

Cys Phe Arg Lys Asp Met Asp Lys Val Glu Thr Phe Leu Arg Ile Val
                245                 250                 255

Gln Cys Arg Ser Val Glu Gly Ser Cys Gly Phe
            260                 265
```

<210> SEQ ID NO 28
<211> LENGTH: 6
<212> TYPE: DNA
<213> ORGANISM: E. coli

<400> SEQUENCE: 28

```
aggagg                                                              6
```

<210> SEQ ID NO 29
<211> LENGTH: 252
<212> TYPE: DNA
<213> ORGANISM: Saccharomyces cerevesia

<400> SEQUENCE: 29

```
ggggaattca tatgcaaatt tttgttaaaa ctttaactgg taaaaccatt accttagaag      60
ttgaatcttc agataccatt gataatgtta aatctaaaat tcaagataaa gaaggtattc     120
ctccagatca acaacgtcta atatttgcag gtaaacagtt agaagatggt cgtaccctgt    180
ctgattataa cattcagaaa gaatctacct tacatctggt cttacgtctc cgcggtggtt    240
aagtcgacga ga                                                        252
```

<210> SEQ ID NO 30
<211> LENGTH: 60
<212> TYPE: DNA
<213> ORGANISM: Saccharomyces cervesciae

<400> SEQUENCE: 30

```
ttgaatcttc agataccatt gataatgtta aatctaaaat tcaagataaa gaaggtattc      60
```

<210> SEQ ID NO 31
<211> LENGTH: 26
<212> TYPE: DNA
<213> ORGANISM: Saccharomyces cerevesiae

<400> SEQUENCE: 31

```
ttagatttaa cattatcaat ggtatc                                          26
```

<210> SEQ ID NO 32
<211> LENGTH: 19
<212> TYPE: DNA
<213> ORGANISM: Saccharomyces cervesiae

<400> SEQUENCE: 32

```
agacgttgtt gatctggag                                                  19
```

<210> SEQ ID NO 33
<211> LENGTH: 24
<212> TYPE: DNA
<213> ORGANISM: Saccharomyces cervesiae

<400> SEQUENCE: 33

```
acagggtacg accatcttct aact                                            24
```

<210> SEQ ID NO 34
<211> LENGTH: 60
<212> TYPE: DNA
<213> ORGANISM: Saccharomyces cerevesiae

<400> SEQUENCE: 34

```
ctgattataa cattcagaaa gaatctacct tacatctggt cttacgtctc cgcggtggtt      60
```

<210> SEQ ID NO 35
<211> LENGTH: 24
<212> TYPE: DNA
<213> ORGANISM: Saccharomyces cerevesiae

<400> SEQUENCE: 35

```
agaccagatg taaggtagat tctt                                            24
```

<210> SEQ ID NO 36
<211> LENGTH: 12

```
-continued

<212> TYPE: DNA
<213> ORGANISM: Saccharomyces cerevesiae

<400> SEQUENCE: 36
aagtcgacga ga                                                              12
```